(12) United States Patent
Lawrence et al.

(10) Patent No.: US 12,403,250 B2
(45) Date of Patent: Sep. 2, 2025

(54) INFUSION SET

(71) Applicant: Becton, Dickinson and Company, Franklin Lakes, NJ (US)

(72) Inventors: Tyson Lawrence, Cambridge, MA (US); James McGee, Watertown, MA (US); Todd Taylor, Cambridge, MA (US); Rob Colonna, Boston, MA (US); Eric Sugalski, Arlington, MA (US); Zenas Lu, Cambridge, MA (US); Chris K. Barmore, Arlington, MA (US); Robert Banik, Hollywood, FL (US); Peter Skutnik, Midland Park, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 648 days.

(21) Appl. No.: 17/167,565

(22) Filed: Feb. 4, 2021

(65) Prior Publication Data

US 2021/0154397 A1     May 27, 2021

Related U.S. Application Data

(63) Continuation of application No. 13/138,209, filed as application No. PCT/US2010/000145 on Jan. 21, 2010, now Pat. No. 10,933,191.

(Continued)

(51) Int. Cl.
*A61M 39/08* (2006.01)
*A61M 5/158* (2006.01)
(Continued)

(52) U.S. Cl.
CPC ............ *A61M 5/158* (2013.01); *A61M 5/427* (2013.01); *A61M 39/08* (2013.01); *A61M 5/002* (2013.01);
(Continued)

(58) Field of Classification Search
CPC .. A61M 2005/1586; A61M 2005/1587; A61M 39/0247; A61M 2039/0258;
(Continued)

(56) References Cited

U.S. PATENT DOCUMENTS 3,247,851 A    4/1966   Seibert
4,128,173 A    12/1978   Lazarus et al.
(Continued)

FOREIGN PATENT DOCUMENTS

JP    57-211353 A    12/1982
JP    61-293456 A    12/1986
(Continued)

*Primary Examiner* — Kevin C Sirmons
*Assistant Examiner* — William R Frehe
(74) *Attorney, Agent, or Firm* — Dickinson Wright PLLC

(57) ABSTRACT

An infusion set, including a set having a skin contacting surface, a catheter extending from the set, and a flexible ring having an integral fluid path therethrough. The flexible ring is configured to expand to a first diameter to allow placement over the set, and contract to a second diameter to securely circumscribe an outer diameter of the set. The infusion set also includes a tubing length secured to the flexible ring, and a fitting or spike disposed at an end of the tubing length and extending into the flexible ring. The fitting or spike is configured to sealably mate with an opening of the set to permit communication of a medicament therebetween.

12 Claims, 38 Drawing Sheets

Related U.S. Application Data

(60) Provisional application No. 61/202,019, filed on Jan. 21, 2009.

(51) Int. Cl.
*A61M 5/42* (2006.01)
*A61M 5/00* (2006.01)
*A61M 5/142* (2006.01)

(52) U.S. Cl.
CPC . *A61M 5/14244* (2013.01); *A61M 2005/1585* (2013.01); *A61M 2005/1586* (2013.01); *A61M 2005/1587* (2013.01); *A61M 2005/1588* (2013.01); *A61M 2205/586* (2013.01); *A61M 2209/088* (2013.01)

(58) Field of Classification Search
CPC ...... A61M 203/0261; A61M 2039/027; A61M 2039/0276; A61M 2039/0282; A61M 25/02; A61M 2025/0213; A61J 15/00; A61J 15/0015; A61J 15/0053; A61J 15/0061
See application file for complete search history.

(56) References Cited

U.S. PATENT DOCUMENTS

| | | | |
|---|---|---|---|
| 4,216,860 A | | 8/1980 | Heimann |
| 4,335,770 A | * | 6/1982 | Kulle ........................ A61J 1/10 383/29 |
| 4,523,679 A | | 6/1985 | Paikoff et al. |
| 4,588,398 A | | 5/1986 | Daugherty et al. |
| 4,605,399 A | | 8/1986 | Weston et al. |
| 4,743,231 A | | 5/1988 | Kay et al. |
| 4,755,173 A | | 7/1988 | Konopka et al. |
| 4,769,893 A | * | 9/1988 | Cassidy ................. F16H 25/24 29/418 |
| 5,048,684 A | | 9/1991 | Scott |
| 5,188,588 A | * | 2/1993 | Schoendorfer ....... A61M 1/302 604/6.07 |
| 5,226,427 A | | 7/1993 | Buckberg et al. |
| 5,292,325 A | | 3/1994 | Gurmarnik |
| 5,318,543 A | | 6/1994 | Ross et al. |
| 5,417,671 A | | 5/1995 | Jackson |
| 5,474,181 A | | 12/1995 | Shillington et al. |
| 5,582,599 A | | 12/1996 | Daneshvar |
| 5,620,419 A | | 4/1997 | Lui |
| 5,797,882 A | | 8/1998 | Purdy et al. |
| 5,797,954 A | | 8/1998 | Shaffer et al. |
| 5,911,707 A | | 6/1999 | Wolvek et al. |
| 5,925,017 A | | 7/1999 | Kriesel et al. |
| 6,461,644 B1 | | 10/2002 | Jackson et al. |
| 6,475,196 B1 | | 11/2002 | Vachon |
| 6,575,954 B1 | | 6/2003 | Ravizza |
| 6,736,797 B1 | | 5/2004 | Larsen et al. |
| 6,749,588 B1 | | 6/2004 | Howell et al. |
| 6,959,812 B2 | | 11/2005 | Reif |
| 7,207,974 B2 | | 4/2007 | Safabash |
| 7,981,085 B2 | | 7/2011 | Ethelfeld |
| 8,945,057 B2 | | 2/2015 | Gyrn |
| 2002/0022855 A1 | | 2/2002 | Bobroff et al. |
| 2002/0077599 A1 | | 6/2002 | Wojcik |
| 2002/0095138 A1 | | 7/2002 | Lynch et al. |
| 2002/0156434 A1 | | 10/2002 | Antwerp et al. |
| 2002/0177816 A1 | * | 11/2002 | Brimhall ........... A61M 25/0637 604/174 |
| 2004/0168944 A1 | | 9/2004 | Massengale et al. |
| 2005/0013957 A1 | | 1/2005 | Leschinsky |
| 2005/0107743 A1 | | 5/2005 | Fangrow, Jr. |
| 2006/0030815 A1 | * | 2/2006 | Csincsura .......... A61M 39/1011 604/93.01 |
| 2006/0065772 A1 | | 3/2006 | Grant et al. |
| 2006/0129090 A1 | | 6/2006 | Moberg et al. |
| 2006/0173410 A1 | * | 8/2006 | Moberg ................ A61M 25/02 604/93.01 |
| 2006/0282045 A1 | | 12/2006 | Wilkinson et al. |
| 2007/0021729 A1 | | 1/2007 | Mogensen |
| 2007/0299409 A1 | | 12/2007 | Whitbourne et al. |
| 2008/0103367 A1 | | 5/2008 | Burba |
| 2008/0215003 A1 | | 9/2008 | Kornerup et al. |
| 2008/0243051 A1 | | 10/2008 | DeStefano |
| 2008/0243084 A1 | * | 10/2008 | DeStefano ............ A61M 5/158 604/180 |
| 2008/0243085 A1 | | 10/2008 | DeStefano |
| 2008/0255516 A1 | | 10/2008 | Yodfat et al. |
| 2008/0295960 A1 | | 12/2008 | Schalau, II et al. |

FOREIGN PATENT DOCUMENTS

| | | |
|---|---|---|
| JP | 64-005566 A | 1/1989 |
| JP | 3-240664 A | 10/1991 |
| JP | 2000-279508 | 10/2000 |
| JP | 2003-527138 A | 9/2003 |
| JP | 2005-503242 A | 2/2005 |
| JP | 2005-506110 A | 3/2005 |
| JP | 2007-511325 A | 5/2007 |
| JP | 2008-501483 A | 1/2008 |
| WO | 1997-028750 A1 | 8/1997 |
| WO | 97/42901 | 11/1997 |
| WO | 99/33504 | 7/1999 |
| WO | 02/083021 A1 | 10/2002 |
| WO | 2004101071 A2 | 11/2004 |
| WO | 2005079441 A2 | 9/2005 |
| WO | 2006097111 A2 | 9/2006 |
| WO | 2007093182 A2 | 8/2007 |
| WO | 2008014791 A1 | 2/2008 |
| WO | 2009070896 A1 | 6/2009 |
| WO | 2010080715 A1 | 7/2010 |

* cited by examiner

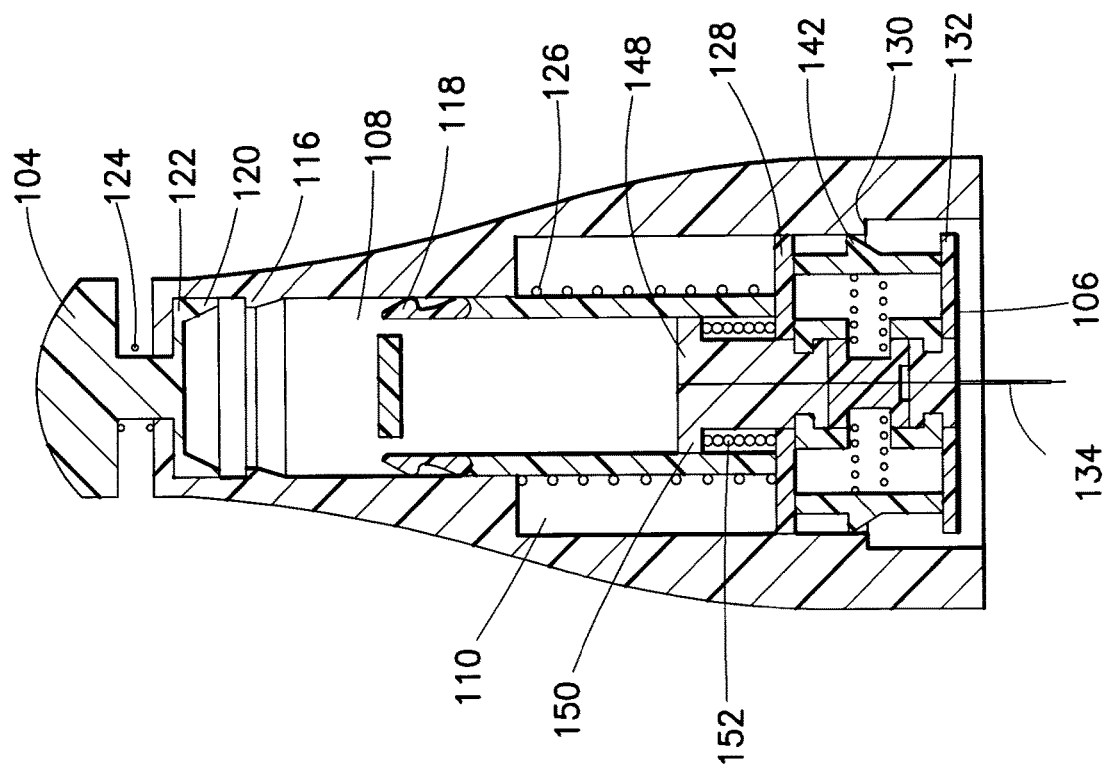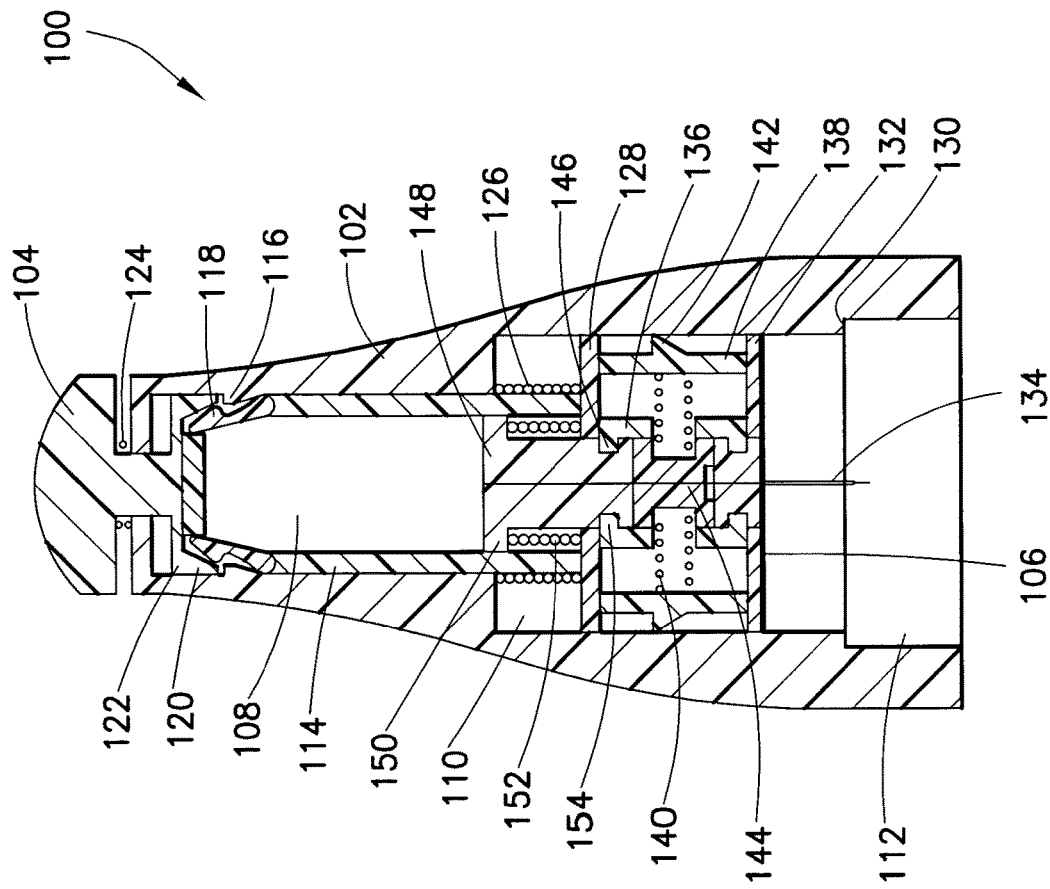

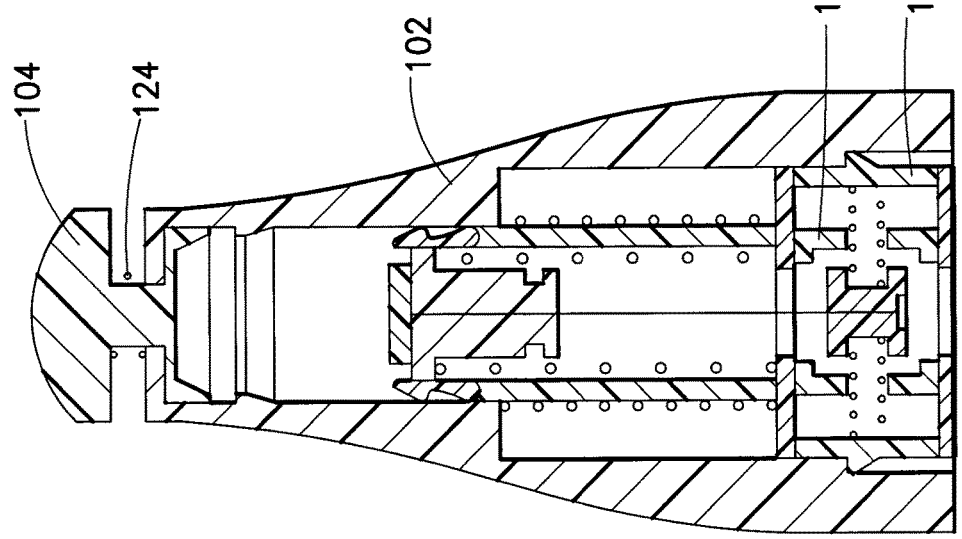
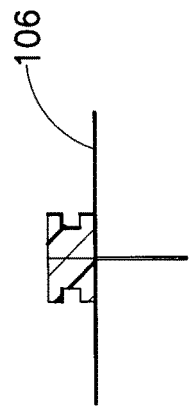
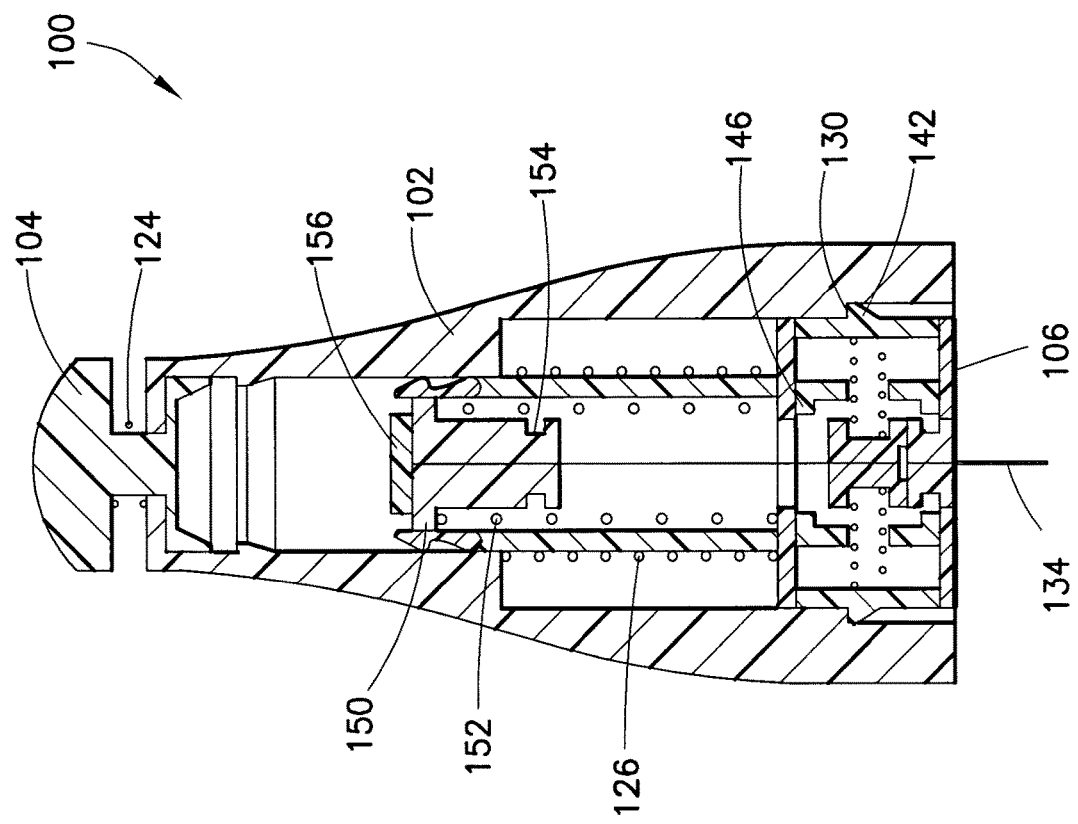

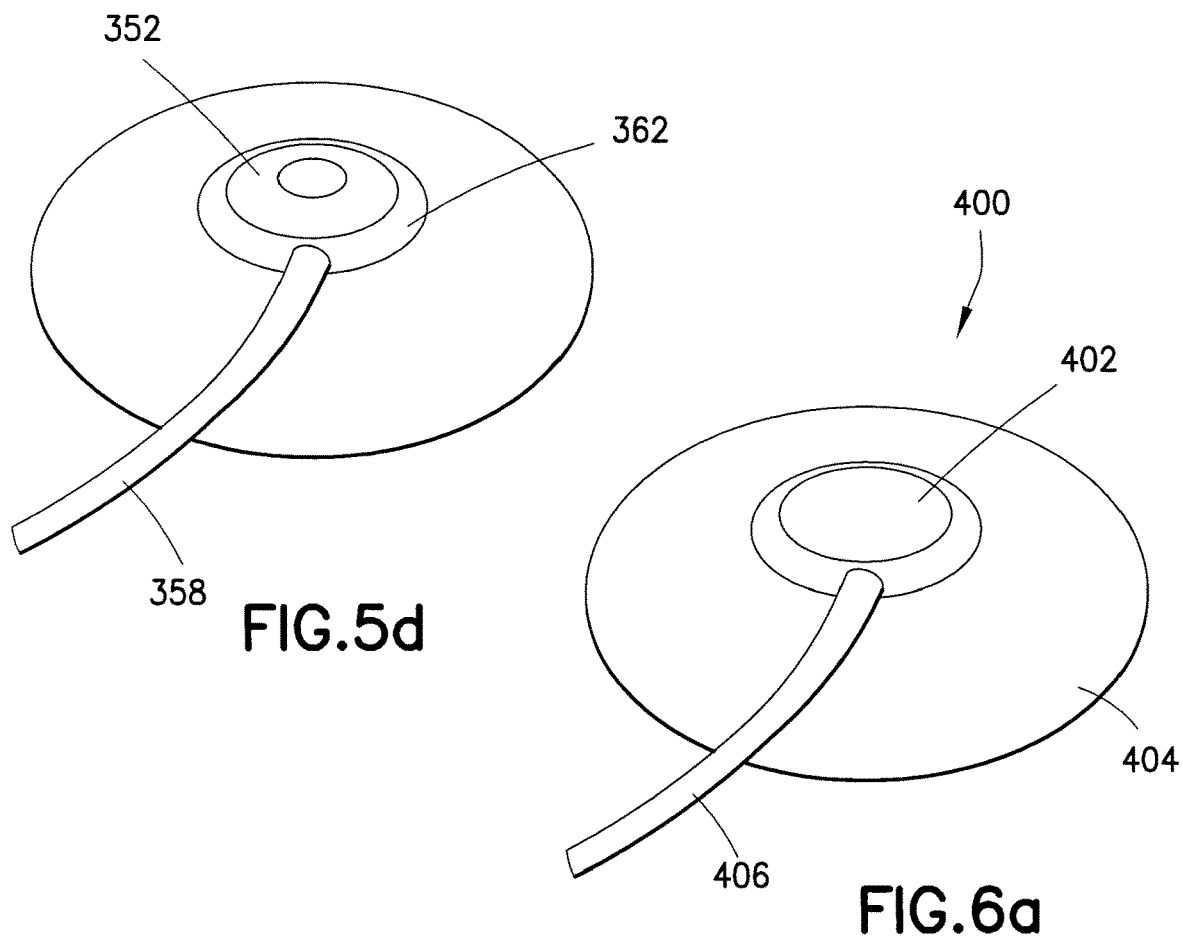
FIG.5d
FIG.6a
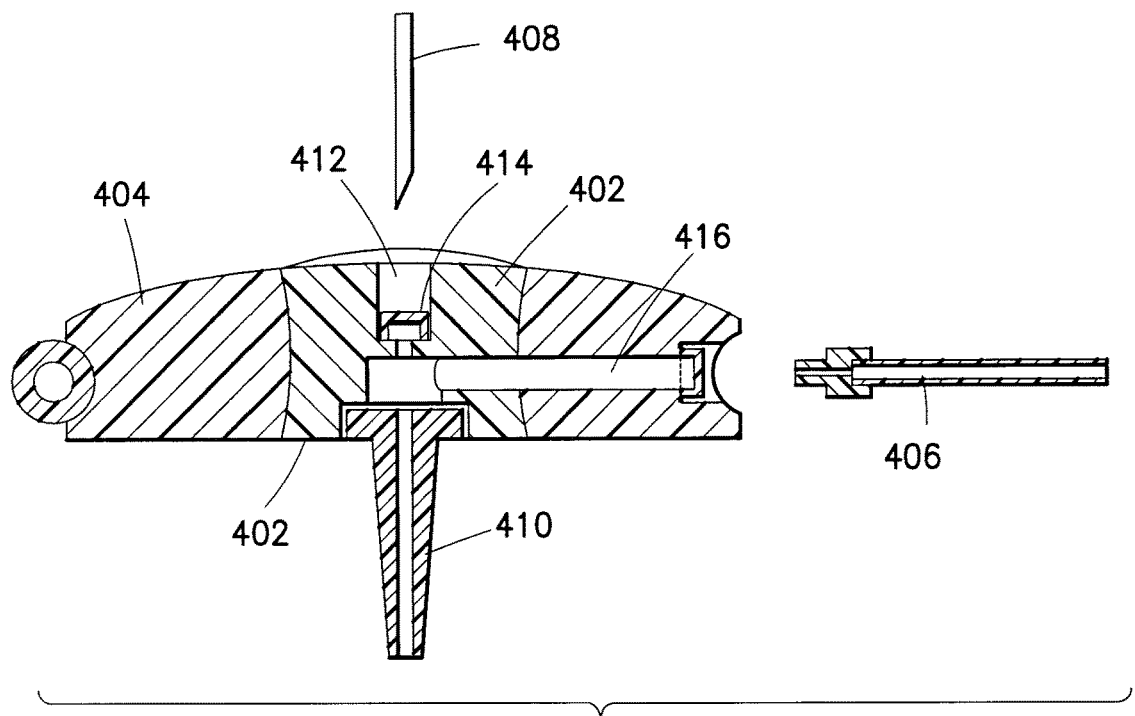
FIG.6b

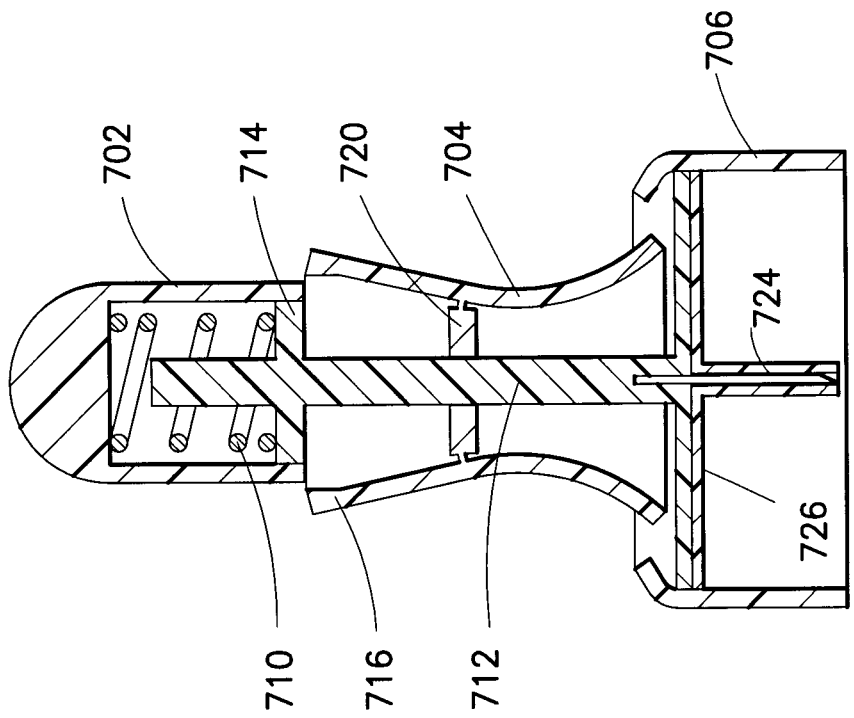
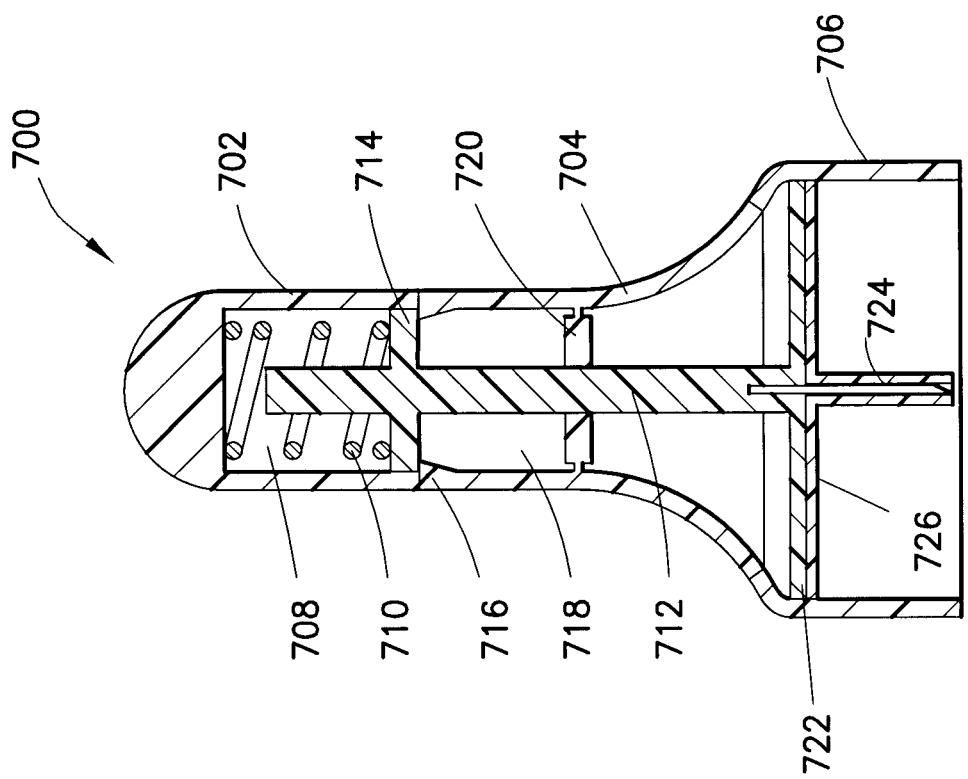

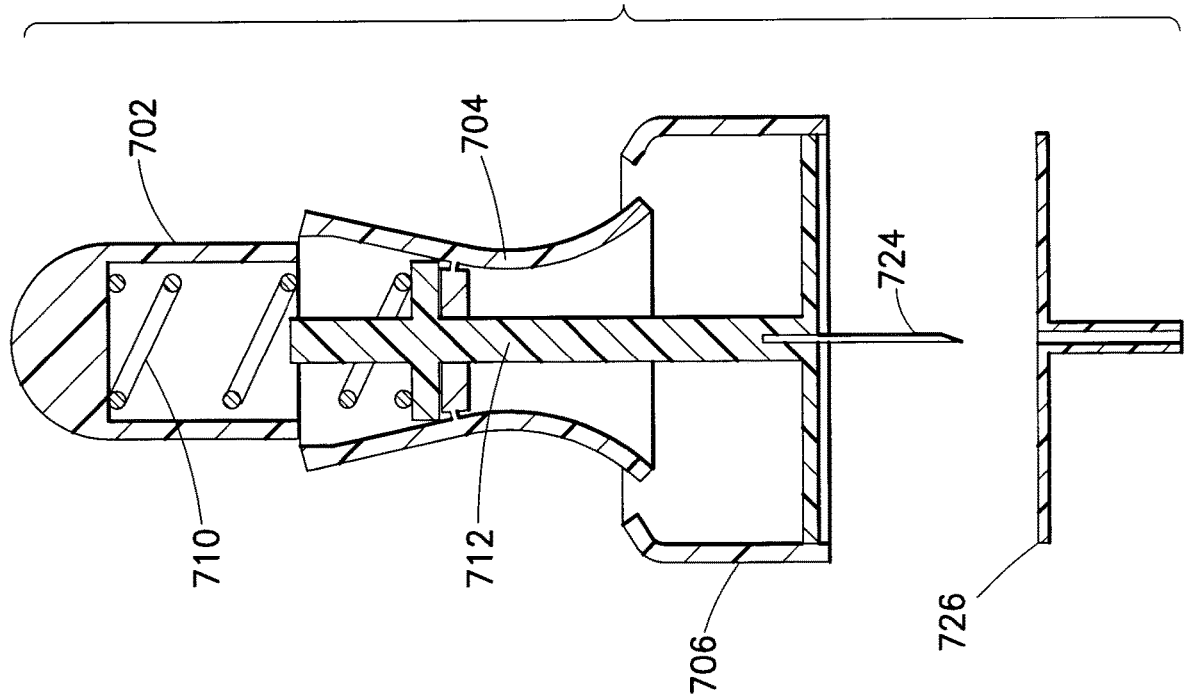
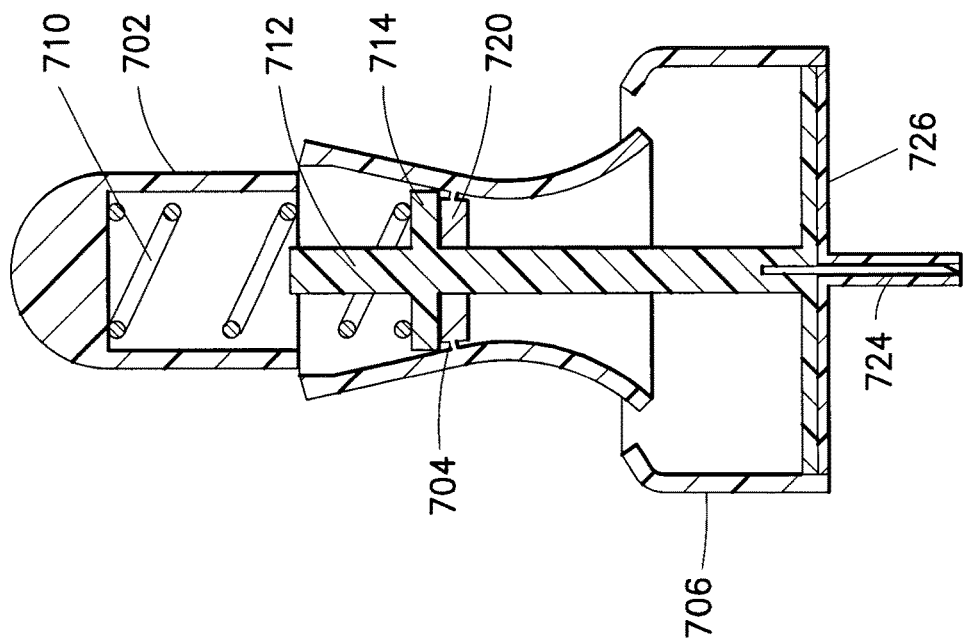
FIG. 14d
FIG. 14c

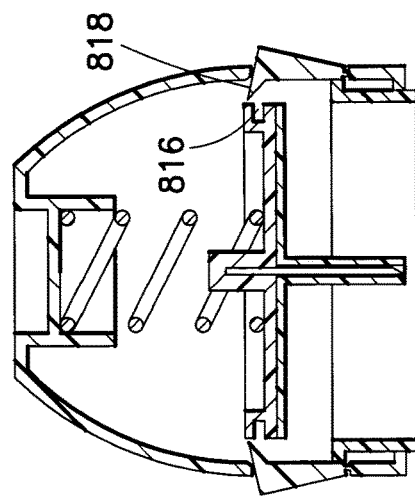
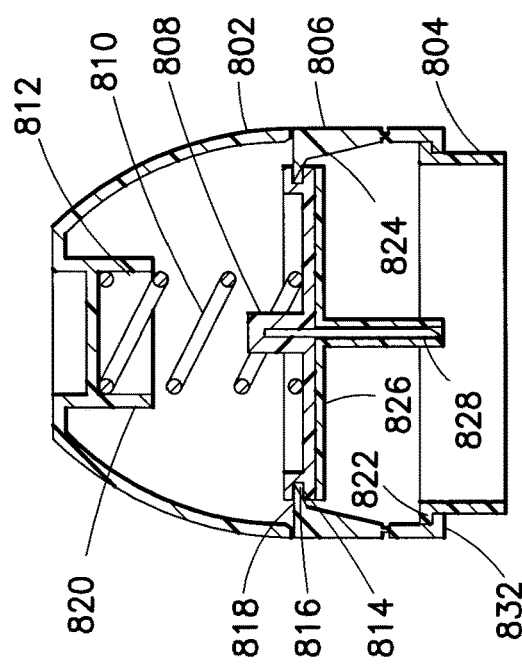
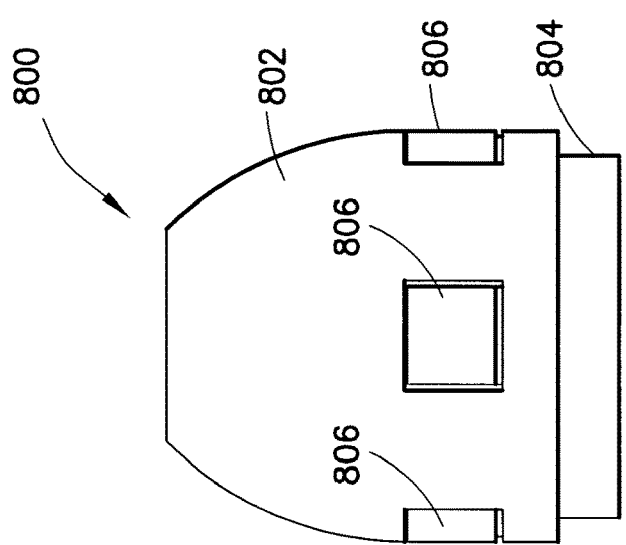
FIG. 15c
FIG. 15b
FIG. 15a

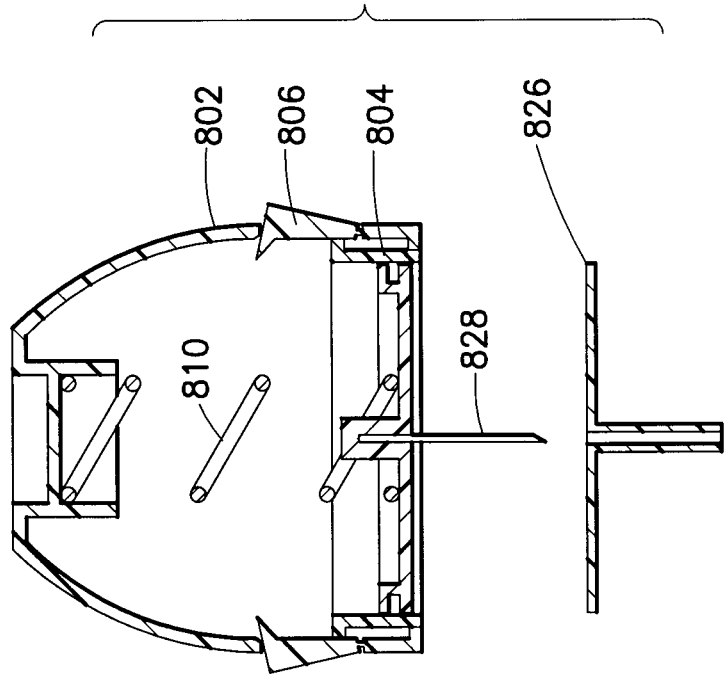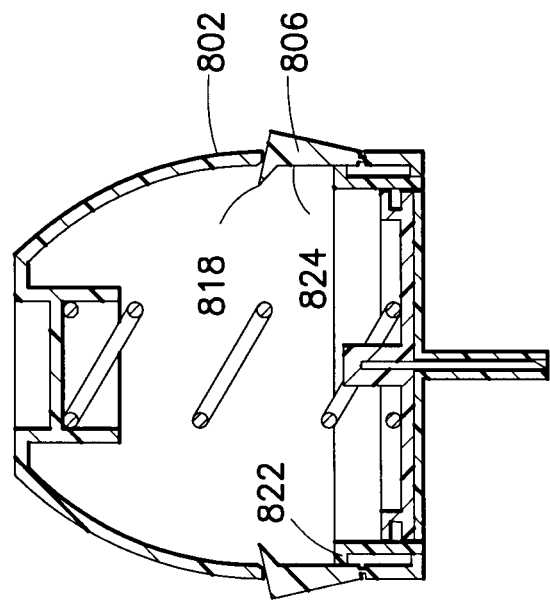

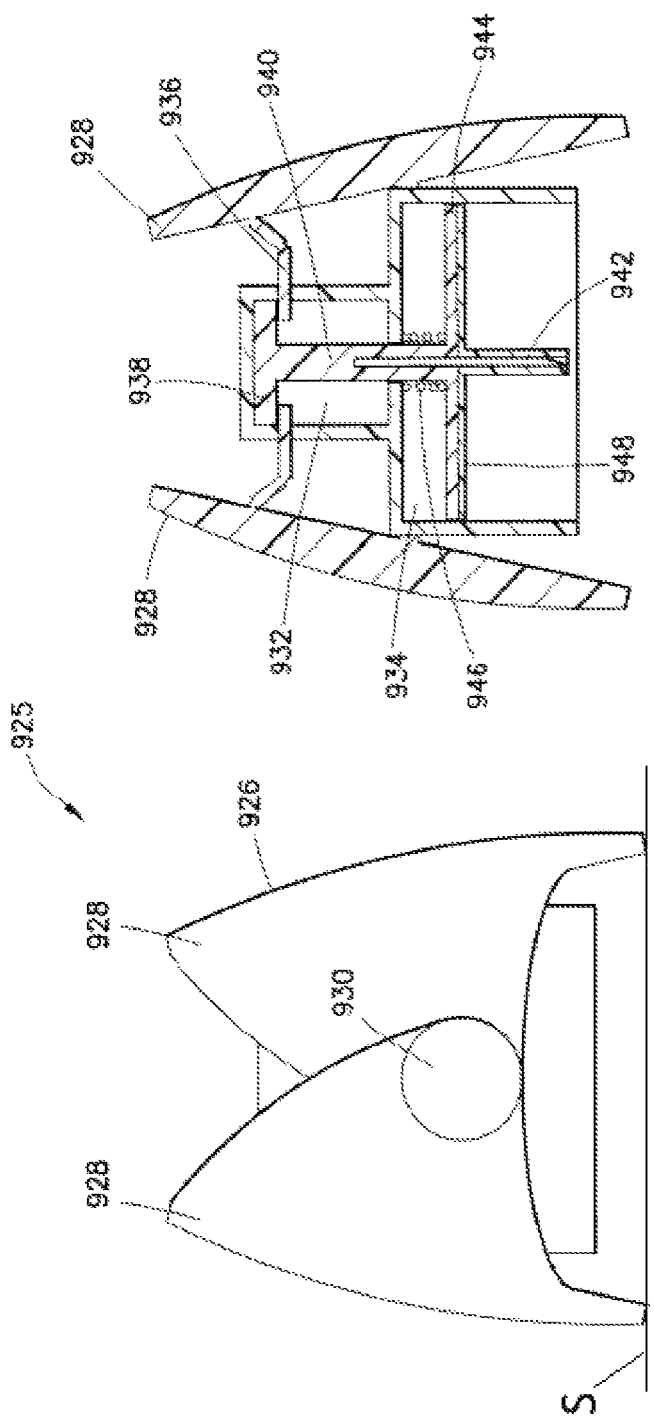

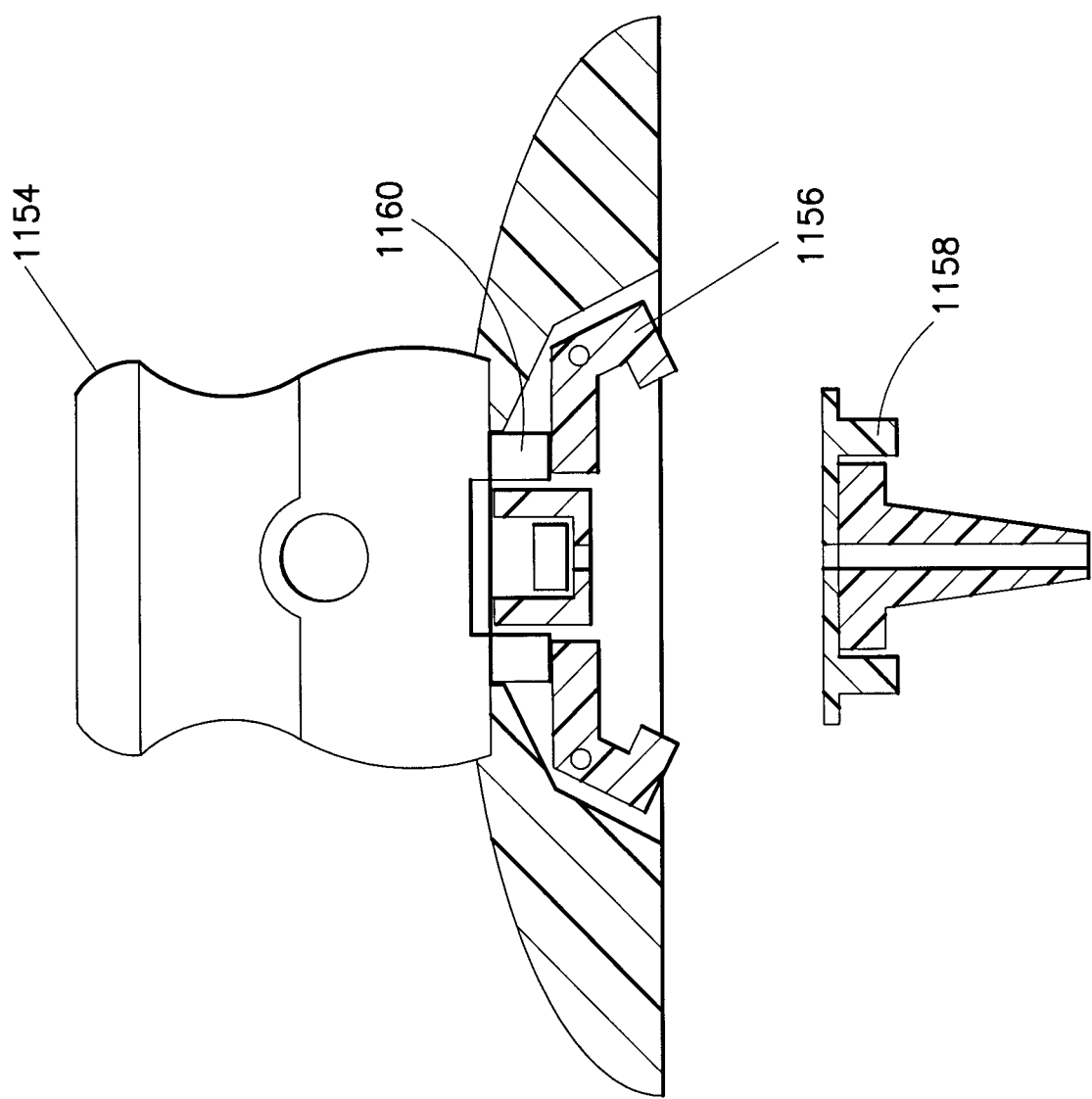

INFUSION SET

CROSS-REFERENCE TO RELATED APPLICATIONS

This application is a continuation of U.S. patent application Ser. No. 13/138,209, filed on Feb. 1, 2012, which is the U.S. national stage of international patent application No. PCT/US10/00145, filed on Jan. 21, 2010, which claims the benefit under 35 U.S.C. § 119(a) of U.S. Provisional Application No. 61/202,019, entitled "Infusion Set", filed on Jan. 21, 2009, the entire content, disclosure and subject matter of said application being expressly incorporated herein by reference.

FIELD OF THE INVENTION

The present invention relates generally to components, elements and packaging of infusion sets, including features and elements in the areas of tube management, site management, set adhesion, set insertion, set placement and changing operations and packaging.

BACKGROUND OF THE INVENTION

A large number of people, such as those suffering from conditions such as diabetes use some form of infusion therapy, such as daily insulin infusions to maintain close control of their glucose levels. Currently, in the insulin infusion treatment example, there are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

As patients on oral agents eventually move to insulin and their interest in intensive therapy increases, users typically look to these insulin pumps for improvements in the management of their condition. Therefore interest in better pump-related therapy is on the rise. In this and similar examples, what is needed to fully meet this increased interest are advanced, improved, and novel new components, elements and packaging of current and future insulin infusion sets, including features and elements in the areas of tube management, site management, set adhesion, set insertion, set placement and changing operations and packaging.

Accordingly, a need exists for such advanced, improved, and novel new components, elements and packaging of current and future infusion sets, that further provide simplicity in manufacture and use improvements for both insulin and non-insulin applications.

SUMMARY OF THE INVENTION

An object of the present invention is to substantially address the above and other concerns, and provide advanced, improved, and novel new components, elements and packaging of current and future infusion sets, that further provide simplicity in manufacture and use improvements for both insulin and non-insulin applications.

Another object of the present invention is to provide a collection of advanced, improved, and novel new components and elements in a single package to simplify assembly and use of the infusion set by the user.

Another object of the present invention is to provide an exemplary pushbutton-type inserter, squeeze-type inserter, contact-type inserter, skin pinching-type inserter, folding retraction-type inserter, and/or multistage-type inserter having at least one reusable stage, which can be provided in the single package to simplify assembly and use of the infusion set by the user.

Another object of the present invention is to provide an exemplary adhesion means with two or more user-selectable degrees of adhesion strength which can be provided in the single package to simplify assembly and use of the infusion set by the user.

Another object of the present invention is to provide an exemplary self-sealing tube connection means which can be provided in the single package to simplify assembly and use of the infusion set by the user.

Another object of the present invention is to provide an exemplary set having one or more clear and/or magnifying lens features to view a site beneath the set which can be provided in the single package to simplify assembly and use of the infusion set by the user.

Another object of the present invention is to provide an exemplary tube management element having a spring-loaded circular tube reel, tubing pull ties, elastic accordion, pouch or shortened length to manage a tube or tube loop, which can be provided in the single package to simplify assembly and use of the infusion set by the user.

Another object of the present invention is to provide an exemplary tube connection element including a tapered connector, detent connector and/or a magnetic attraction connector, which can be provided in the single package to simplify assembly and use of the infusion set by the user.

Another object of the present invention is to provide an exemplary adhesion concealment means for concealment of the set once in position and/or a decoration means for decoration of the set once in position, which can be provided in the single package to simplify assembly and use of the infusion set by the user.

Another object of the present invention is to provide an exemplary set placement guidance ring and/or one or more finger loops on the inserter to aid in set placement, which can be provided in the single package to simplify assembly and use of the infusion set by the user.

Another object of the present invention is to provide an exemplary site preparation wipe or spray which can be provided as part of the inserter, or otherwise included in the single package to simplify assembly and use of the infusion set by the user.

Another object of the present invention is to provide an exemplary package which can hold a number of sets that can be easily released and retrieved from the tray by an inserter to simplify assembly and use of the infusion set by the user.

Another object of the present invention is to provide an exemplary insertion needle handle and shroud which can be provided in the single package to simplify assembly and use of the infusion set by the user.

Another object of the present invention is to provide an exemplary squeeze-type latch between an upper portion and a lower portion of the set, and/or a tool removable upper portion of the set, which can be provided in the single package to simplify assembly and use of the infusion set by the user.

Another object of the present invention is to provide an annular fluid reservoir and/or fluid path in the set hub, which can significantly minimize the penetration distance of the tubeset connector into the hub while maintaining a sufficiently large tubeset connector geometry.

Another object of the present invention is to provide substantially closed or sealed annular fluid reservoir and/or fluid path in the set hub, which can reseal any insertion openings generated by the insertion needle, and allow penetration by a tubeset connector needle.

Another object of the present invention is to provide an infusion set constructed of a soft, pliable and/or elastic or similar material such that the infusion set is soft or pliable to a degree that allows the elasticity of the materials to affix a tube "ring" of the tubeset connector to the hub.

Another object of the present invention is to provide an infusion set constructed such that the tube ring of the tubeset connector can include the tubeset connector needle to pierce the hub, wherein the elasticity of the materials function to seal the insertion site of the tubeset connector needle.

Another object of the present invention is to provide an infusion set constructed such that the tubeset connector needle of the tube ring of the tubeset connector can pierce the hub at any rotational position, and wherein the elasticity of the materials function to seal the insertion site of the tubeset connector needle such that the tubeset connector needle of the tube ring of the tubeset connector can be withdrawn and the tube ring repositioned at a different rotational alignment position.

Another object of the present invention is to provide a catheter constructed of a body temperature softening polyurethane or similar material, and include one or more features including a splined lumen and holes or openings along a body length, including cross-drilled holes.

These and other objects are substantially achieved by providing a collection of advanced, improved, and novel new components and elements in a single package to simplify assembly and use of the infusion set by the user, including one or more of an exemplary pushbutton-type inserter, squeeze-type inserter, contact-type inserter, skin pinching-type inserter, folding retraction-type inserter, and/or multistage-type inserter having at least one reusable stage. One or more of the exemplary embodiments comprise a user gripping surface and a means to release a firing spring for set placement, and one or more retraction features to retract the insertion needle to avoid any dangers to the user and permit safe disposal. Further, one or more of the exemplary embodiments can comprise a set placement guidance ring to be placed on the insertion site and which mates with an end of the inserter to ensure that the inserter is properly positioned before release of the set. Further, one or more of the exemplary embodiments can comprise one or more finger loops extending from a body of the inserter to aid in set placement. Still further, one or more of the exemplary embodiments can comprise a squeeze-type latch between an upper portion and a lower portion of the set comprising one or more pushbuttons which articulate a latch between the upper and lower portions, thereby releasing the upper portion of the set from the lower portion which can remain in position. In yet other embodiments of the present invention, the upper portion can be configured to be tool-removable, such that the tool comprises one or more pins which are inserted into the lower portion and release a latch between the upper and lower portions, thereby releasing the upper portion of the set from the lower portion which can remain in position. Still further, one or more of the exemplary embodiments can comprise an insertion needle handle and shroud comprising one or more hinged flat members which can be bent to cover the protruding needle after use.

These and other objects are also substantially achieved by providing a collection of advanced, improved, and novel new components and elements in a single package to simplify assembly and use of the infusion set by the user, including one or more of an exemplary adhesion means with two or more user-selectable degrees of adhesion strength comprising at lease a first and second adhesion ring having different degrees of adhesive strength. The user can select which ring to use by removing a cover of the desired ring and leaving the remaining rings covered. A self-sealing tube connection means can be provided and comprise a set having a groove into which an elastic ring and tube connector can be positioned, such that the elastic ring secures the tube to the set and seals the connection between each. The set can comprise one or more clear and/or magnifying plastic components to view a site beneath the set, wherein the adhesive pad is provided with one or more clearances to allow the visual access.

These and other objects are also substantially achieved by providing a collection of advanced, improved, and novel new components and elements in a single package to simplify assembly and use of the infusion set by the user, including one or more tube management elements comprising a spring-loaded circular tube reel which serves to feed and retract excess tube as urged by a reel spring, one or more tubing pull ties which can be pulled to either secure or release tubing being stored in a large loop, an elastic accordion or pouch in which to store tubing, or provide shortened tube lengths between set and pump. Such tubing can further comprise one or more embodiments of a tube connection including a tapered connector in which a tight engagement provides connection, a detent connector in which projecting detents and recessed detents provide connection, and a magnetic connector in which magnetic attraction provides connection. Still further, an insulin supply comprising an insulin content, supply vial and tubing can be provided with the tubing and tubing connectors.

These and other objects are also substantially achieved by providing a collection of advanced, improved, and novel new components and elements in a single package to simplify assembly and use of the infusion set by the user, including one or more of an adhesion concealment means for concealment of the set once in position comprising an adhesive pad to be placed over a set to conceal the set, or a decorative adhesive pad to be placed over a set to enhance the set. A site preparation wipe comprising a disposable pad including a site preparation solution can be provided as well as an improved inserter body that comprises a spray mechanism and site preparation solution contents.

These and other objects are also substantially achieved by providing a collection of advanced, improved, and novel new components and elements in an exemplary package comprising a number of openings into which sets can be aligned and secured by a covering, such as foil, and which allows set removal by an inserter configured to pierce the foil and capture and remove the set from the tray.

BRIEF DESCRIPTION OF THE DRAWINGS

The various objects, advantages and novel features of the preferred embodiments of the present invention will be more readily appreciated from the following detailed description when read in conjunction with the appended drawings, in which:

FIGS. 3a-3e are cross-sectional views of an exemplary single-button insertion device in accordance with an exemplary embodiment of the present invention;

FIGS. 5a-5d are views of an exemplary set connection method in accordance with an exemplary embodiment of the present invention;

FIGS. 6a-6b are views of an exemplary set site inspection element in accordance with an exemplary embodiment of the present invention;

FIGS. 14a-14d are cross-sectional views of an exemplary "squeeze-type" inserter in accordance with an exemplary embodiment of the present invention;

FIGS. 15a-15e are views of an exemplary "contact-type" inserter in accordance with an exemplary embodiment of the present invention;

FIGS. 17a-17d are views of an exemplary "skin pinch-type" inserter in accordance with an exemplary embodiment of the present invention;

FIGS. 20a-20d are views of an exemplary "tool-type" latch provided as a connection method in accordance with an exemplary embodiment of the present invention;

Throughout the drawings, like reference numerals will be understood to refer to like parts, components and structures.

DETAILED DESCRIPTION OF THE EXEMPLARY EMBODIMENTS

Figure 1:
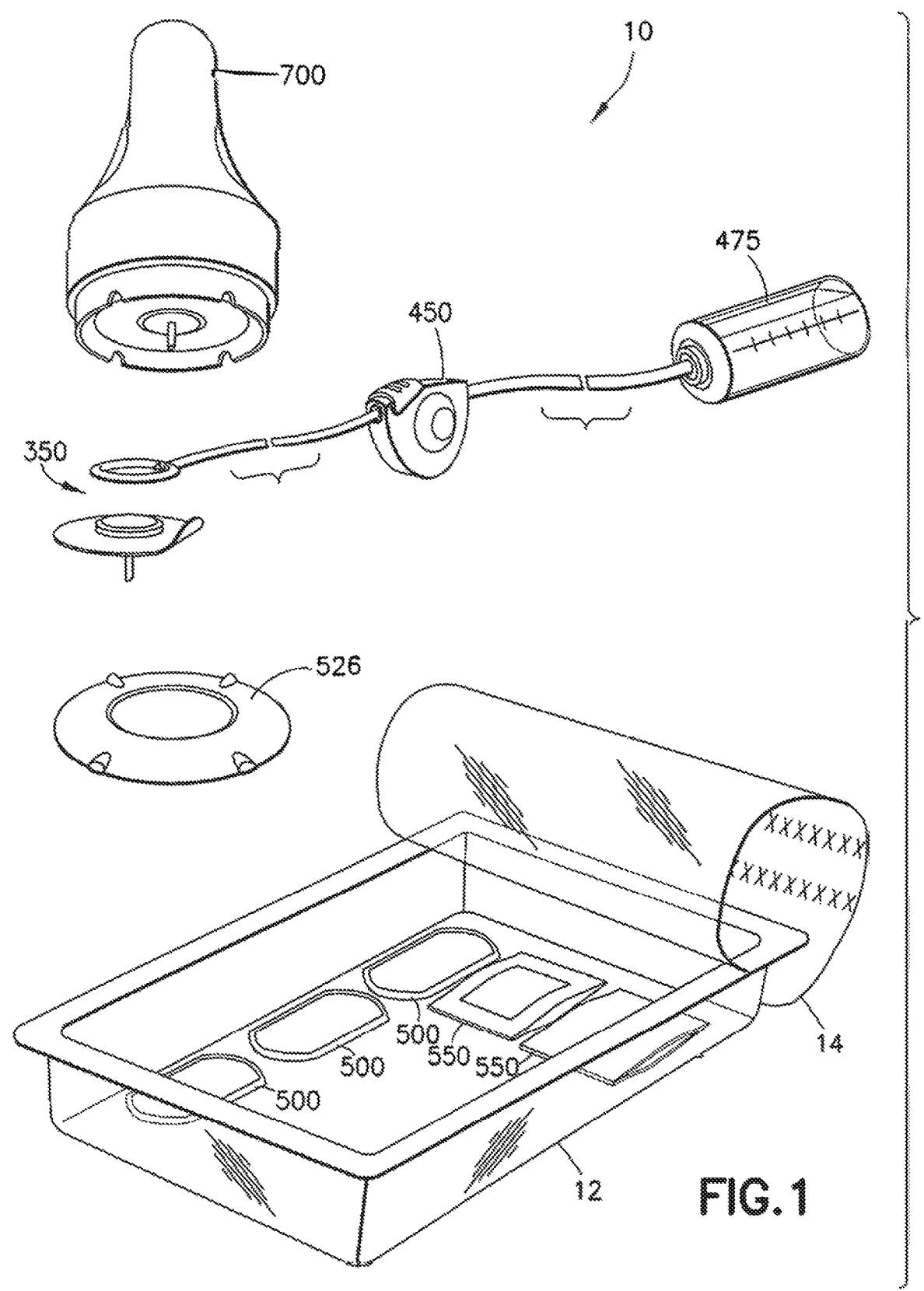
FIGS. 1 and 2 are perspective views of a collection of infusion set elements and associated packaging in accordance with an exemplary embodiment of the present invention.

The embodiments of the present device described below illustrate a number of advanced, improved, and novel new components, elements and packaging of current and future infusion sets, that further provide simplicity in manufacture and use improvements for both insulin and non-insulin applications. Exemplary embodiments are presented in separate descriptions, although the individual features of these embodiments can be combined in any number of ways to meet the needs of the user.

As will be appreciated by one skilled in the art, there are numerous ways of carrying out the examples, improvements and arrangements of insulin-associated devices disclosed herein. Although reference will be made to the embodiments depicted in the drawings and the following descriptions, the embodiments disclosed herein are not meant to be exhaustive of the various alternative designs and embodiments that are encompassed by the disclosed invention.

Figure 2:
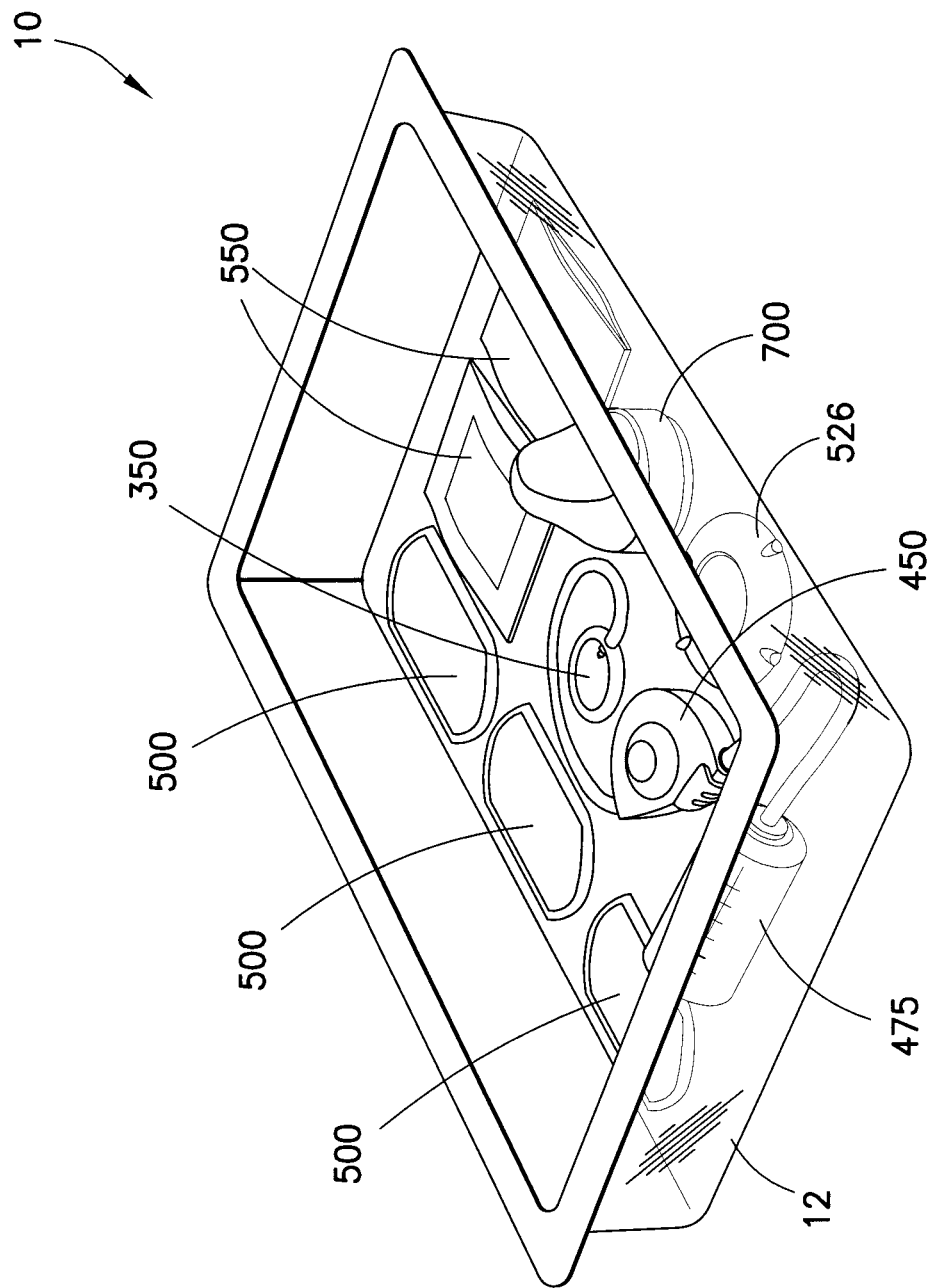

The embodiments of the present device described below illustrate a number of features and elements in the areas of tube management, site management, set adhesion, set insertion, set placement and changing operations and packaging. A collection of exemplary embodiments of the present invention is shown by way of example in FIGS. 1 and 2, which serve to introduce elements described in greater detail below. FIG. 1 illustrates an exemplary infusion set 10 including the following features. As shown in FIG. 1, an exemplary infusion set can comprise an inserter, such as the squeeze-type inserter 700 for use with a set, such as the ring-sealed set 350. A tube and associated tube management devices, such as the circular reel 450, can be provided for communication with an insulin pump (not shown) or with an insulin supply, such as the insulin supply 475. A placement assistance element can be provided, such as the placement assistance ring 526, and the entire arrangement can be placed into a sealed tray 12 with a number of site preparation elements, such as the pads 550, and site concealment elements, such as the pads 500. The tray can be comprised of any suitable plastic, fiber or composite material compatible with the components, and can provide compartments, padding or element securing detents or moldings. The set can be packaged in the tray 12 and sealed with a clear and/or labeled cover 14, and includes every component needed to position, connect, insert, and wear the set, as well as the insulin 475 itself as shown in FIG. 2. Each of the exemplary components, including a number of additional or alternate components, will now be described individually in greater detail.

An exemplary embodiment of the present invention can be provided with an insertion device as desired by a user. An exemplary insertion device 100 is shown in FIGS. 3a-3e. The exemplary insertion device of FIGS. 3a-3e provides an insertion device which can contain the set at an open, patient-contacting end, and provide an actuation button at an opposite end. Upon activation, the insertion device places the set and automatically retracts the insertion needle back into the insertion device.

As shown in FIG. 3a, the insertion device can comprise a substantially cylindrical housing 102 from which a spring biased projection or pushbutton 104 can extend, and in which a set 106 can be positioned for use. The housing 102 can have a first diameter at a lower portion thereof in which the set 106 can be positioned, and transition to a reduced second diameter at an opposite end to substantially equal a diameter of the pushbutton 104.

Within the body of the housing 102, a number of elements are contained which serve to fire the set 106 into position, and then retract the insertion needle. To do so, the housing 102 comprises a first, second and third chamber 108, 110 and 112 of different widths. The first chamber 108 at an uppermost portion of the housing 102 has a width sufficient to slidably receive an end of an inserter rod 114. At an upper end of the first chamber 108, an opening is provided though which the pushbutton 104 slidably enters the first chamber 108, and a lower end of the first chamber opens to create the second chamber 110 as described in greater detail below. The first chamber further comprises at least one inclined detent 116 disposed upon an inner wall of the first chamber 108 which serves to capture and secure a similar, deflectable detent 118 at an upper end of the inserter rod 114. One or more further similar, deflectable detents 120 are disposed upon an end 122 of the pushbutton 104 within the first chamber 108. The end 122 of the pushbutton 104 is provided to have a width substantially equal to the width of the first chamber 108 to align and guide the pushbutton 104 during operation. A spring 124 is disposed concentrically with the pushbutton 104 and is captured between an outer surface of the housing 102 and an expanded head of the pushbutton 104 to constantly urge the pushbutton 104 upward.

As noted above, the pushbutton 104 comprises an end 122 with one or more inclined detents 120. When pressed downward, the inclined detents 120 come into contact with the inclined detents 118 of the inserter rod 114 which are being held by the detents 116 of the first chamber 108. The contact releases the detents 118 and allows the inserter rod 114 to be urged downward by a firing spring 126 disposed within the second chamber 110 of the housing 102.

The second chamber 110 has a width wider than that of the first chamber 108, which is sufficient to slidably receive the inserter rod 114 and more specifically, a width sufficient to slidably contain planar members 128 and 132 of the inserter rod 114.

The firing spring 126 is disposed concentrically with the inserter rod 114 about an outer circumference of the inserter rod body as captured within the second chamber 110. That is, the firing spring 126 is captured within the second chamber 110 of the housing 102 between an upper wall of the second chamber 110, and the upper surface of the planar member 128 of the inserter rod 114. In doing so, the firing spring 126 constantly urges the inserter rod 114 downward.

At a lower portion of the housing 102, the third chamber 112 can be provided having a width wider than that of the second chamber 110, thereby creating a shoulder 130 therebetween. As described in greater detail below, the shoulder 130 is configured to allow downward travel of the inserter rod 114 and capture one or more detents on an outer surface of the inserter rod 114 to prevent retraction of the inserter rod 114, yet permit full retraction of a needle carrier and inserter needle.

As noted above, the inserter rod 114 is configured to slidably travel though each of the first, second and third chambers 108, 110, and 112, of the housing 102. The inserter rod 114 is substantially cylindrical and comprises a diameter at an upper portion substantially equal to the width of the first chamber 108 to be directed and guided by the first chamber 108 during use. A lower portion of the inserter rod 114 comprises the first and second planar members 128 and 132, which comprise a diameter substantially equal to the width of the second chamber 110 to be directed and guided by the second chamber during use.

As noted above, the inserter rod 114 comprises the first and second planar members 128 and 132. The inserter rod 114 further comprises an inserter needle guide 144 and at least third and fourth elements 136 and 138 extending between the first and second planar members 128 and 132. A spring 140 is captured between the needle guide 144 and fourth element 138, and passes through an opening in the third element 136, to constantly urge both the third and fourth elements 136 and 138 outward from a center axis of the insertion device, and against an inner wall of the second and third chambers 110 and 112. The fourth element 138 comprises an inclined detent 142 which is urged against the inner wall of the second and third chambers 110 and 112. In doing so, as the inserter rod 114 is urged downward and the detent 142 passes the shoulder 130, the spring 140 urges the element 138 against the inner wall of the third chamber 112 such that the detent 142 is captured by the shoulder 130 and prevents the retraction of the inserter rod 114 as shown in FIGS. 3c and 3d. The needle carrier and inserter needle are permitted to retract as described in greater detail below.

The third element 136 comprises at least one projection 146 which is configured to capture a groove 154 in the needle carrier 148 slidably disposed within an inner opening of the inserter rod 114. The needle carrier 148 secures the inserter needle 134 at a lower end, such that the inserter needle extends through the needle guide 144 and though an opening in the planar member 132 of the inserter rod 114. The needle carrier 148 further comprises the groove 154 which can be captured by the projection 146. The remainder of the needle carrier 148 extends through the planar member 128 and into the inner opening of the inserter rod 114 and terminates at a planar end 150. The planar end 150 of the needle carrier 148 has a width substantially the same as the width of the inner opening of the inserter rod 114 to align and guide the needle carrier 148 during retraction. A retraction spring 152 is captured between the planar end 150 of the needle carrier 148 and the planar member 128 of the inserter rod 114. In doing so, the retraction spring 152 constantly urges the needle carrier 148 upward.

While in the pre-use position, a large portion of the second chamber 110 remains open to the end of the device. In doing so, the set 106 can be positioned on the extended needle 134, at an opposite side of the second planar member 132 of the inserter rod 114. The set 106 can be gently held within the second chamber 110 through contact with the walls of the chamber, and/or through contact with the inserter needle 134. As noted elsewhere, the set 106 can include any number or configurations of adhesive pads (not shown) and other connection features, which can be accommodated by the insertion device 100.

As shown in FIGS. 3a-3e, the compression of the push button 104 releases the inclined detents 118 of the inserter rod 114 as shown in FIG. 3a, permitting the firing spring 126 to drive the needle 134, set 106, and adhesive pad into the region of the skin beneath the third chamber 112 of the device as shown in FIG. 3b, and also releases the spring 140 to lock the inserter rod 114 in the extended position as shown in FIG. 3c. That is, upon release, the inserter rod 114 is free to travel downward as urged by the trapped spring 126. In doing so, the inserter rod 114, including its end 132 and needle 134 travel downward through the third chamber 112, urging the set 106 downward with it. At or before reaching the travel limit of the inserter rod 114, the set 106 is positioned, retraction of the needle carrier 148 and needle 134 occurs, and the device can be removed as shown in FIG. 3d, thereby leaving the set 106 at the desired insertion site as shown in FIG. 3e.

To retract the needle carrier 148 and needle 134, no user action is required. As shown in FIGS. 3c-3d, the shoulder 130 serves to hold the inserter rod 114 in the down position. When the insertion is completed and the inserter rod 114 is captured in the down position by the outward movement of members 136 and 138, the movement simultaneously releases the needle carrier 148 and needle 134, and allows the needle carrier 148 and needle 134 to retract upward as urged by the retraction spring 152 as shown in FIGS. 3c and 3d. The needle carrier 148 and needle 134 are retracted until contacting an upper stop 156 disposed at an upper end of the inserter rod 114.

The insertion device 100 of FIGS. 3a-3e uses the single button press of the pushbutton 104 to release the firing mechanism, insert the set 106, and safely retract the needle 134 after insertion. The insertion device 100 is packaged and stored with the firing mechanism in an upright and locked position, with the firing spring 126 compressed as shown. The inserter rod 114 has the flexible wedge-shaped tabs or latches 120 at the top of it, which are locked into grooves or captured by the detents 116 at the interior top of the inserter's body 102 as shown in FIG. 3a.

Pressing the activation button 104 unlatches the firing tabs at the top of the unit as shown in FIG. 3b, and permits the firing spring 126 to extend toward its free length, propelling the needle carrier assembly 148 of the inserter rod 114 downward as shown in FIG. 3c. Upon reaching the wider region of the body interior shaft at the third chamber 112, the two spring-loaded locking halves or members 136 and 138 of the needle carrier assembly 148 move outward and lock the firing mechanism in the down position as shown in FIG. 3d, and frees the central portion of the needle carrier assembly 148 to move upward as shown in FIG. 3e, leaving the remainder of the inserter rod 114 in the down position.

By this time, the needle 134 has pierced the skin and placed the cannula and set 106, adhering it to the skin. Having been decoupled from the inserter rod 114 which has been driven downward and locked, the needle carrier assembly 148 is now free to rebound, propelled upward by the retraction spring 152 as shown in FIG. 3e. After retracting fully upward, the needle 134 is stored permanently and inaccessibly inside the insertion device housing 102, and the device is inert.

In this and other inserter embodiments described below, the inserter body and elements can be constructed of any suitable and compatible materials such as plastic or metal. Springs can be provided as coil springs made of plastic or metal, although embodiments of the present invention are not limited thereto, and other spring or biasing means can be used, such as leaf spring or simply material resiliency. The insertion needle can comprise any suitable set insertion needle of metal or plastic, having length, thickness, and bevel dimensions suitable for set insertion.

Figure 4A:
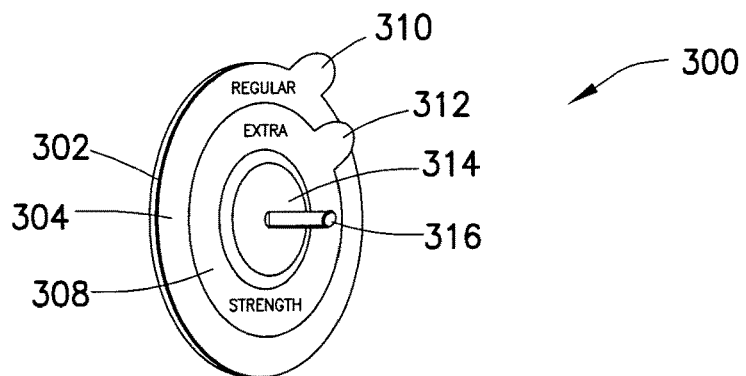
FIGS. 4a-4c are perspective views of exemplary set adhesion elements in accordance with an exemplary embodiment of the present invention.
Figure 4B:
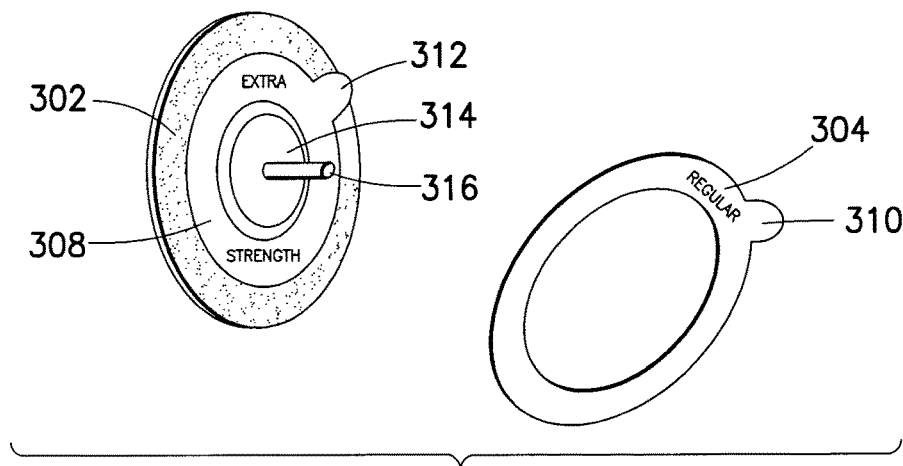
Figure 4C:
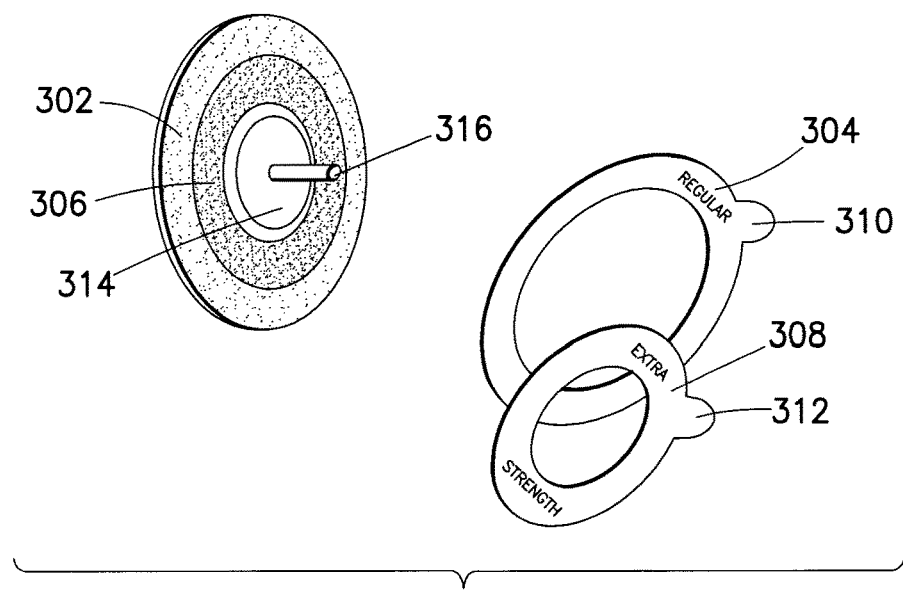

One or more of the exemplary embodiments of the present invention described herein can be further provided with additional features or elements to manage the degree of adhesion of the device in some manner as desired by a user. As shown by way of example, adhesion management elements 300 are shown in FIGS. 4a-4c. As shown in FIGS. 4a-4c, a set 314 and catheter 316 are shown encircled by concentric rings of adhesive 302 and 306. In an exemplary embodiment of the present invention, one ring can provide an adhesive with a higher degree of adhesion strength, and another ring can provide an adhesive with a lesser degree of adhesion strength, thereby allowing a user to tailor the degree of set adhesion to the user's activity plans. Although only two concentric rings of varied adhesive are shown in FIGS. 4a-4c, in yet other embodiments of the present invention, more rings can be provided, or the rings may be provided in alternate, non-circular shapes (i.e., such as oval shapes). Further, in the exemplary embodiment shown in FIGS. 4a-4c, the inner ring 306 is provided with the adhesive with a higher degree of adhesion strength and the outer ring 302 is provided with the adhesive with a lesser degree of adhesion strength, but embodiments of the present invention are not limited thereto. In yet other embodiments of the present invention, the order can be reversed or additional rings of adhesive provided.

As noted by those skilled in the art, a set typically requires a degree of adhesion to maintain proper positioning of the device. Accordingly, the exemplary embodiments of the present invention provide a set that comprises an adhesive pad or patch on the underside with a user-configurable adhesion mechanism to adapt the set to the expected environment in which it will be worn. As shown in FIG. 4a, the adhesive pad or patch can be provided in two or more, selectable strengths which can be variably exposed and utilized depending on the user's preference. A region of basic adhesive 302 having a removable cover 304 segmented from other covers, can be used for everyday needs while the region of extra-strong adhesive 306 remains covered by a similar segmented cover 308 as shown in FIG. 4b. The region of extra-strong adhesive 306 can be exposed by the removal of the cover 308 if athletic activities might be expected to stress the set adhesion as shown in FIG. 4c. To further simplify use, each cover 304 and 308 of each region can comprise a tab 310 and 312, respectively, to aid in removal of each adhesive cover. The covers 304 and 308 can also be labeled, color-coded or textured to show the adhesive strength thereunder.

One or more of the exemplary embodiments of the present invention described herein can be further provided with additional features or elements to provide a simple but effective connection system as desired by a user. As shown by way of example, such a connection method 350 is shown in FIGS. 5a-5d.

Figure 5A:
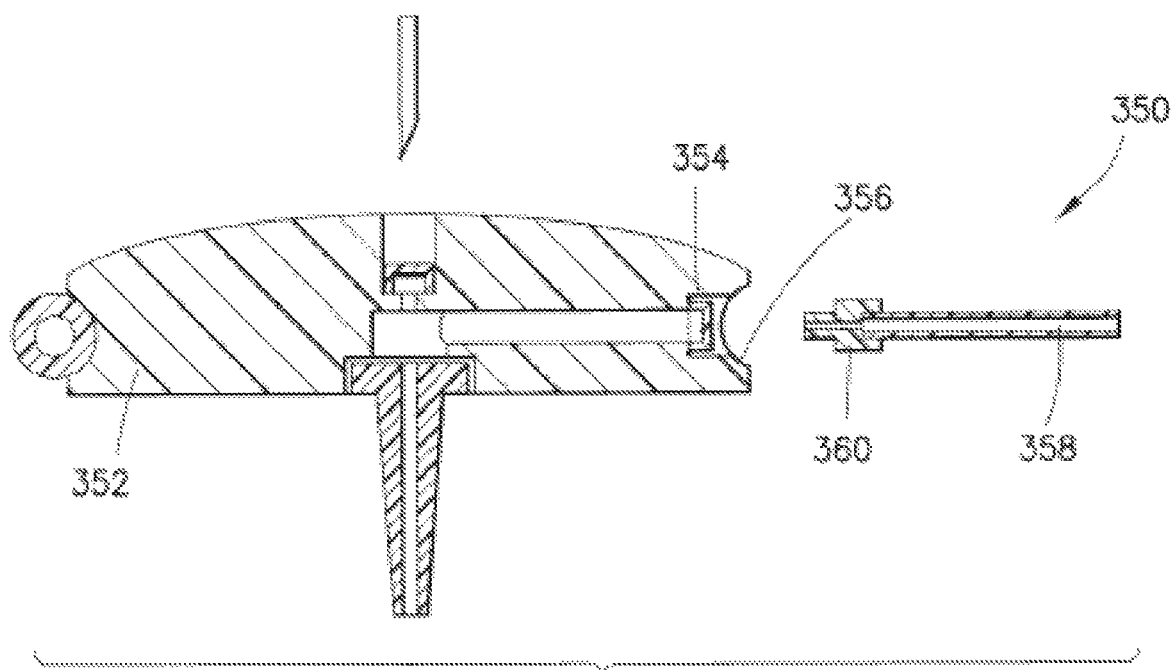
Figure 5B:
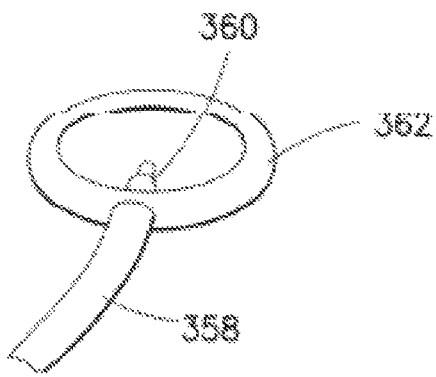

In such an exemplary embodiment, a set 352, once placed, has a port 354 that should be able to be easily connected and disconnected with a tubing 358 leading to an insulin pump (359). To do so, the set 352 can comprise the "self-sealing" connection port 354 on the outer, circular perimeter of the set 352, within a circumferential groove 356 on the body of the set 352 as shown in FIG. 5a. An incoming tube 358 can comprise a fitting 360 at the end designed to securely fit into and seal with the port 354 on the set 352, using the assistance of a flexible, resilient ring 362 extending outward from it as shown in FIG. 5b.

Figure 5C:
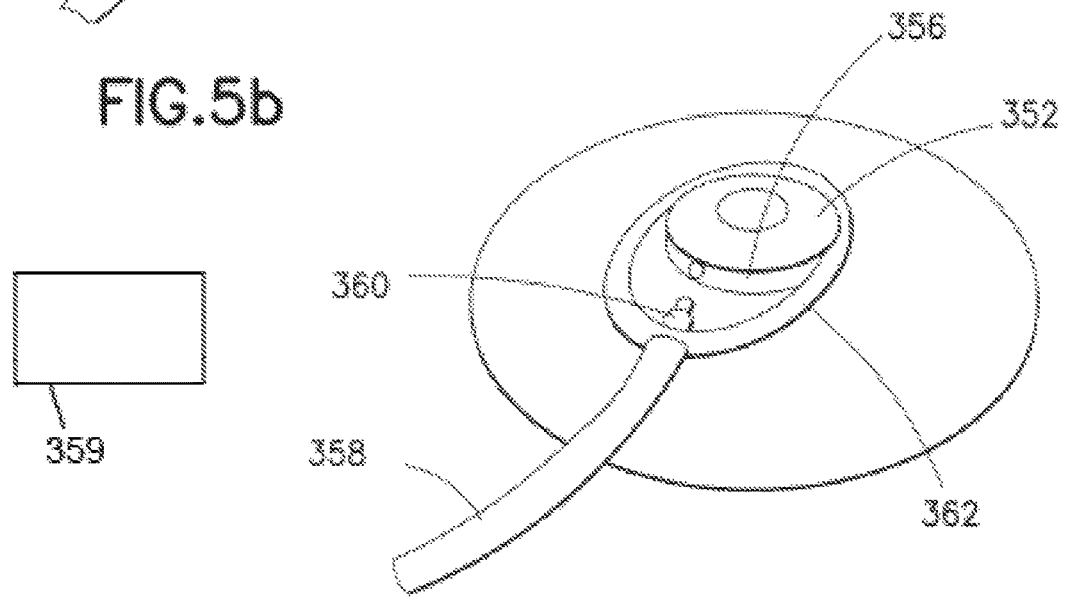

Connection of the tube 358 to the set 352 can then be accomplished by stretching the ring 362 around the far side of the set 352 as guided by the groove 356 to a first diameter to allow placement, then placing the connection fitting 360 into the port 354 as shown, and allowing the elastic ring 362 to contract to a second diameter to retain it securely as shown in FIGS. 5c and 5d. The tube, set and connectors can be constructed of any suitable material as described herein, and the ring 362 can be constructed of any compatible, resilient material which can be easily molded into the desired shape and maintain elasticity at least for an expected shelf life of the device. In a similar manner, the exemplary embodiment of the present invention shown in FIGS. 29a-29c, described in greater detail below, comprises an infusion set constructed of a soft, pliable and/or elastic or similar material such that the infusion set is soft or pliable to a degree that allows the elasticity of the materials to affix the tube ring of the tubeset connector to the hub in any number of rotational positions and which further includes a tubeset connector needle to pierce the hub, wherein the elasticity of the materials function to seal the insertion site of the tubeset connector needle.

One or more of the exemplary embodiments of the present invention described herein can be further provided with additional features or elements to allow site inspection in some manner as desired by a user. As shown by way of example, a site inspection embodiment 400 is shown in FIGS. 6a-6b. As shown in FIGS. 6a-6b, a set 404 and its housing can include a means to inspect the region of the skin immediately surrounding the insertion point, to ensure that the site is in good condition. In an exemplary embodiment of the present invention, the set 404 can include an element 402 extending from a top surface to a bottom surface of the set 404 at some point near the insertion site. As shown in FIGS. 6a-6b, the element 402 completely encircles the site, but embodiments of the present invention are not limited thereto. In yet other embodiments of the present invention, the element 402 can be provided over a narrower portion, but still sufficient to view the site from above the device.

The element 402 can be constructed of any suitable material that can be easily manufactured, bonded with the remaining elements of the set 404, provide compatibility with the contents or other materials, including the skin surface, and provide a degree of visibility between the top and bottom surfaces of the set 404. As shown in FIG. 6b, the sides of the element 402 can be configured, contoured or otherwise provided with features to be held in place by the body of the set 404, and a top surface can be contoured to add a degree of magnification. For example, the housing of the set 404 or the top surface of the element 402 can include or comprise a clear plastic magnifying element that allows for even better site inspection abilities.

Further, the element 402 can be provided with an upper surface opening 412 to secure a septum 414 and for insertion of a placement needle 408 into a catheter 410. The element 402 can further provide an opening 416 to facilitate introduction of the infusion substance through the tubing 406. Still further, where the lower surface of the set 404 is provided with an adhesive pad (not shown) at the base of the set 404, the adhesive pad can include a cutaway portion to permit visibility through the element 402.

Figure 7A:
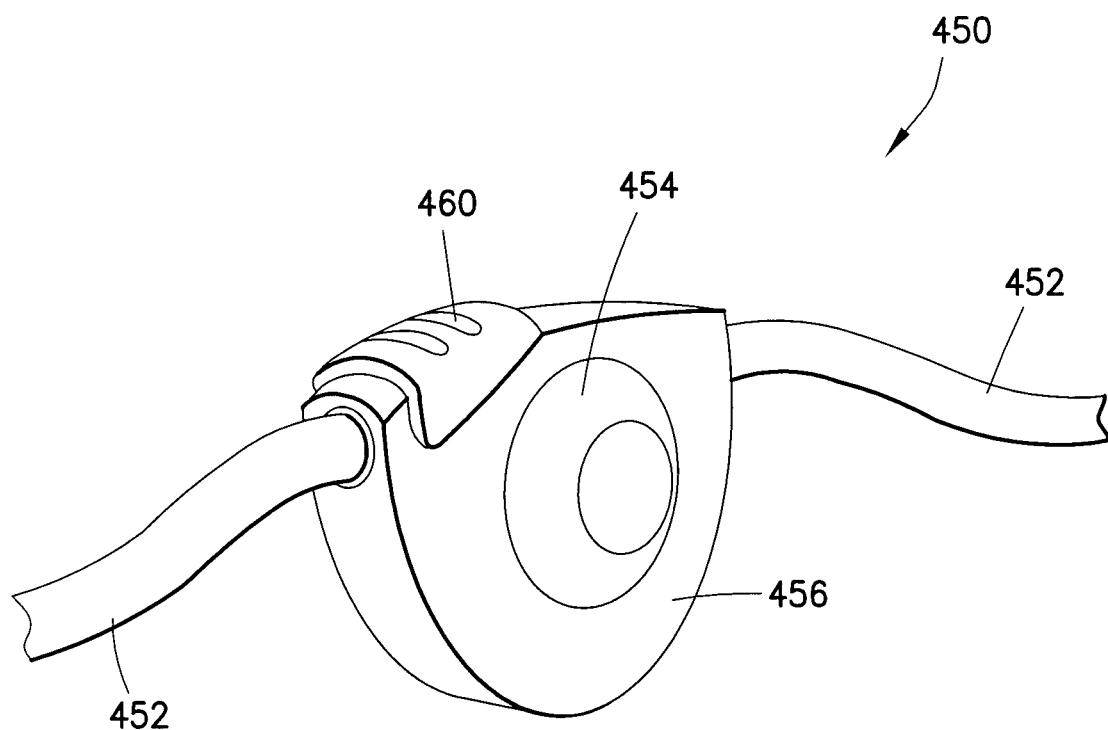
FIGS. 7a-7b are views of an exemplary set tubing management element in accordance with an exemplary embodiment of the present invention.
Figure 7B:
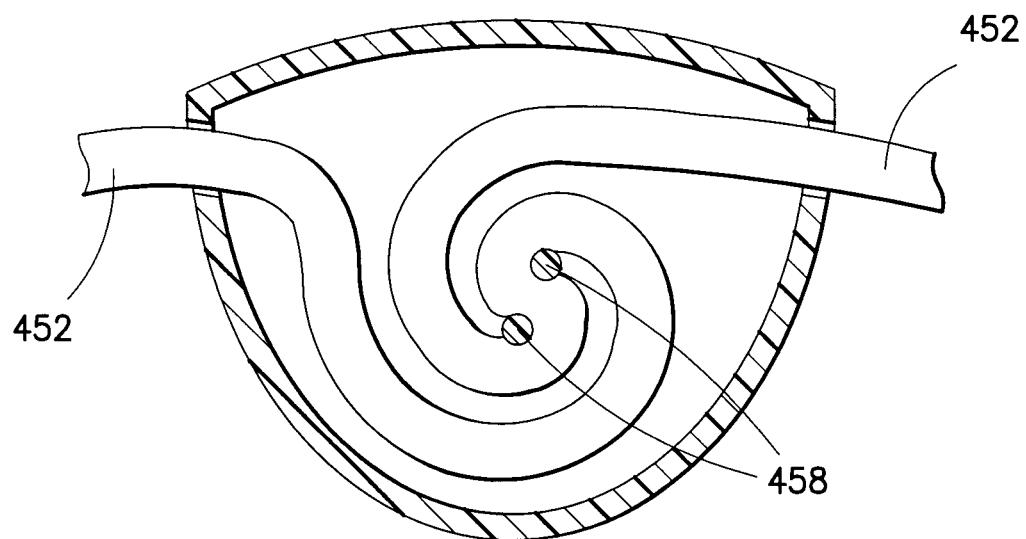

One or more of the exemplary embodiments of the present invention described herein can be further provided with additional features or elements to secure, contain, and/or conceal the tubing of the device in some manner as desired by a user. As shown by way of example, a tube management reel 450 is shown in FIGS. 7a-7b. The tubing 452 connecting the insulin supply and pump (not shown) to the infusion set (not shown) can be packaged on a spring-loaded circular reel 454 disposed within or at one side of a reel housing 456.

As shown in the cross-sectional view of FIG. 7b, the tubing 452 can enter and exit the housing 456 at opposite sides near an upper surface, and wrap about a spring mechanism using pins 458. The construction of a spring-loaded circular reel is known to those skilled in the art, so additional features of which are omitted for clarity. However, the circular reel is provided with pins 458 between which the tube 452 is secured within the housing 456 such that, feeding tubing from the housing results in the circular reel being wound tighter, and feeding tubing into the housing results in the circular reel being unwound and relaxed. Accordingly, the circular reel and pins maintain a tension on the tube 452 urging the tubing into the housing.

The circular reel can further comprise a catch/latch mechanism as known to those skilled in the art such that pulling the tube 452 a first time feeds a length of tube and a catch is provided to prevent a reverse spring-urged action. Upon pulling the tube 452 a second time, the catch can be released so that the reverse spring-urged action is released to urge the tube 452 back into the housing 456. In doing so, the reel device allows slack tubing to be fed out precisely, with spring resistance maintaining the excess tubing rolled up and stored. The locking switch or latch can be provided to allow the user to prevent inadvertent retraction or extension once a satisfactory length of tubing has been deployed. The device can further comprise a switch 460 to actuate the tube retrieval.

Figure 8:
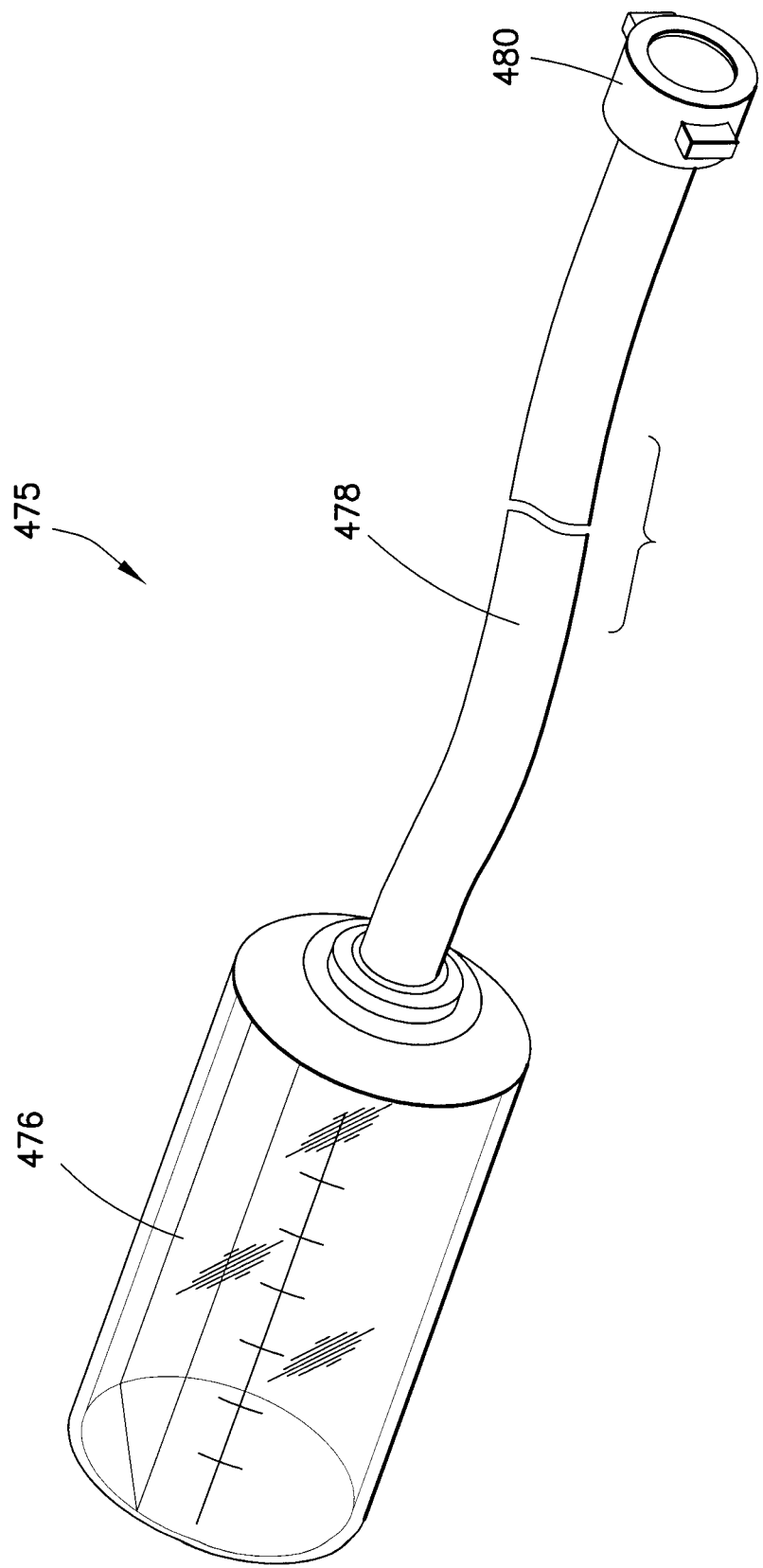
FIG. 8 is a perspective view of an alternate insulin supply and associated tubing in accordance with an exemplary embodiment of the present invention.

One or more of the exemplary embodiments of the present invention described herein can be further provided with additional features or elements to provide an insulin supply in some manner as desired by a user. As shown by way of example, an insulin supply 475 is shown in FIG. 8. FIG. 8 illustrates an exemplary embodiment of an insulin container 476 and associated tubing 478, including a tubing connection means 480. The insulin supply 476 can be packaged in a small, sealed or sealable container that is pre-connected to a length of tubing 478. The insulin container 476 can be integrated with a pump mechanism (not shown) externally via an installation process which the user can easily perform. The insulin container 476 and tubing 478, once connected to a set and pump, form a system that does not need to be primed for proper function.

The insulin container 476 can be constructed of any suitable material, such as glass or plastic, to be clear to show the contents, or non-clear or opaque to protect contents from light. The container 476 can further include incremental dosage measurement marks along one or more surfaces for use during content delivery. The associated tubing 478 and connection means 480 can be constructed of any suitable material, such as rubber, to provide flexibility and compatibility with the contents. The connection means 480 can be constructed in any number of ways, for example, including the connection means described in greater detail below in regard to FIGS. 22a-22c.

Figure 9A:
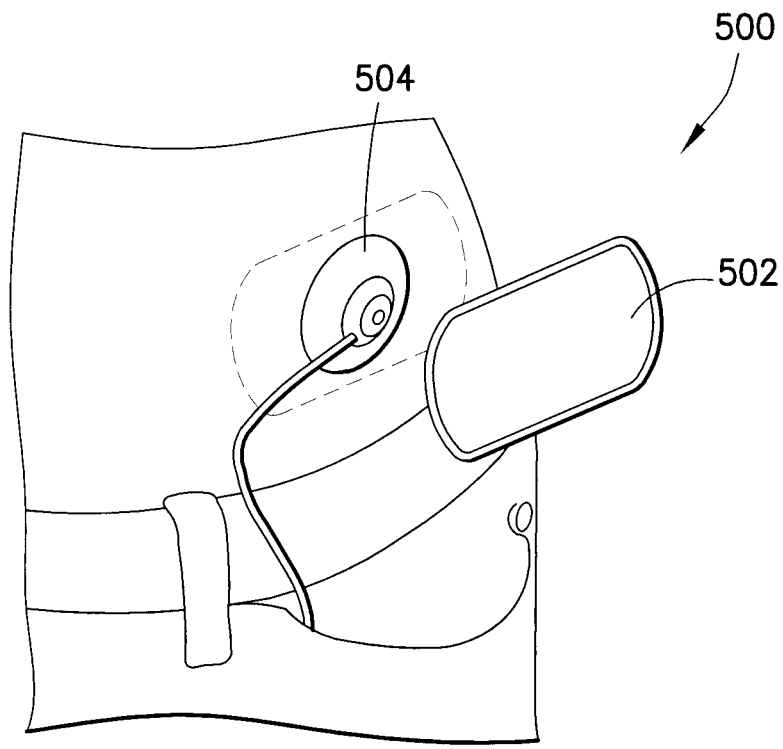
FIGS. 9a-9b are perspective views of an exemplary set concealment element in accordance with an exemplary embodiment of the present invention.
Figure 9B:
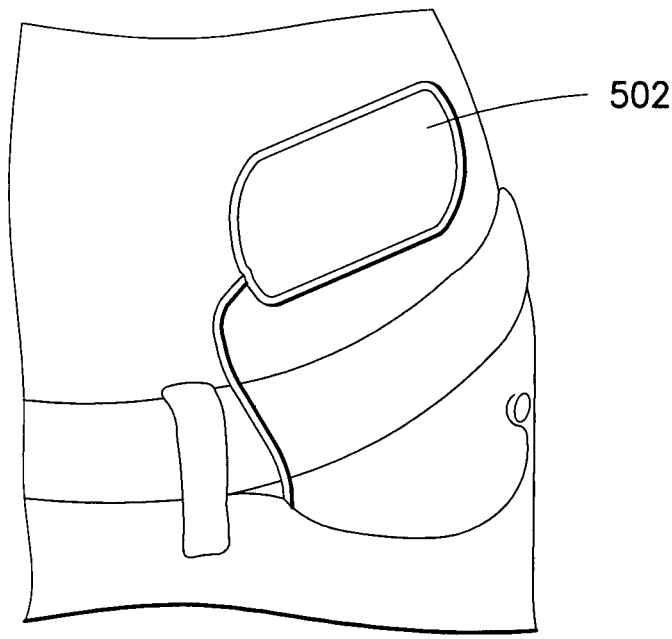

One or more of the exemplary embodiments of the present invention described herein can be further provided with additional features or elements to provide set concealment in some manner as desired by a user. As shown by way of example, a concealment element 500 is shown in FIGS. 9a-9b. In FIG. 9a, an adhesive covering 502, similar to a large adhesive bandage, can be provided to enable the user to cover the site, including the set 504, with an inconspicuous dressing. In an exemplary embodiment of the present invention, the covering 502 comprises a flexible, skin-colored adhesive covering that can have an adhesive side and a non-adhesive side. The adhesive side can be covered with a user-removable cover (not shown) that when removed, allows the covering 502 to be secured over the site, thereby covering and to a large degree, concealing the set 504 as shown in FIG. 9b.

Figure 10A:
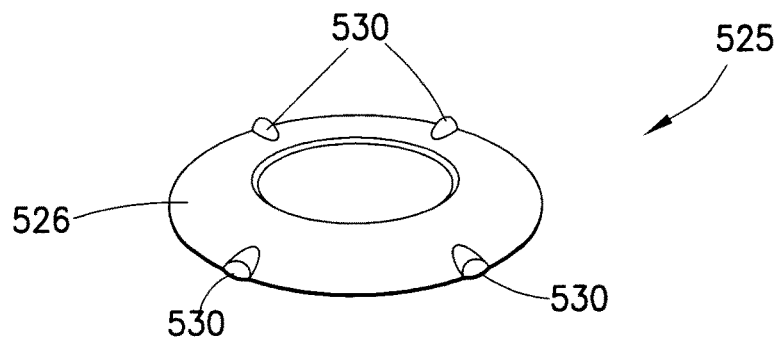
FIGS. 10a-10c are perspective views of exemplary set placement elements in accordance with an exemplary embodiment of the present invention.
Figure 10B:
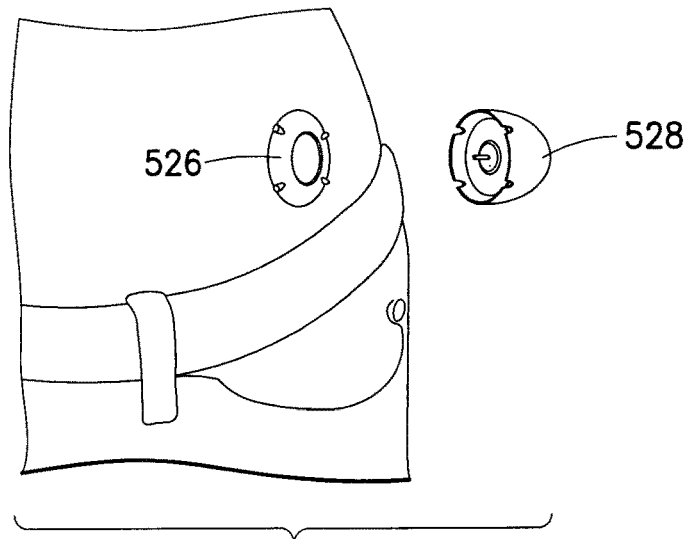
Figure 10C:
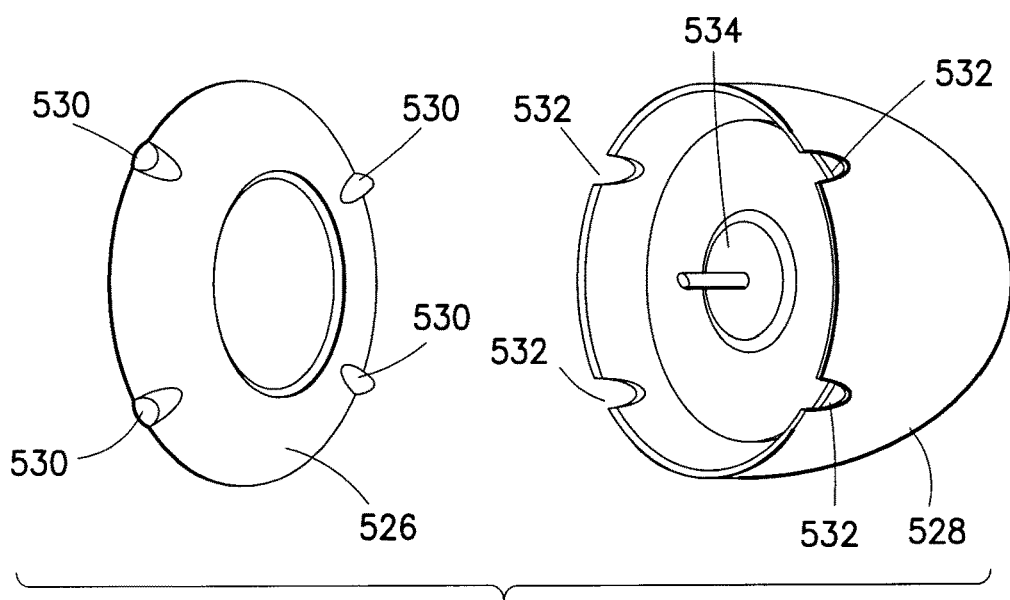

One or more of the exemplary embodiments of the present invention described herein can be further provided with additional features or elements to aid and/or simplify placement of the device in some manner as desired by a user. As shown by way of example, a collection of placement assistance elements 525 is shown in FIGS. 10a-10c. Since the set and the corresponding insertion device can be unavoidably large in diameter and difficult to accurately locate in some circumstances, an exemplary kit including embodiments of the present invention can further include a placement ring to aid in placement of the set. An exemplary placement ring 526 is shown in FIG. 10a and can comprise a ring-shaped plastic part with one or more orienting features 530, such as keys, on its perimeter, and a self-adhesive, covered pad on the underside (not shown). A low-profile, contoured circular plastic ring is shown, but embodiments of the present invention are not limited thereto. As the ring 526 can be provided with an adhesive pad, the ring 526 can be first gently adhered to the skin surface with the target insertion site at the center as shown in FIG. 10b. This allows careful set placement as the insertion site can now be better visualized though a center opening of the ring 526, and the insertion device 528, or tool, can be aligned with, and guided into final position, by the placement ring 526.

The insertion device 528 can be provided for use with the placement ring 526, and be constructed as described elsewhere herein and further having corresponding detents or keyways 532 to align with and receive the orienting features 530 of the placement ring 526. When the insertion device 528 is to be placed atop the placement ring 526 as shown in FIG. 10c, the insertion device 528 self-aligns and orients for precise location of a set 534. In the exemplary embodiment shown, the orienting features 530 are formed as raised contoured detents. Therefore, each further serves to guide, center and align the insertion device 528 upon placement. That is, such contoured elements provide a degree of self-alignment not as readily provided by square elements for example. After insertion, the set 534 is left remaining at a center of the ring 526 upon removal of the insertion device 528. The placement ring 526 can then be removed and discarded.

Figure 11:
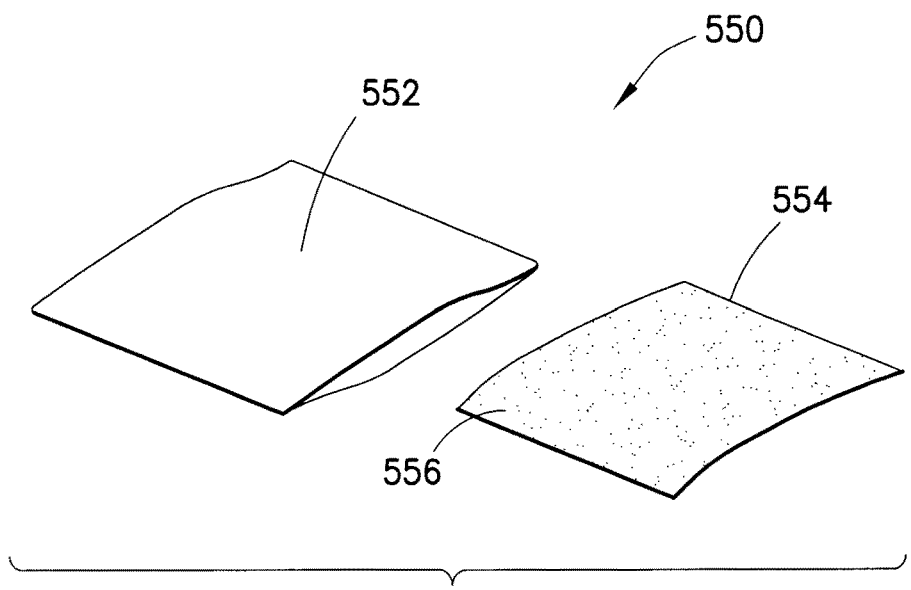
FIG. 11 is a perspective view of an exemplary set site placement preparation element in accordance with an exemplary embodiment of the present invention.

One or more of the exemplary embodiments of the present invention described herein can be further provided with additional elements for the use of site preparation. Such an exemplary feature is shown in element 550 of FIG. 11. In the exemplary embodiment shown in FIG. 11, set packaging can further include a site preparation wipe 554 contained within a preservation container 552. The packaging for the set can include the wipe 554, such as a versatile disposable wipe, paper or cloth pad that is soaked or impregnated with one or more of a disinfectant, local anesthetic or other helpful substance. The pad or wipe 554 may also be constructed having a texture, coating, or other surface feature 556 that can provide an exfoliating ability to aid in anesthetic effectiveness.

Figure 12A:
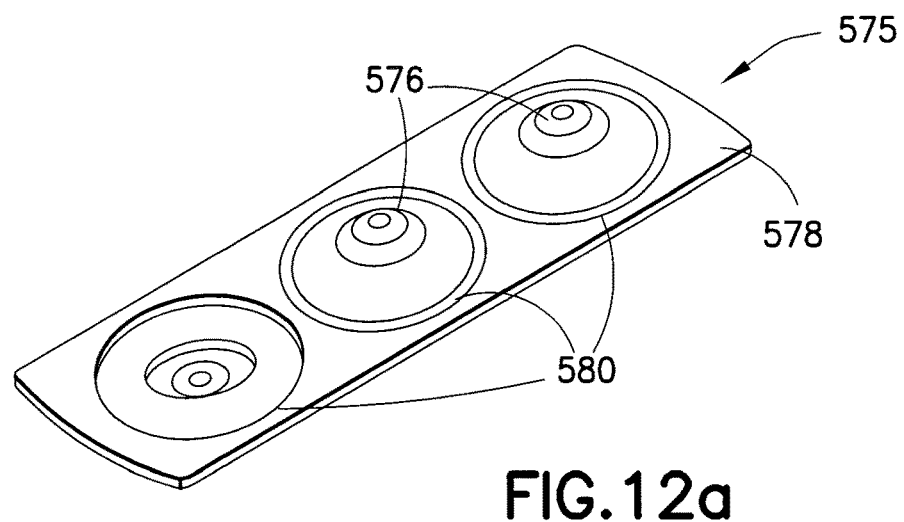
FIGS. 12a-12f are views of exemplary sets on tray packaging in accordance with an exemplary embodiment of the present invention.
Figure 12B:
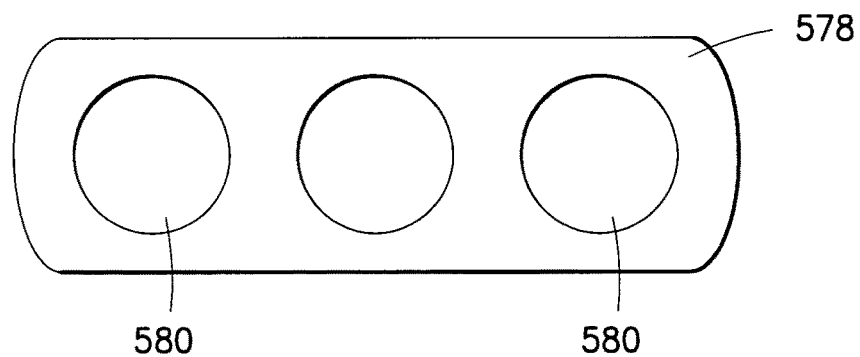

One or more of the exemplary embodiments of the present invention described herein can be further provided with additional features or elements to provide a simple but effective means to provide packaging as a number of sets upon a tray as desired by a user. As shown by way of example, a "sets on tray" packaging arrangement 575 is shown in FIGS. 12a-12f. As shown in FIGS. 12a-12f, a number of exemplary sets 576 can be packaged upon a tray 578. Although the exemplary tray of FIG. 12a shows the containment of three sets, any number or arrangements of sets can be included as desired by the user.

As shown in FIG. 12a, a number of disposable sets or set components 576 can be packaged in the exemplary multi-unit, foil or plastic-sealed tray 578. In the exemplary embodiment of the present invention shown in FIG. 12a, the tray 578 can be constructed of any suitable material compatible with the set and set components to be stored therein, and can provide a number of recessed, contoured or otherwise constructed openings 580 into which the sets or set elements 576 can be positioned. The openings 580 can be configured to securely hold and protect the sets prior to use, allow easy covering of the sets and tray surface with a sealing means, such as foil or other material which can then be easily removed or punctured by the user to access the desired set and maintain protection of remaining sets as shown in FIG. 12a, and which allows such access and removal using an inserter device 582 as shown in FIGS. 12c-12f.

Figure 12C:
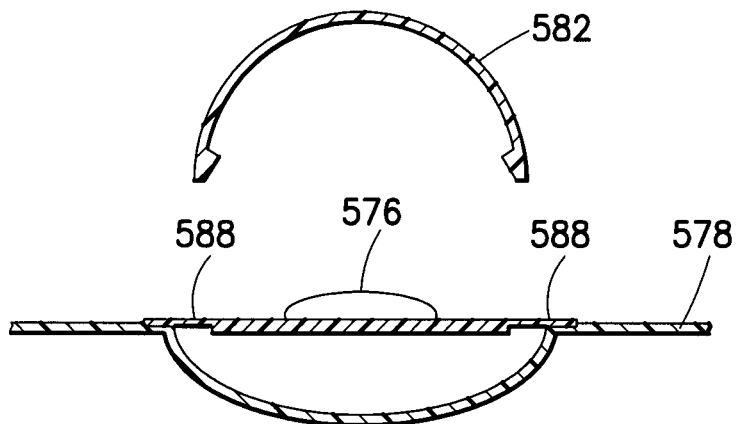
Figure 12D:
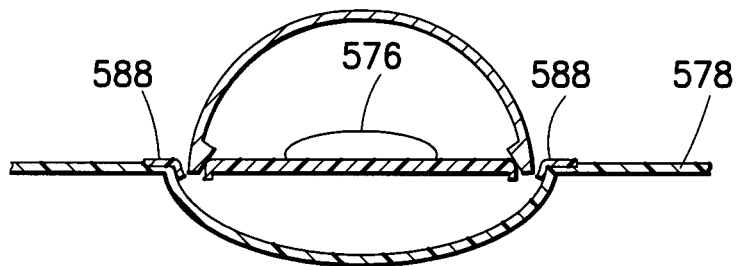
Figure 12E:
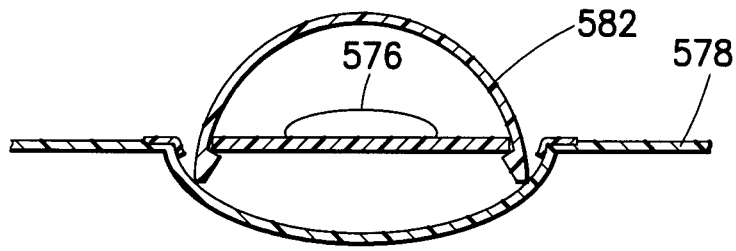

As illustrated in the cross-sectional views of FIGS. 12c-12f, an exemplary insertion device 582 is shown having a contoured shape into which the set 576 can be captured. To do so, the insertion device 582 can comprise one or mover deflectable ends 584 which can have an inclined latch 590 to pierce the tray covering 588 as shown in FIG. 12d, deflect outward slightly due to contact with the set 576, and then capture an outer circumference of the set 576 once the latch 590 is fully inserted. In doing so, the insertion device 582 can be used to extract a new set 576 from the package so that the user will not need to contend with opening and unsealing packaging materials. For example, an exemplary and reusable insertion device 582 for use which such a tray can comprise a hollow underside or lower surface, with the engagement features of the latches 590 oriented inward towards the set 576, such that a user is simply required to align the insertion device 582 with a set, insert to a sufficient depth and retrieve the set 576 for use. No further user action is required in regard to handling the set 576.

As shown in FIG. 12c, the sets 576 are aligned within each opening of the tray with sufficient clearance below the set to accommodate any elements of the set. A substantial portion of the upper surface of the set can be exposed, wherein a foil or other covering 588 can be used to secure the set 576 within the tray, and seal the contents of the tray and set 576 from contamination or other damage. In this exemplary embodiment of the present invention, the foil 588 is shown covering the limited space surrounding each device, but is not limited thereto. In yet other embodiments of the present invention the foil or covering can be more or less extensive upon the tray surface as desired.

Figure 12F:
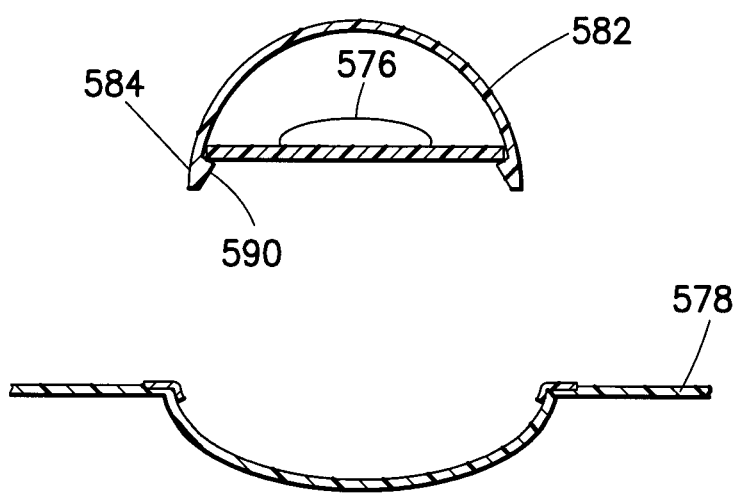

As shown in FIG. 12d, the insertion device 582 can self-align on the blister-type package of the set 576 on the tray 578, and when pressed down, can cut through the foil or plastic seal 588 as shown in FIGS. 12c and 12d. As the insertion device 582 presses down further, it also disengages the set 576 from the packaging tray 578 with the perimeter of the inserter body. After pushing past the edge of the set 576, the locking tabs or latches 590 on the insertion device 582 engage and secure the outer circumference of the set 576, and allow the user to extract both the insertion device 582 and the set 576 from the tray 578 as shown in FIG. 12f. The insertion device and the set are then ready to fire in normal use. The remaining sets of the tray are left intact and ready for later use. In exemplary embodiments of the present invention, the removal of the set 576 from the tray also results in the automatic removal of any needle cover and adhesive backing, which is left with the tray 578.

One or more of the exemplary embodiments of the present invention described herein can be further provided with additional features or elements to provide a simple but effective multistage-type inserter as desired by a user. As shown by way of example, a "multistage-type" inserter device 600 is shown in FIGS. 13a-13f. In such an exemplary embodiment, the insertion device can be constructed in such a way as to separate high-cost parts from low-cost parts, keeping the former in a reusable mechanism while allowing the latter to be safely disposed.

Figure 13B:
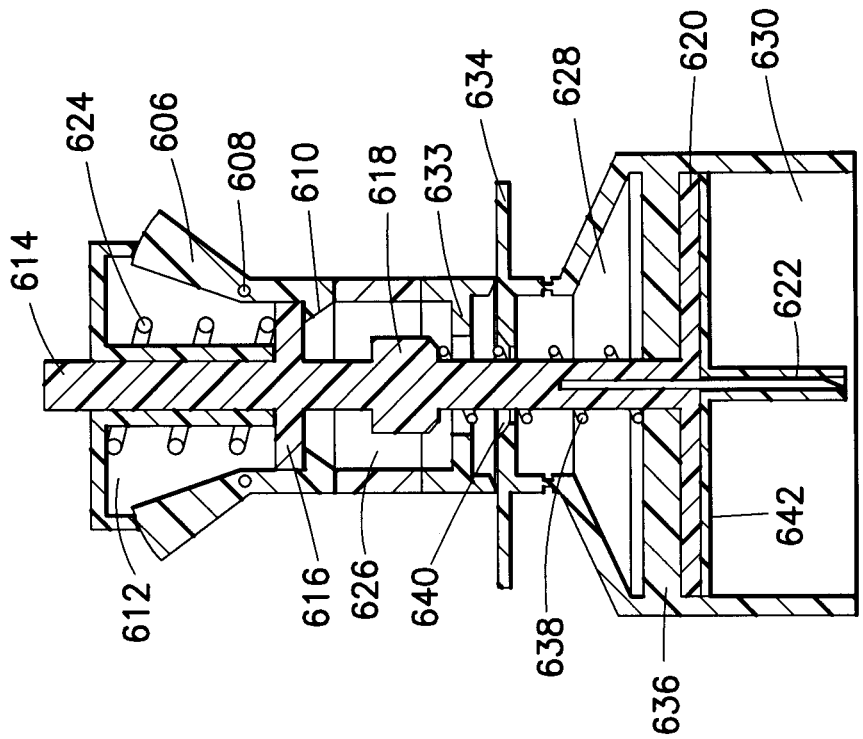
FIGS. 13a-13f are views of an exemplary multistage insertion device in accordance with an exemplary embodiment of the present invention.
Figure 13A:
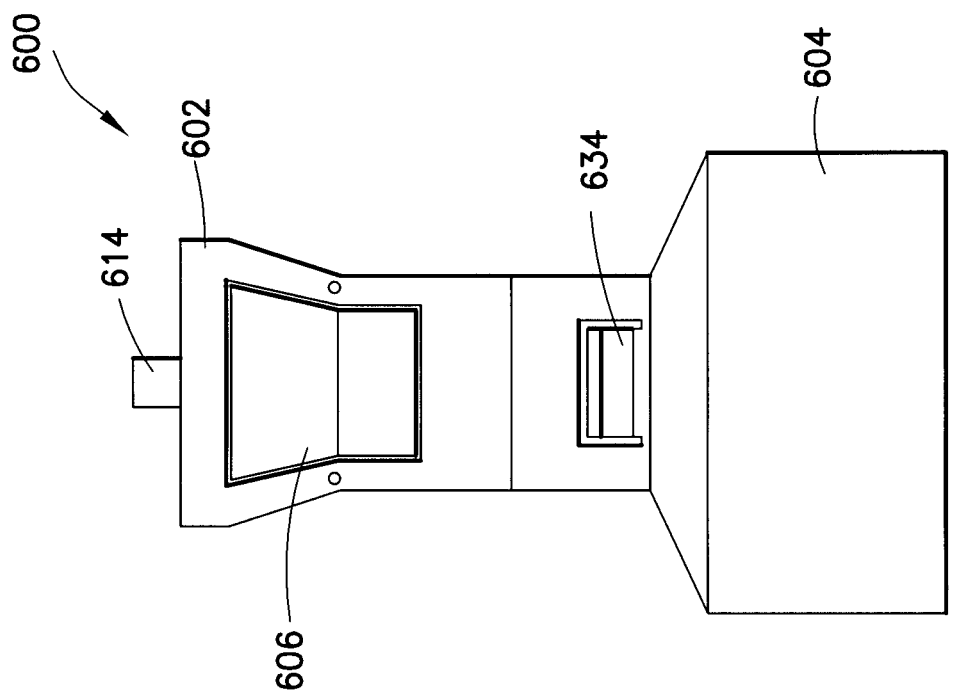

As shown in FIG. 13a, the multistage-type inserter device 600 can comprise a substantially cylindrical upper and lower element 602 and 604, respectively. The upper element 602 can have a first diameter at a lower portion thereof to seamlessly mate with the lower element 604. An upper portion of the upper element 602 can have a second diameter which is flared or expanded to provide sufficient room for operation of hinged latches 606 as described in greater detail below. The lower element 604 can also have a first diameter at an upper portion thereof to seamlessly mate with the upper element 602, and a second diameter at a lower portion which is flared or expanded to contain a set 642.

The upper element 602 can comprise at least one firing mechanism consisting of at lease one hinged latch 606 rotatable about a pin 608 or other means, and which has a inclined projection 610. Each projection 610 includes an inclined lower surface to facilitate assembly with the lower element 604, and a substantially flat upper surface to restrict some portion of an inserter rod 614 as described in greater detail below. The upper element 602 further comprises a first chamber 612 in which a firing spring 624 is captured. The upper element 602 and contents thereof can comprise a reusable element that can be installed onto a disposable mechanism of the lower element 604 which can include a set, needle, adhesive pad, and a portion of the insertion mechanism.

The inserter rod 614 extends though both the upper and lower elements 602 and 604, and comprises a cross-member 616, a shoulder 618 and a planar end 620. The inserter rod 614 further comprises an inserter needle 622, which can be secured within a center opening of the inserter rod 614, and can extend downward from the rod at the end 620. Both the cross-member 616 and the lower end 620 are configured to have a width substantially equal to the width of the chamber in which each is positioned to facilitate alignment and travel of the inserter rod 614 during use. As described in greater detail below, the cross-member 616 is configured to be held in an up position by the projections 610 of the latches 606, and is configured to be blocked at a down position by the projections 633 of the lower element 604. Further, the lower part of the shoulder 618 is configured to have a partially flat surface upon which the retraction spring 638 rests, and a partially inclined surface such that the shoulder can be easily forced through the opening of the partition 634 by the firing spring 624. The upper part of the shoulder 618 is configured to have a substantially flat surface to be captured by the opening of the partition 634 and prevent upward travel of the inserter rod 614 for retraction until released.

Figure 13D:
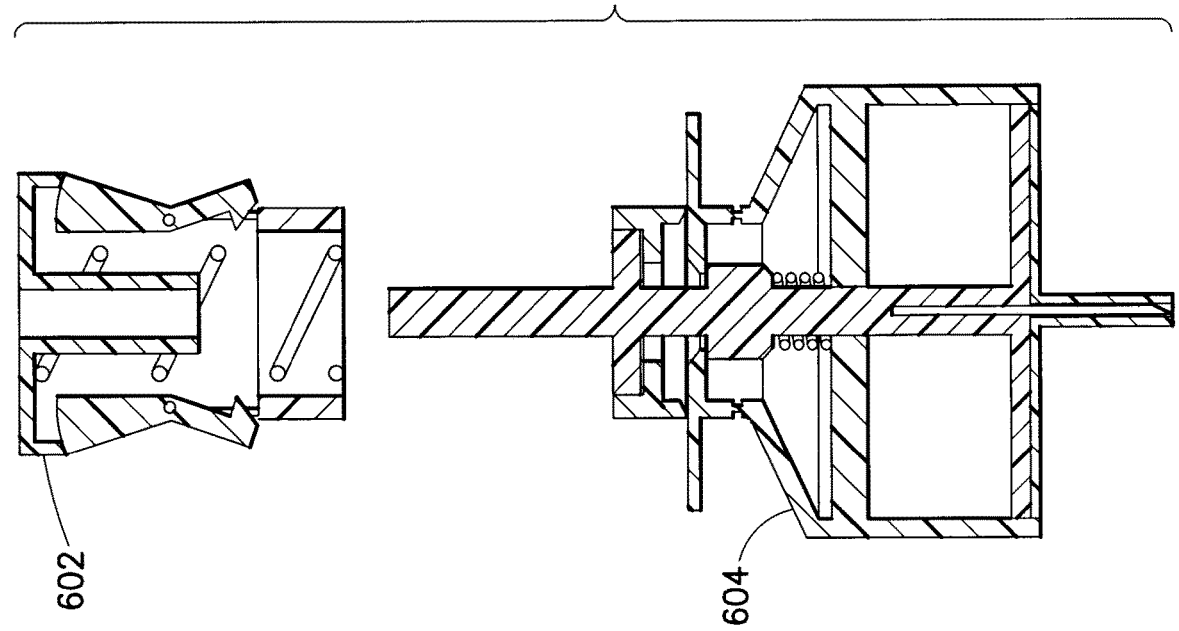
Figure 13C:
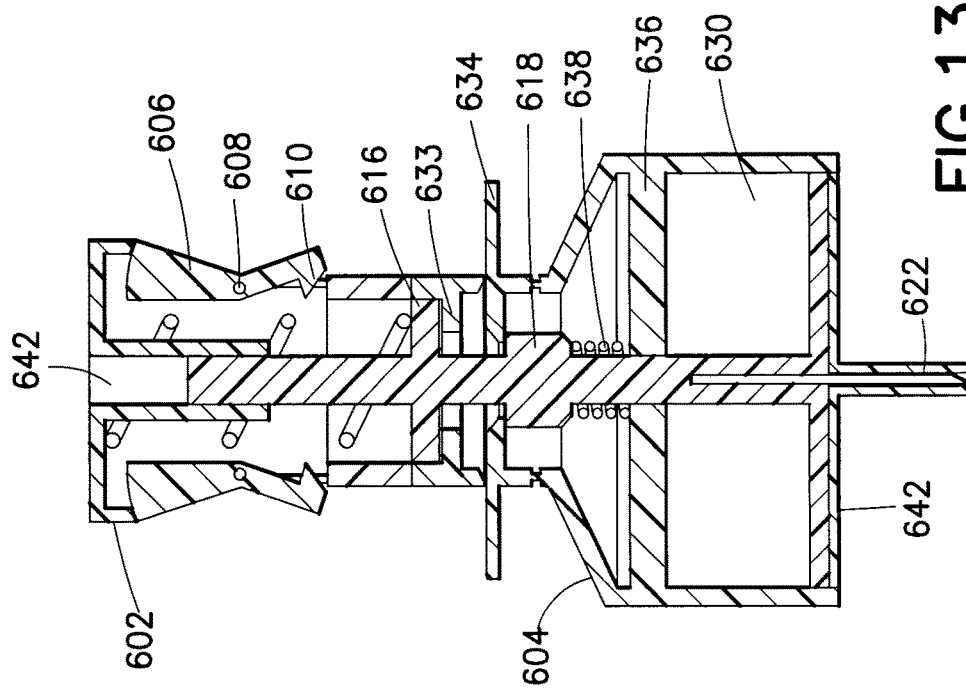

The upper portion 602 comprises the first chamber 612 in which the firing spring 624 is captured. The firing spring 624 is disposed concentrically about the inserter rod 614 and is captured between an upper wall of the first chamber 612 and the cross-member 616 of the inserter rod 614. In doing so, the firing spring 624 is configured to constantly urge the inserter rod 614 downward. Prior to use, the inserter rod 614 is held in an up position by one or more of the projections 610 of the hinged latch 606. Specifically, an inner surface of the hinged latch 606 comprises one or more of the projections 610 which extend a slight distance from the inner surface of the hinged latch 606, and which block the travel of the cross-member 616 of the inserter rod 614. In such a position, the firing spring 624 is compressed and the latches 606 capture the upper portion of the needle assembly as shown in FIG. 13b. The capture of the upper portion of the inserter rod 614 by the projections 610 of the latches 606, and the force applied by the firing spring 624 while in the pre-use position, also serves to secure the upper housing 602 to the bottom housing 604 prior to use. Once the latches 606 are released from the inserter rod 614, the upper housing 602 is free of the lower housing 604 and can be lifted away as shown in FIGS. 13c-13d.

The upper housing 602 can further comprise an opening 642 which can serve to support the firing spring 624 in position, and serve to guide the inserter rod 614 during use. The opening 642 can further reveal an extended portion of the inserter rod 614 as shown in FIG. 13b such that a user can confirm visually or by touch that the elements are all present and are properly assembled and ready for use.

The lower portion 604 comprises a second, third and fourth chamber 626, 628 and 630. The second chamber 626 is substantially open at an upper surface to slidably receive the inserter rod 614 as guided by the cross-member 616 as urged downward by the firing spring 624 when released. The second chamber 626 comprises at least one projection 633 which extends inward from an inner surface of the second chamber 626. In doing so, the projection 633 provides a downward travel limit of the inserter rod 614 through the contact between the cross-member 616 and the projection 633. As noted above, the width of the second chamber and the cross-member 616 are configured such that the inserter rod 614 is centered and guided by each.

The second and third chambers 626 and 628 are separated by a partition 634 having an opening 640 through which the inserter rod 614 extends. The opening 640 of the partition 634 is configured to have an inclined upper opening surface through which the inclined lower surface of the shoulder 618 can more easily pass as urged downward by the firing spring 624. The lower surface of the opening 640 of the partition 634 is configured to be substantially flat such that the flat upper surface of the shoulder 618 cannot pass back though the partition 634 until released for retraction as described in greater detail below. Further, the partition 634 comprises at least one segment extending some distance from an outer surface of the lower element 604 (i.e., an extended user lever) such that the partition 634 can be deflected by the user for retraction as described in greater detail below.

The third and fourth chambers are also separated by a partition 636, which also includes an opening through which the inserter rod 614 extends. The third chamber 628 further comprises the retraction spring 638. The retraction spring is positioned concentric with the inserter rod 614, and is captured within the third chamber 628 between the partition 636 and the shoulder 618 of the inserter rod 614. In doing so, the retraction spring 638 is configured to constantly urge the inserter rod 614 upward.

Prior to use, the firing spring 624 in the upper portion 602 is compressed and the retraction spring 638 in the lower portion 604 is relaxed as shown in FIG. 13b. During use, the release of the firing spring 624 operates the inserter as described in greater detail below, and further serves to compress the retraction spring 638 as shown in FIG. 13c. After use, the inserter rod 614 is held in position by the contact between the shoulder 618 and the partition 634 as shown in FIG. 13d. To retract the inserter rod 614, the user than presses on the extended portions of the partition 634. As shown in FIGS. 13d and 13e, the restrictive opening 640 of the partition 634 serves to hold the inserter rod 614 in the down position. When the insertion is completed and the upper portion 602 is removed, the user can press the extended portions of the partition 634, and the opening 640 is enlarged and allows the shoulder 618 to retract upward as urged by the retraction spring 638 as shown in FIG. 13e.

While in the pre-use position, a large portion of the lower portion 604 remains open to the end of the device. In doing so, the set 642 can be positioned on the extended needle 622, at an opposite side of the end 620 of the inserter rod 614. The set 642 can be gently held within the portion 604 through contact with the walls of the portion, and/or through contact with the inserter needle 622. As noted elsewhere, the set can include any number or configurations of adhesive pads (not shown) and other connection features, which can be accommodated by the two-part inserter.

Figure 13F:
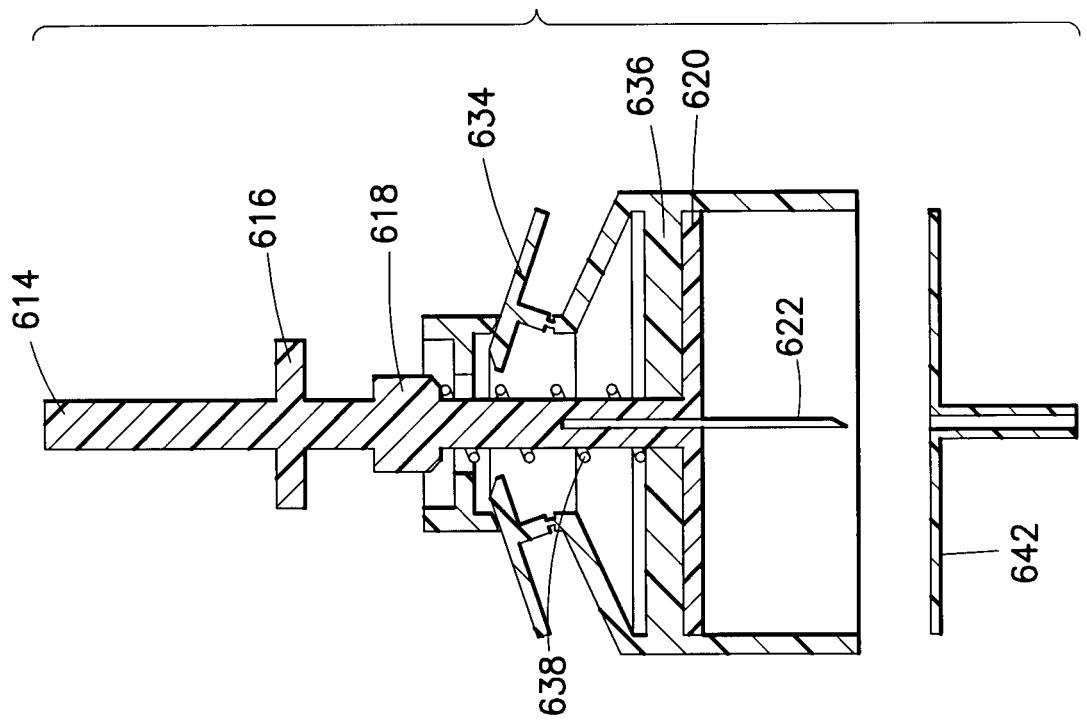
Figure 13E:
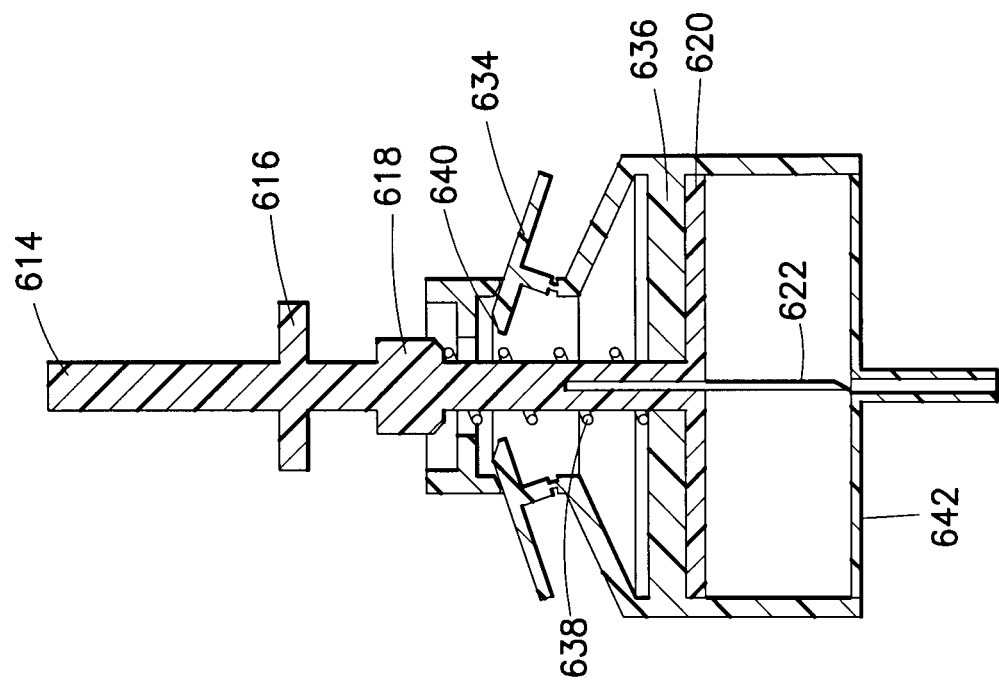

As shown in FIGS. 13a-13f, the compression of the latches 606 releases the projection latch on the needle assembly of the inserter rod 614, permitting the firing spring 624 to drive the needle 622, set 642, and adhesive pad into the region of the skin beneath the portion 604, and also compress the retraction spring 638. That is, upon release, the inserter rod 614 is free to travel downward as urged by the trapped spring 624. In doing so, the inserter rod 614, including its end 620 and needle 622 travel downward through the portion 604, urging the set 642 downward with it. At or before reaching the travel limit of the inserter rod 614, the set is positioned, and the device can be removed as shown in FIG. 13f, thereby leaving the set 642 at the desired insertion site.

Then, to retract the inserter rod 614, including its end 620 and needle 622, the user then presses on the extended portions of the partition 634. As shown in FIGS. 13d and 13e, the restrictive opening 640 of the partition 634 serves to hold the inserter rod 614 in the down position. When the insertion is completed and the upper portion 602 is removed, the user can press the extended portions of the partition 634, and the opening 640 is enlarged and allows the shoulder 618 to retract upward as urged by the retraction spring 638 as shown in FIG. 13e. The inserter rod 614 is prevented from completely exiting the lower portion 604 by the contact between the lower end 620 and the partition 636.

As noted above, the exemplary embodiment of the present invention illustrates an insertion device 600 that can be constructed in such a way as to separate high-cost parts from low-cost parts, keeping the former in a reusable mechanism while allowing the latter to be safely disposed as shown in FIG. 13a. A firing mechanism consisting of the hinged latches 606 and an extended, large spring is installed onto a disposable mechanism which includes the set 642, the needle 622, the adhesive pad, and a portion of the insertion mechanism. As shown, the firing spring 624 is compressed and the latches 606 capture the upper portion of the needle assembly or inserter rod 614 as shown in FIG. 13b. The device is now ready to be placed and fired.

Once the user squeezes the latches 606 on the upper part of the device, the needle assembly or inserter rod 614 becomes free to move, and is driven downward by the firing spring 624, piercing the skin, inserting and adhering the set 642 as shown in FIG. 13c. The downward motion of the needle assembly or inserter rod 614 also drives two secondary latches on the lower portion of the device outward to capture the inserter rod 614 within the opening 640 and compresses the return or retraction spring 638. After removal of the reusable part 602 of the device 600, the lower part of the device 604 remains in place and the needle will still be inserted in the skin as shown in FIG. 13d. To remove the needle 622, the latches or the member 634 can be deflected as shown in FIG. 13e to allow the return or retraction spring 638 to extract the needle 622 and render the lower part 604 of the assembly 600 inert and disposable. The inserter rod 614 is prevented from completely exiting the lower portion 604 by the contact between the lower end 620 and the partition 636.

One or more of the exemplary embodiments of the present invention described herein can be further provided with additional features or elements to provide a simple but effective "squeeze-type" inserter as desired by a user. As shown by way of example, a "squeeze-type" inserter device 700 is shown in FIGS. 14a-14d. As shown in FIGS. 14a-14d, an exemplary embodiment of the present invention can be activated by pressing the device against the targeted portion of the skin and then squeezing a portion of the inserter body.

An exemplary construction of the squeeze-type insertion device 700 can comprise a body having at least three portions 702, 704 and 706. The portions 702 and 706 can comprise rigid structures, having a flexible user-deflectable portion 704 disposed therebetween. The upper portion 702 can comprise a substantially cylindrical outer surface having a rounded and closed end, and an opposite end which seamlessly mates with the outer surface of the user-deflectable portion 704. The lower portion 706 can have a larger diameter, substantially cylindrical outer surface, with a contour configured to seamlessly mate with the outer surface of the user-deflectable portion 704. Accordingly, the user-deflectable portion 704 can have a substantially cylindrical outer surface having a contour to provide seamless mating with the outer surface of the upper and lower portions 702 and 706. The portions 702, 704 and 706 can be constructed as a single element wherein each section is separated from the adjacent section by one or more cuts, which allow the segments to maintain assembly, but allow for the deflection of the user-deflectable portion 704 as described in greater detail below. Further, an inserter rod 712 is slidably captured within the device 700 and extends through each portion as guided by an inserter rod cross-member 714. The inserter rod 712 further comprises a lower planar end 722 and an inserter needle 724, which can be secured within a center opening of the inserter rod 708, and can extend downward from the inserter rod 712 at the end 722. Both the cross-member 714 and the lower end 722 are configured to have a width substantially equal to the width of the chamber in which each is positioned to facilitate alignment and travel of the inserter rod 712 during use.

As shown in FIGS. 14a-14c, the upper portion 702 provides a first chamber 708 in which a firing spring 710 is captured. Specifically, the firing spring 710 is positioned concentric with the inserter rod 712, and is captured at one end by an upper wall of the first chamber 708, and at an opposite end by the inserter rod cross-member 714. In doing so, the firing spring 710 is configured to constantly urge the inserter rod 712 downward.

Prior to use, the inserter rod 712 is held in position by one or more projections 716. Specifically, an inner circumference of the user-deflectable portion 704 comprises one or more of the projections 716 which extend a slight distance from the inner circumference of the user-deflectable portion 704, and which block the downward travel of the cross-member 714 of the inserter rod 712. The projections 716 are provided at an uppermost point of the portion 704 as this point undergoes the greatest degree of deflection during user deflection as described in greater detail below. Accordingly, in such a position, the degree of deflection of the projections 716 is maximized as shown in FIG. 14b to simplify the release of the inserter rod 712.

The user-deflectable portion 704 provides a second chamber 718 through which the inserter rod 712 is positioned and which includes a travel limit element 720. Although any part of the user-deflectable portion 704 can be compressed by a user, an exemplary embodiment of the present invention can provide one or more designations on an outer surface of the user-deflectable portion 704 to identify each as a preferred "squeeze button" area. Once the user-deflectable portion 704 is compressed by the user as shown in FIG. 14b, the projections 716 release the cross-member 714 of the inserter rod 712 and the firing spring 710 urges the inserter rod 712 downward through the second chamber 718 until the cross-member 714 is restricted from further downward travel by the travel limit element 720 as shown in FIG. 14c. As noted above, the portions 702, 704 and 706 can be constructed as a single element wherein each section is separated from the adjacent section by one or more cuts, which allow the segments to maintain assembly but allow for the deflection of the user-deflectable portion 704. Accordingly, the engagement between the portions 704 and 708 can be deflected in a manner similar to that of the deflection between the portions 702 and 704 described above in regard to the release of the inserter rod 712.

While in the pre-use position, a large portion of the lower portion 706 remains open to the end of the device. In doing so, a set 726 can be positioned on the extended needle 724, at an opposite side of the end 722 of the inserter rod 712. The set 726 can be gently held within the portion 706 through contact with the walls of the portion, and/or through contact with the inserter needle 724. As noted elsewhere, the set 726 can include any number or configurations of adhesive pads (not shown) and other connection features, which can be accommodated by the squeeze-type inserter.

As shown in FIGS. 14a-14d, the compression of the user-deflectable portion 704 releases the projection latch 716 on the needle assembly of the inserter rod 712, permitting the firing spring 710 to drive the needle 724, set 726, and adhesive pad into the region of the skin beneath the portion 706. That is, upon release, the inserter rod 712 is free to travel downward as urged by the trapped spring 710. In doing so, the inserter rod 712, including its end 722 and needle 724 travel downward through the portion 706, urging the set 726 downward with it. At or before reaching the travel limit of the inserter rod 712, the set 726 is positioned, and the device 700 can be removed as shown in FIG. 14d, thereby leaving the set 726 at the desired insertion site.

Such an exemplary embodiment of the present invention provides a more convenient means of actuating an insertion device by simply using "squeeze" buttons to initiate the process as shown in FIG. 14a. As shown in FIG. 14b, buttons on the side of the device at the user-deflectable portion 704 can be pressed inward, unlatching the needle assembly or inserter rod 712 and permitting it to be propelled downward by the firing spring 710 as shown in FIGS. 14b and 14c. The spring-loaded needle delivers the set 726 and adhesive pad to the skin. The device 700 can then be removed as shown in FIG. 14d, thereby leaving the set 726 at the desired insertion site.

In contrast to the other inserter devices described herein, the materials of the squeeze-type inserter 700 allow for the squeeze action of the one or more portions, or the construction of one or more portions having thinner, thereby deflectable parts.

One or more of the exemplary embodiments of the present invention described herein can be further provided with additional features or elements to provide a simple but effective skin contact-type inserter as desired by a user. As shown by way of example, a "skin contact-type" inserter device 800 is shown in FIGS. 15a-15e. As shown in FIGS. 15a-15e, an exemplary embodiment of the present invention is shown wherein the insertion device can be activated by pressing the device up against the targeted portion of the skin.

An exemplary construction of the insertion device 800 can comprise an upper and lower portion 802 and 804, respectively. The upper portion 802 can be comprised of a dome-shaped element into which a slidably engaged lower portion 804 can be captured. Specifically, the upper portion 802 can comprise a substantially round, dome-shaped element having a flattened portion at an uppermost point. The upper portion 802 can further comprise one or more deflectable tabs 806, or cut portions, about a body circumference as described in greater detail below. The inner surface of the tabs 806 are provided with an incline 824 and a projection 818 at the uppermost point of each incline.

Within the upper portion 802, exemplary embodiments of the present invention comprise an inserter rod 808 slidably disposed within the upper portion and which is held in place by the tabs 806. As shown in FIGS. 15b-15e, the inserter rod 808 comprises a planar end 814 wherein a notch 816 is proved at each side of the planar end 814, which engages the projections 818 of the tabs 806 that extend into the upper portion 802. Accordingly, prior to use, the projections 818 secure the notches 816 of the planar end 814 of the inserter rod 808, preventing movement of the inserter rod 808. The inserter rod 808 further comprises an inserter needle 828, which can be secured within a center opening of the inserter rod 808, and can extend downward from the rod at the planar end 814.

The upper portion 802 further comprises a firing spring 810 that is disposed concentrically with the inserter rod 808 and which is captured between the end 814 of the inserter rod 808 and one or more features of the upper flattened surface of the upper portion 802. In the exemplary embodiment shown, the upper flattened surface of the upper portion 802 can comprise a molding 820 having a cup-shaped opening 812 that is sized to capture and hold an end of the firing spring 810. In this position, the firing spring 810 serves to constantly urge the inserter rod 808 downward. However, as noted above, prior to use, the inserter rod 808 is held in place by the tabs 806.

Accordingly, the device 800 further comprises the slidably engaged lower portion 804 which is slidably captured at an end of the upper portion 802 by one or more contacting tabs 822 of portion 804, and tabs 832 of the upper portion 802. The lower portion 804 has a diameter slightly less than an inner diameter of the upper portion 802 such that the lower portion 804 is gently held in place prior to use but upon contact with a skin surface, can be easily slid upward into the upper portion 802. In doing so, the tabs 822 of the lower portion 804 travel against an inner circumference of the upper portion 802, and onto the tabs 806. Specifically, the tabs 822 of the lower portion 804 travel against the incline 824 of the tabs 806, which forces the tabs 806 outward and releases the projections 818 from the notches 816 of the planar end 814 of the inserter rod 808 as shown in FIG. 15*c*. Once released in such a manner, the inserter rod 808 is free to travel downward as urged by the firing spring 810.

While in the pre-use position, a large portion of both the upper and lower portions 802 and 804 remain open to the end of the device 800. In doing so, a set 826 can be positioned on the extended needle 828, at an opposite side of the planar end 814 of the inserter rod 808. The set 826 can be gently held within the upper portion 802 through contact with the walls of the upper or lower portion, and/or through contact with the inserter needle 828. As noted elsewhere, the set 826 can include any number or configurations of adhesive pads (not shown) and other connection features, which can be accommodated by the skin contact inserter.

As shown in FIGS. 15*b*-15*d*, the slidable motion of the lower portion 804 into the upper portion 802 releases the pin latch 818 on the needle assembly of the inserter rod 808, permitting the firing spring 810 to drive the needle 828, set 826, and adhesive pad into the region of the skin beneath the lower portion 804. That is, upon release, the inserter rod 808 is free to travel downward as urged by the trapped firing spring 810. In doing so, the inserter rod 810, including its end 814 and needle 828 travel downward through the lower portion 804, urging the set 826 downward with it. At or before reaching the travel limit of the inserter rod 808, the set 826 is positioned, and the device 800 can be removed as shown in FIG. 15*e*, thereby leaving the set 826 at the desired insertion site.

As described above, the lower portion 804 of the device becomes a movable actuation mechanism. In this case, a circumference or ring around the lower perimeter of the lower portion 804 of the device, surrounding the set 826 and needle 828, is placed against the skin surface (not shown). The entirety of the device 800 is then pressed firmly downward. The lower ring of the lower portion 804 telescopes into the main body of the upper portion 802 of the device and as it travels inward/upward, it deflects the multiple latches around the perimeter provided by the tabs 806, which permit the firing spring 810 to drive the needle 828, set 826, and adhesive pad into the skin. The device 800 can be removed as shown in FIG. 15*e*, thereby leaving the set 826 at the desired insertion site.

Figure 16A:
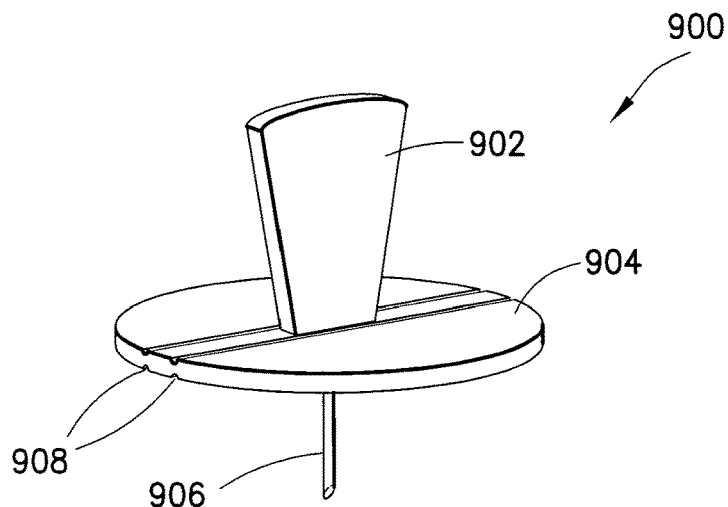
FIGS. 16a-16c are views of an exemplary needle handle and shroud in accordance with an exemplary embodiment of the present invention.
Figure 16B:
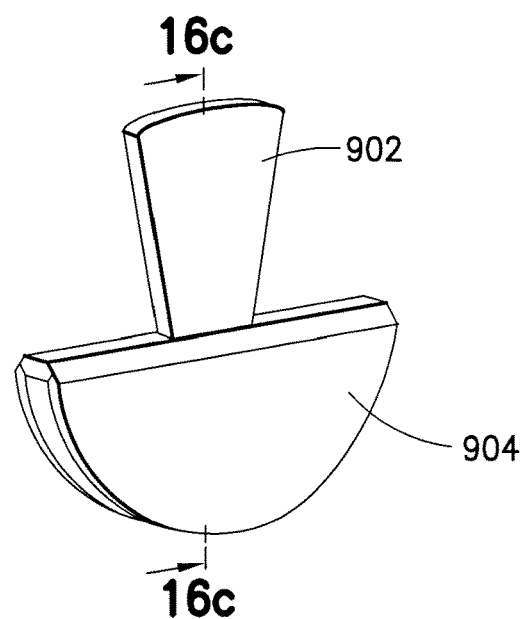
Figure 16C:
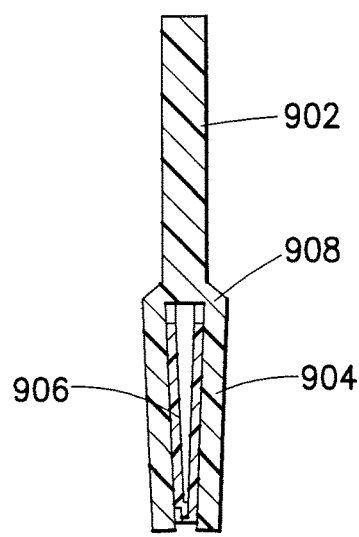

One or more of the exemplary embodiments of the present invention described herein can be further provided with additional features or elements to provide a needle handle and/or shroud in some manner as desired by a user. As shown by way of example, a needle handle and shroud 900 is shown in FIGS. 16*a*-16*c*. In doing so, an enhancement can be provided to current manually inserted needles for set insertion by implementing a plastic handle 902 and a substantially circular and hinged shield 904 for use with the needle 906 and set (not shown). The handle 902 permits a sure grip on the needle 906 for insertion, while the circular shield 904, as shown, helps to firmly press the set and set adhesive into place as shown in FIG. 16*a*. After placement, when the needle 906 is withdrawn, the hinged portions of the shield 904 can be folded down at each of hinges 908, as shown in FIG. 16*b* and the cross-sectional view of FIG. 16*c*, to allow for safer needle disposal.

One or more of the exemplary embodiments of the present invention described herein can be further provided with additional features or elements to provide a simple but effective skin pinch-type inserter as desired by a user. As shown by way of example, a "skin pinch-type" inserter device 925 is shown in FIGS. 17*a*-17*d*. As shown in FIGS. 17*a*-17*d*, an exemplary set can be packaged with a skin pinch-type inserter 925 with which a user can grasp a portion of the user's skin S (see, e.g., FIG. 17*a*) to improve insertion of the set. The exemplary insertion device 925 can be integrated into a mechanism as described in greater detail below that incorporates features to do this.

An exemplary construction of the insertion device 925 can comprise a large clothespin-like clamp 926, having opposite sides or legs 928 which rotate about a pin or other securing means 930. Such an exemplary clamp 926 can further provide a space therein in which a number of remaining components can be centered. The large clothespin-like clamp 926 can include the wide, manually-actuated legs 928 as shown in FIGS. 17*a*-17*b*. The legs 928 can be configured to be at slight angles while at rest such that a width between the legs 928 at the skin contact surface is wider than a width between the legs 928 at opposite ends. When activated by a user, the user places the entire device 925 against the skin surface such that the wider opening contacts the skin surface. The user than grasps the legs 928 at a point near the skin surface and "pinches" the legs 928 into a substantially parallel position, such that the legs 928 extend vertically from the skin surface as shown in FIG. 17*c*. That is, the device can be placed on the skin surface, surrounding the target area, and the pinching legs 928 can be squeezed inwards. When pinched, the legs 928 in contact with the skin surface serve to prepare the skin surface in a number of different ways for set placement, including, but not limited to, stretching the skin at the site, leveling the skin at the site and/or raising the skin at the site.

The squeezing of the legs 928 is also tied to a latching mechanism in the central section of the device 925. That is, when a desired degree of skin pinch is achieved, the device automatically begins the process of releasing and placing the set. To do so, the device 925 can further comprise a first and second chamber therein. The first chamber 932 is secured to the second chamber 934, which is secured at opposite corners to an inner surface of the legs 928. The legs 928 further comprise at least one articulated pin 936 which is inserted into the first chamber 932 when the device is at rest as shown in FIG. 17*b*. The articulated pin 936 can include one or more joints or segments along its length, such that there is no interference with the movement of the legs 928 during operation.

The articulated pin 936 extends from an inner surface of the legs 928, through an opening in the side of the first chamber 932 and secures a planar end 938 of an inserter rod 940. As shown in FIG. 17*b*, in doing so, the pin 936 holds the inserter rod 940 in an up and retracted position. As the legs 928 are pinched, the articulated pin 936 is pulled clear of the planar end 938 which allows the inserter rod 940 to move forward as urged by a firing spring 946.

As shown in FIGS. 17*b*-17*c*, the firing spring 946 is captured in the second chamber 934. Specifically, the first and second chambers are in communication via an opening therebetween through which the inserter rod 940 extends.

The planar end 938 of the inserter rod 940 is captured in the first chamber, and can be held at an upper and retracted position in the first chamber by the articulated pin 936. The remainder of the inserter rod extends into the second chamber 934 and terminates at an opposite planar end 944, and further comprises an inserter needle 942. The inserter needle 942 can be secured within a center opening of the inserter rod 940, and can extend from the rod at the planar end 944 into the second chamber 934. Both planar ends 938 and 944 are configured to have a width substantially equal to the width of the chamber in which each is positioned to facilitate alignment and travel of the inserter rod 940 during use.

The firing spring 946 is placed concentrically about the inserter rod 940 and is captured by the inserter rod 940 within the second chamber 934, between the end 944 and an upper wall of the second chamber 934, and is configured to be in a compressed state prior to use, and upon release of the articulated pin 936, is further configured to urge the inserter rod 940 downward toward the insertion site. As shown in FIG. 17b, while in the pre-use position, a large portion of the second chamber 934 at an opposite side of the planar end 944 remains open to the end of the device. In doing so, a set 948 can be positioned on the extended needle 942 within the second chamber 934, at an opposite side of the planar end 944 of the inserter rod 940. The set 948 can be gently held within the second chamber 934 through contact with the walls of the chamber, and/or through contact with the inserter needle 942. As noted elsewhere, the set 948 can include any number or configurations of adhesive pads (not shown) and other connection features, which can be accommodated by the skin pinch inserter.

Figure 17D:
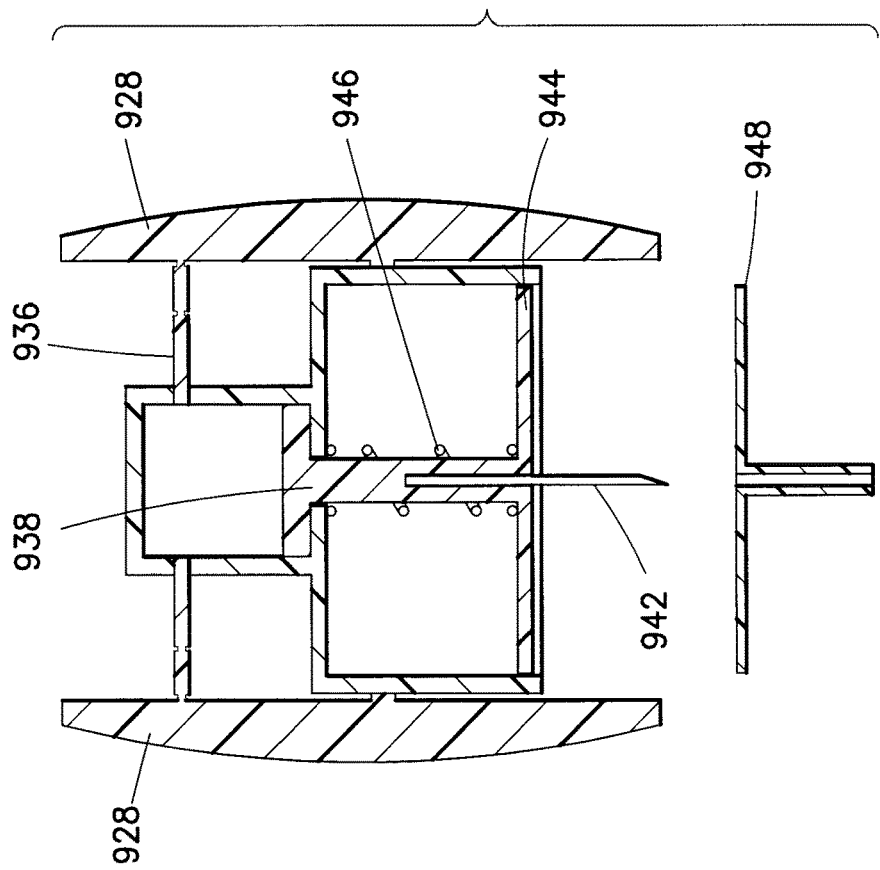
Figure 17C:
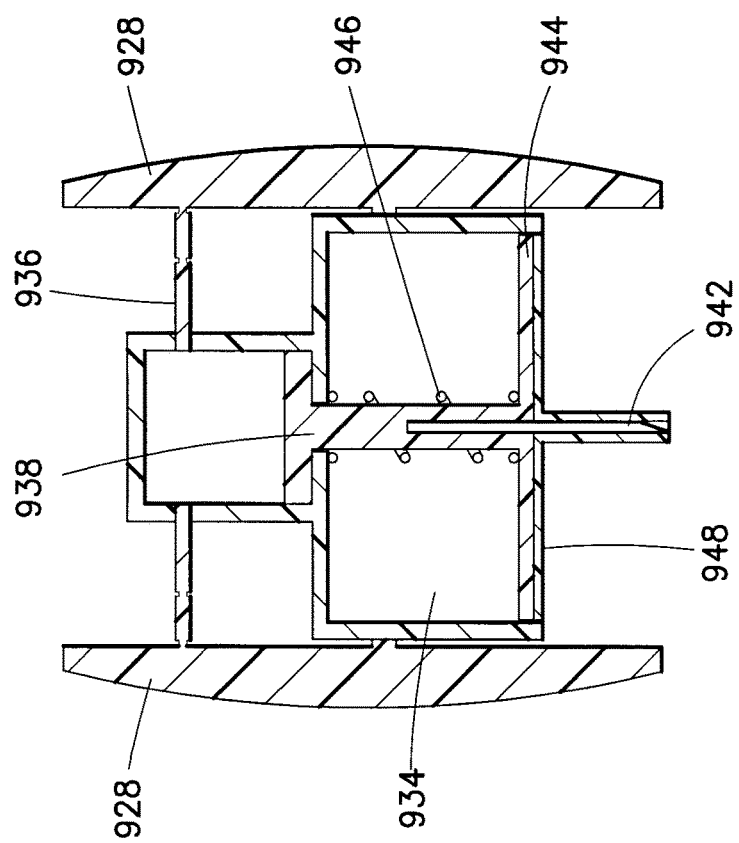

As shown in FIGS. 17b-17c, the motion of the legs 928 releases the pin 936 latch on the needle assembly of the inserter rod 940, permitting the firing spring 946 to drive the needle 942, set 948, and adhesive pad into the pinched region of the skin. That is, upon release of the articulated pin 936 from the first chamber 932, the inserter rod 940 is free to travel downward as urged by the trapped firing spring 946. In doing so, the inserter rod 940, including its planar end 944 and needle 942 travel downward through the second chamber 934, urging the set 948 downward with it. At or before reaching the travel limit of the inserter rod 940, the set 948 is positioned, and the device 925 can be removed as shown in FIG. 17d, thereby leaving the set 948 at the desired insertion site.

Figure 18A:
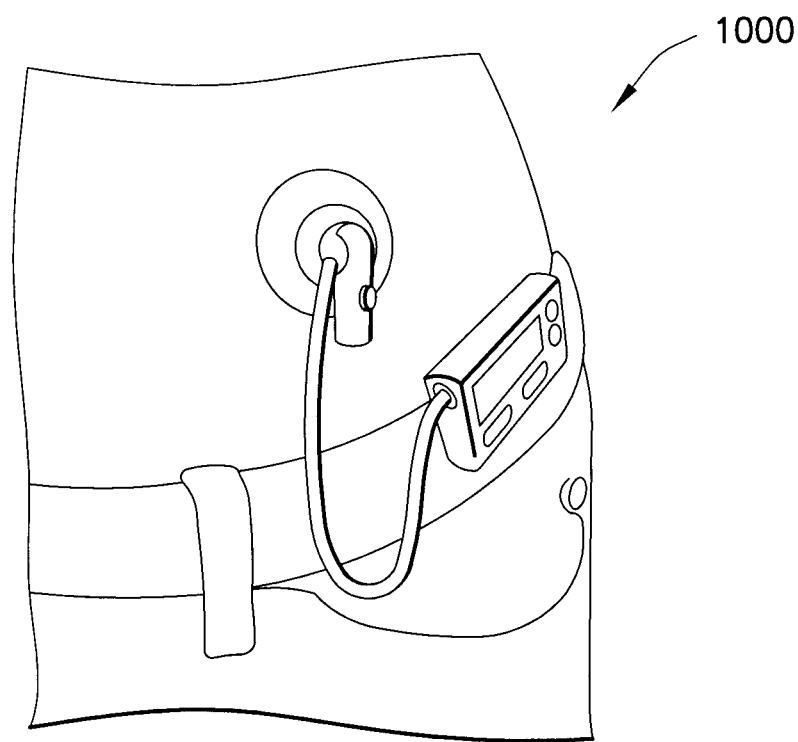
FIGS. 18a-18e are views of an exemplary "folding/retracting-type" inserter in accordance with an exemplary embodiment of the present invention.
Figure 18B:
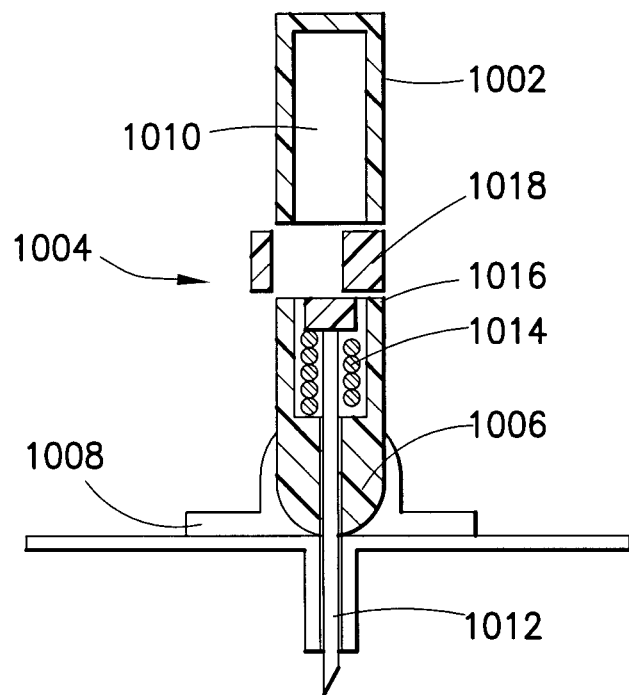
Figure 18C:
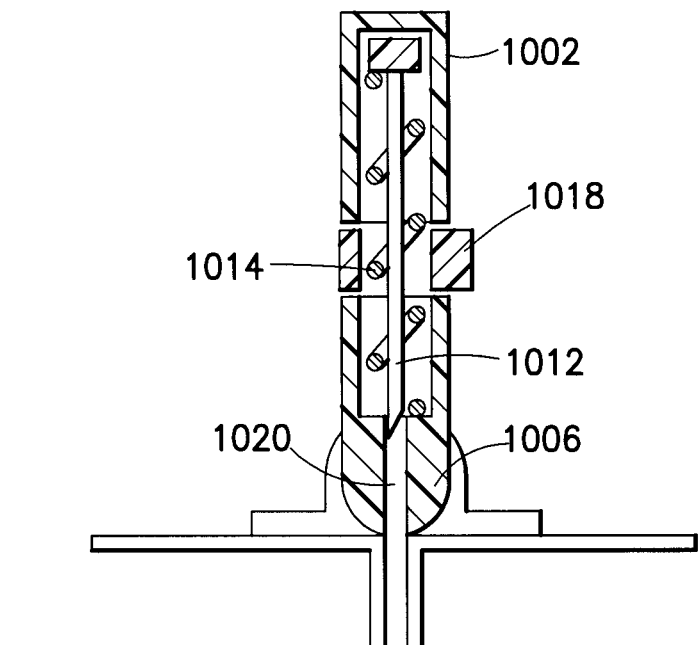
Figure 18D:
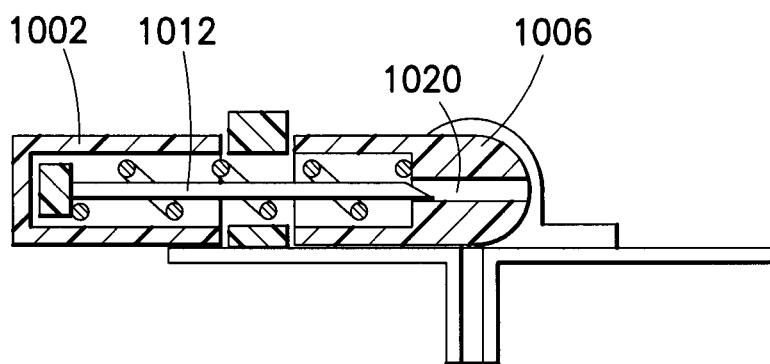

One or more of the exemplary embodiments of the present invention described herein can be further provided with additional features or elements to provide a simple but effective folding/retractable inserter as desired by a user. As shown by way of example, a "folding/retractable" inserter device 1000 is shown in FIGS. 18a-18e. As shown in FIGS. 18a-18e, an exemplary set can be packaged with a hinged, vertical protruding handle 1002 which improves the ability of the user to place it and insert it as shown in FIGS. 18b-18c, but which can be folded out of the way as shown in FIGS. 18a and 18d. To do so, the inserter 1004 can be constructed having a hinge, pivot pin or pivot point, or other flexible-type element 1006 which allows the handle to extend from the set 1008 at a number of angles, especially when the set 1008 is adhered to a skin surface.

As shown the cross-sectional views of FIGS. 18b-18d, the folding/retractable inserter 1000 can comprise the handle 1002 in which a chamber 1010 is provided to contain an insertion needle 1012 and retraction spring 1014. The handle 1002 further comprises at least one opening 1016 through which a user-accessible button 1018 can extend. As shown in FIG. 18b, the opening 1016 and user-accessible button 1018 restrict travel of an end of the needle 1012 such that the retraction spring 1014 is compressed and held in the state shown in FIG. 18b. In such a position, the inserter can be used in a conventional manner. Once the set is in place, the user can press the button 1018 such that the needle 1012 is released and the retraction spring 1014 can retract the needle 1012 from the set and into a protected and covered position within the chamber 1010 of the handle 1002 as shown in FIG. 18c.

As more clearly shown in FIG. 18c, the handle 1002, hinge 1006, and chamber 1010 can further comprise an opening 1020 through which the needle 1012 can be extended and retracted. The opening 1020 is aligned when the handle 1002 is in the upright and perpendicular position. Once the needle 1012 is retracted into the chamber 1010, the handle 1002 can be rotated about the hinge 1006 to any number of positions, but preferably is rotated to a down and substantially parallel position as shown in FIG. 18d. Once in this position, the inserter is left with the set at the site, but maintains a low profile due to the rotation of the handle 1002. Further, no danger is presented by the needle 1012 of the inserter as it is fully retracted into the chamber 1010 of the handle 1002, and is blocked from further escape as the opening 1020 is now blocked.

Figure 18E:
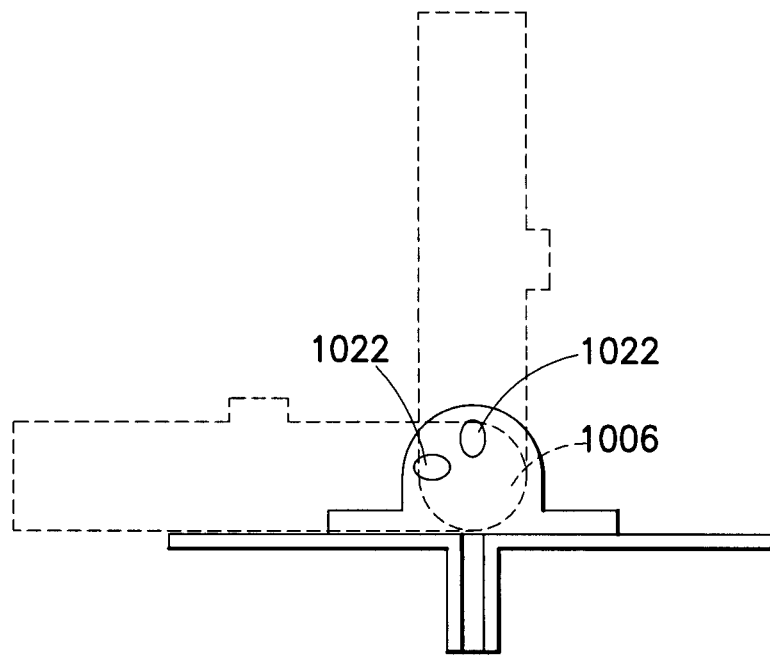

As noted above, the device 1000 can include the user-accessible button 1018 at any convenient location along the handle 1002, such that the button 1018 locks the needle 1012 in an extended position for insertion as shown in FIG. 18b. After insertion, the button 1018 can be activated or toggled, allowing the internal retraction spring 1014 to retract the needle 1012 vertically and automatically to a safe position within the chamber 1010 of the handle 1002 as shown in FIG. 18c. With the needle 1012 fully retracted into the handle body, the handle can be folded down by way of the hinge 1006 as shown in FIG. 18d. Such a hinge 1006 can further comprise a detented hinge to assist in maintaining the folded or upright position of the handle 1002 as shown in FIG. 18e, and to ensure that in the folded position, the sharp component is completely inaccessible and the device assumes and maintains a low profile. To do so, a number of detents 1022 can be provided to gently secure the handle 1002 in either the up or down positions.

Figure 19A:
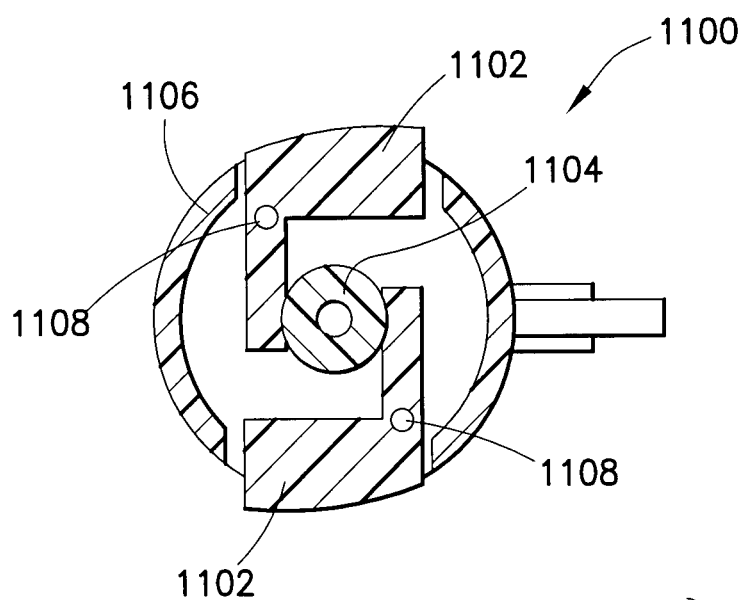
FIGS. 19a-19c are views of an exemplary "squeeze-type" latch provided as a connection method in accordance with an exemplary embodiment of the present invention.
Figure 19B:
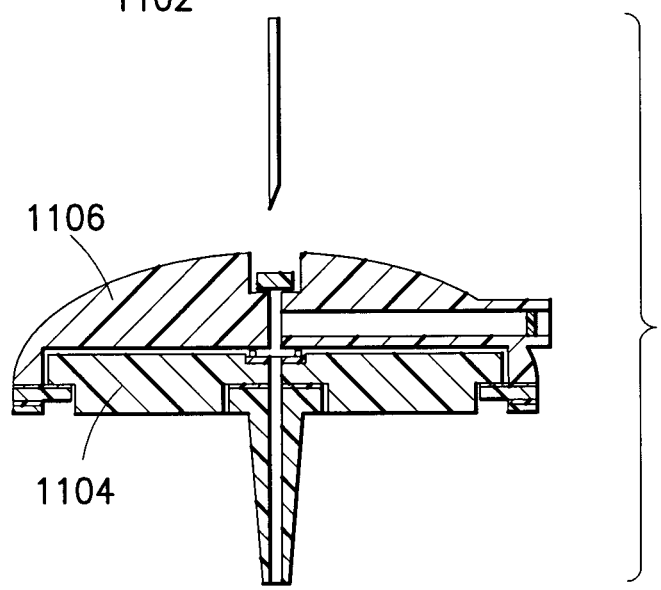
Figure 19C:
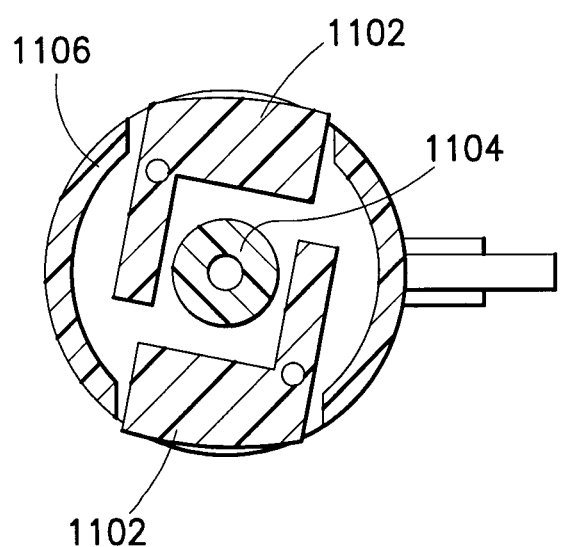

One or more of the exemplary embodiments of the present invention described herein can be further provided with additional features or elements to provide a simple but effective connection method between the tube connection and set in some manner as desired by a user. As shown by way of example, a "squeeze-type" connection device 1100 is shown in FIGS. 19a-19c. As shown in FIGS. 19a-19c, a connection method is provided as a squeeze latch 1100 having one or more hinged and rotatable push buttons within the device that when pressed, release a shoulder, notch or other element of the set.

For example, as shown in FIG. 19a, inside the body of the set 1104, two push button latches 1102 are provided comprising rotatable L shaped elements, with pivot points 1108 located as shown in FIGS. 19a and 19c, and which can be used to secure the tube connection 1106 with the set 1104. The latches 1102 can be urged into the securing position of FIG. 19a using springs, material resilience or other means (not shown). Squeezing the exposed portions of the two latches 1102 toward the center of the device 1100 causes the internal arms of the latches 1102 to swing free of the connection with the set 1104 and release it as shown in FIG. 19c. Once released, the tube connection 1106 and latches 1102 can be lifted from the set 1104. In a similar manner, squeezing the exposed portions of the two latches 1102 toward the center of the device 1100 can be used to place the tube connection 1106 back on the set 1104. Further, such a latching embodiment allows the tube connection 1106 to rotate about the set 1104 prior to, during and after assembly.

Figure 20A:
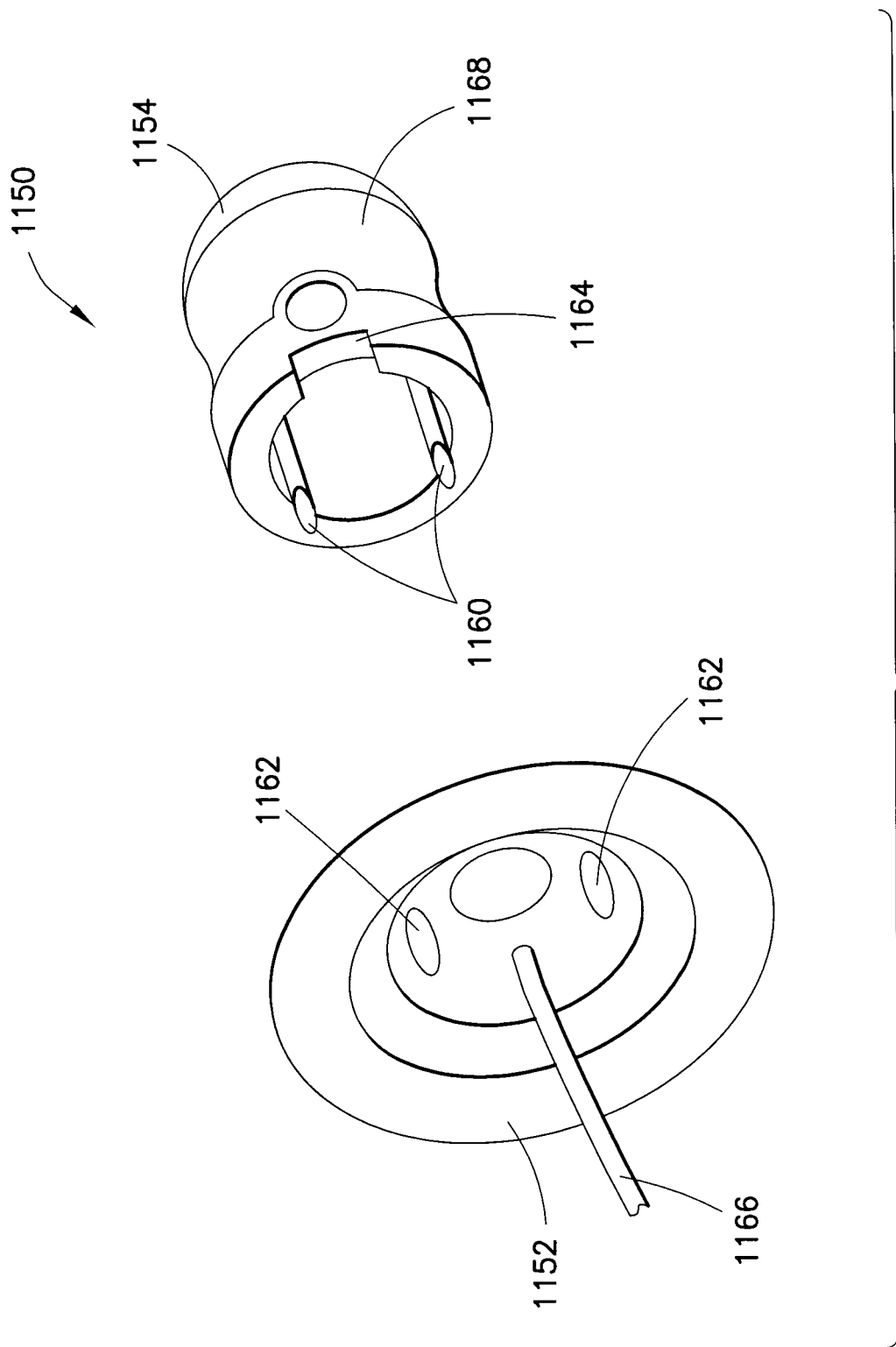

One or more of the exemplary embodiments of the present invention described herein can be further provided with additional features or elements to provide a connection tool and a set configured for use with such a connection tool in some manner as desired by a user. As shown by way of example, a connection tool 1154, tubing connection 1152, and set 1158 are shown in FIGS. 20*a*-20*d*. That is, the device of FIGS. 20*a*-20*d* illustrate an exemplary embodiment of a tool removable connection. Since user accessible connection mechanisms can be bulky or inadvertently actuated, a compromise can be to provide a release mechanism, but to require the use of a removal tool to trigger it as shown in FIG. 20*a*.

Figure 20B:
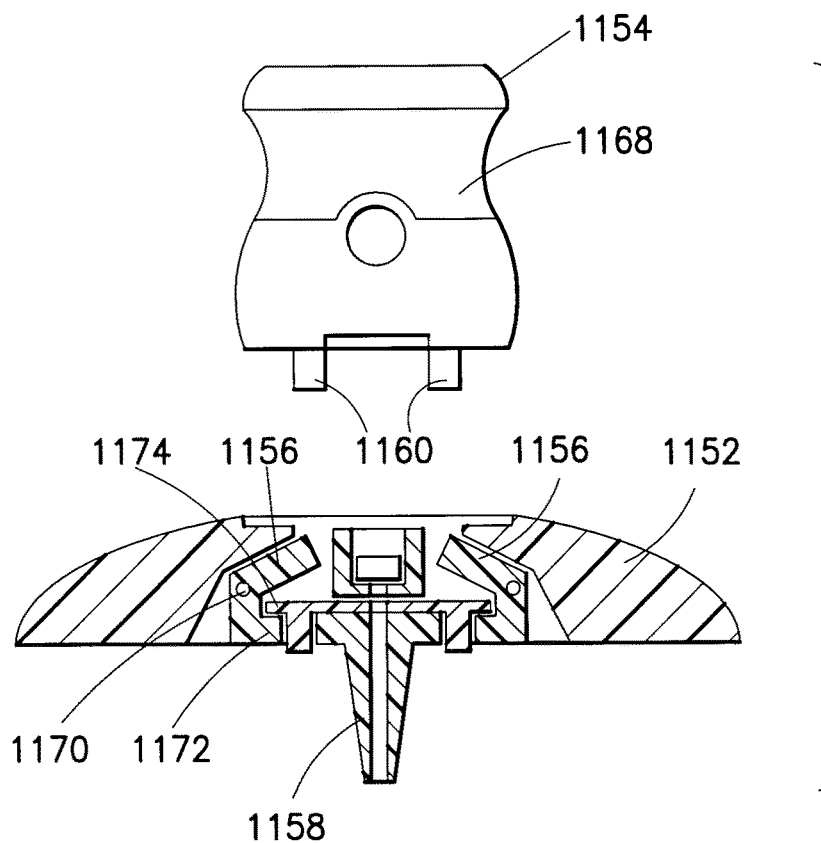
Figure 20C:
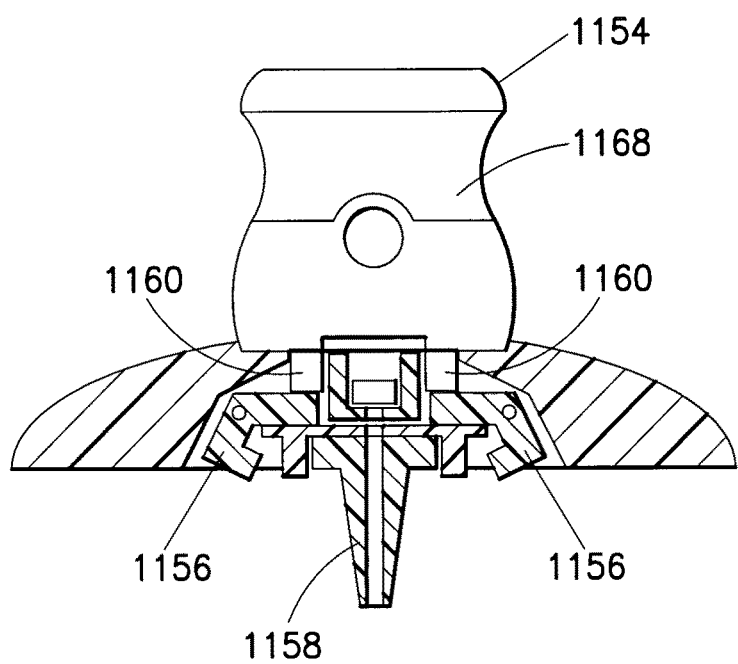

As shown in FIGS. 20*a*-20*c*, the tubing connection 1152 residing on top of the set 1158 will have a low profile, and the housing of the tubing connection 1152 comprises one or more small access openings 1162 as shown. While these openings 1162 are small enough to resist inadvertent disconnection, they permit insertion of specialized features on the external connection tool 1154, which actuates the hinged and rotatable latches 1156 positioned inside the tubing connection 1152 to release it as shown in the cross-sectional views of FIGS. 20*b*-20*d*.

Specifically, the low profile tube connection 1152 is secured to the set 1158 using the hinged and rotatable latches 1156 positioned inside the tubing connection 1152. The tube connection 1152 comprises one or more rotatable brackets 1156 which are configured to rotate about pins 1170. Each of the rotatable latches comprises a shoulder 1172 configured to capture and securely hold a similar shoulder 1174 provided upon the set 1158. Accordingly, in an assembled positions as shown in FIG. 20*b*, the brackets 1156 are rotated into a position that secures the set 1158 That is, when the connection tool 1154 is not assembled with the low profile tube connection 1152 and set 1158, the hinged and rotatable latches 1156 are in upright and secure positions as shown in FIG. 20*b*. Any number of means can be used to maintain the latches 1156 in such an upright position such as springs, material elasticity, and/or contact with the skin surface. While in this position, the latches 1156 serve to capture and secure one or more of the shoulders 1174 of the set 1158.

The connection tool 1154 comprises a substantially cylindrical body having one or more projections or pins 1160 extending from a lower surface. The lower surface can be contoured to more closely match the upper surface of the tube connection 1152. Further, the number and arrangement of pins 1160 and/or openings 1162 can be provided based upon the set such that a particular connection tool can be used with only one or more sets, or a universal tool can be provided to work with all sets. The tool 1154 can be made of any lightweight, strong material such as plastic or metal, and the pins 1160 can be constructed of similar materials to simplify manufacture.

When the connection tool 1154 is pressed against an upper surface of the low profile tube connection 1152, one or more of the pins 1160 extending from the tool 1154 enter the connection 1152 through one or more of the openings 1162 and contact the latches 1156. A notch 1164 can be provided in the tool 1154 to allow clearance for the tube 1166, and the tool can further comprise a contour 1168 and/or other surface or gripping features. Once engaged, the pins 1160 of the tool 1154 press the latches 1156 downward, from the upright and secured positions thereby releasing the set 1158 as shown in FIG. 20*c*. After the connection 1152 is released from the set 1158, the tool 1154 and tube connection 1152 can be lifted free of the set 1158 as shown in FIG. 20*d*.

Figure 21A:
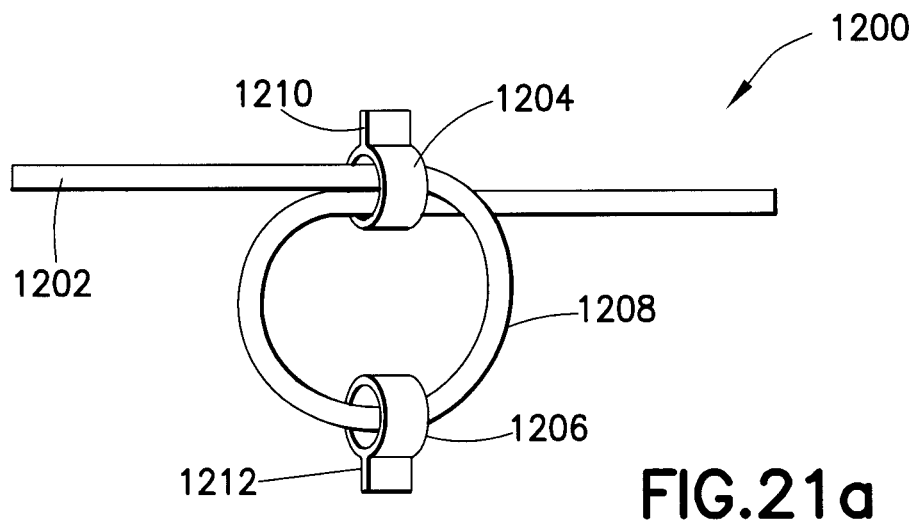
FIGS. 21a-21c are perspective views of an exemplary pull tie, tubing management element in accordance with an exemplary embodiment of the present invention.
Figure 21B:
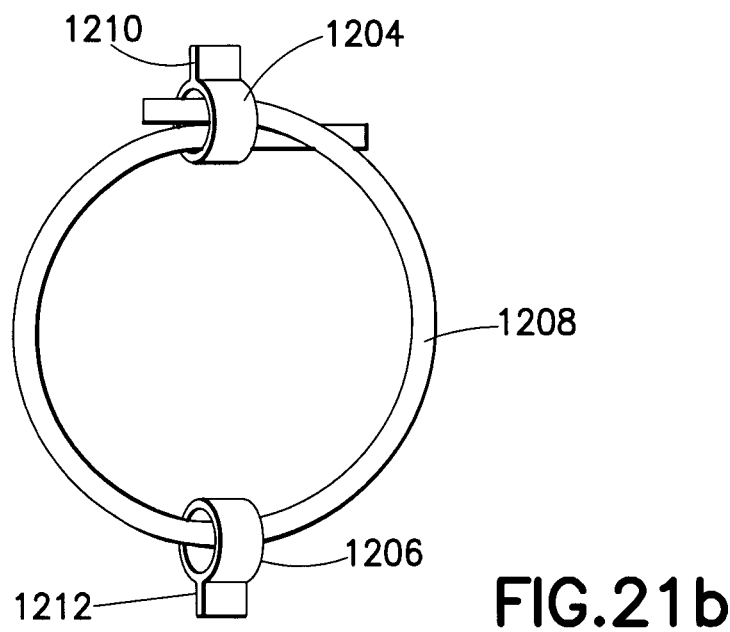
Figure 21C:
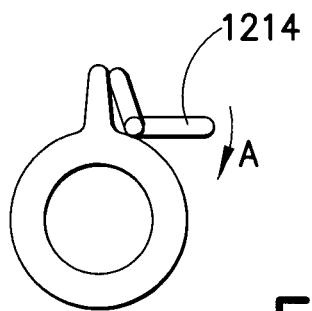

One or more of the exemplary embodiments of the present invention described herein can be further provided with additional features or elements 1200 to manage the tubing of the device in some manner as desired by a user. As shown by way of example, tube management elements 1204 and 1206 are shown in FIGS. 21*a*-21*c*. As shown in FIGS. 21*a*-21*b*, one or more loop control elements 1204 and 1206 can be provided to manage a length of tubing 1202 as desired by the user. Specifically, such tubing management can comprise one or more tubing pull ties 1204 and 1206. The two ties 1204 and 1206 can be constructed having integral pull tabs 1210 and 1212, respectively, and can be installed on a loop 1208 of tubing 1202 as shown. Pulling on the pump and set ends of the tubing 1202 causes additional slack of the loop 1208 to be released, and the loop of FIG. 21*b* to contract as shown in FIG. 21*a*. Pulling outward on the pull tabs 1210 and 1212 can then be used to cause the loop 1208 to expand, and to reduce slack in the tubing as shown in FIG. 21*b*.

As shown in FIG. 21*c*, one or more of the pull ties can further comprise a clip 1214 to attach the loop of tubing to a user, and which can be pressed in the direction of arrow A to release the clip and loop of tubing from a user's belt or other clothing.

Figure 22A:
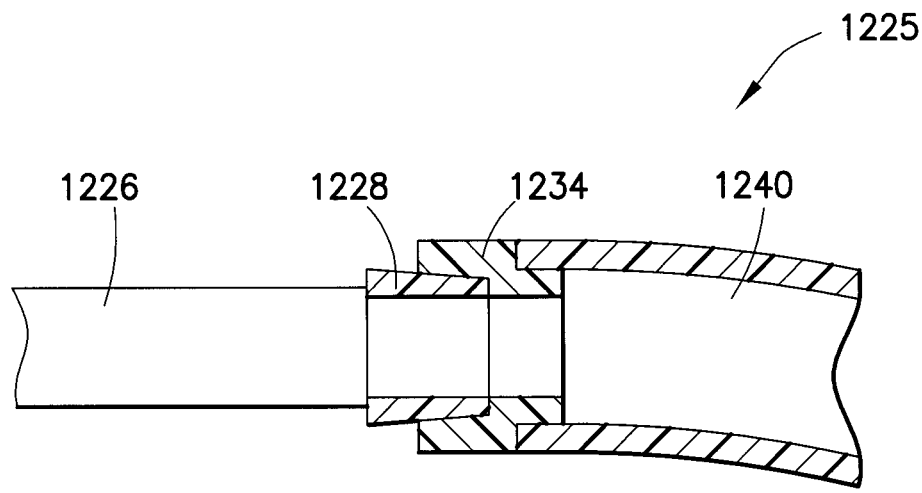
FIGS. 22a-22c are perspective views of exemplary tubing connecting elements in accordance with an exemplary embodiment of the present invention.
Figure 22B:
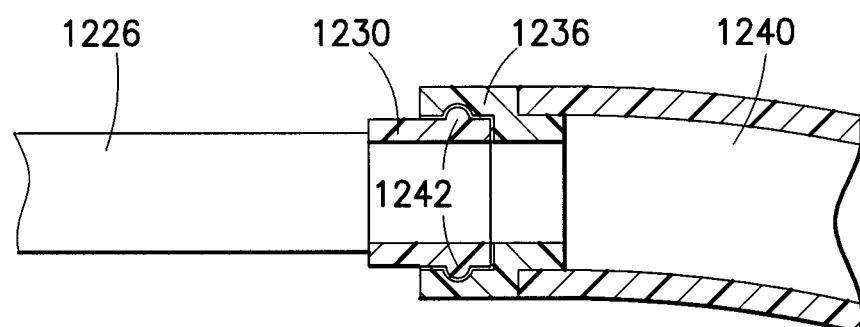
Figure 22C:
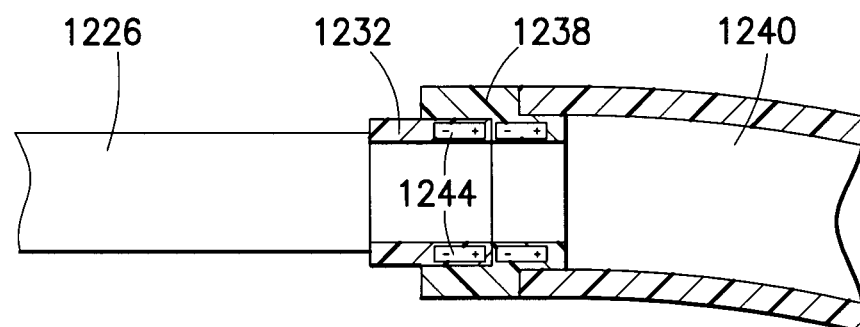

Further, one or more of the exemplary embodiments of the present invention described herein can be further provided with additional features or elements to manage tubing connections of the device in some manner as desired by a user. As shown by way of example, a "breakaway" coupling and/or connecting engagement between tubes 1226 and 1240 is shown in FIGS. 22*a*-22*c*. An advantage of the exemplary embodiments illustrated in FIGS. 22*a*-22*c* is the provision of a secure, leak-free connection, that is easily assembled with a push connection action by the user, and which can disengage automatically when tubing interference occurs, without creating great degrees of tension. That is, the exemplary embodiments illustrated in FIGS. 22*a*-22*c* preferably allow disengagement with minimal "pulling" of opposite tube ends such that the set or pump is not pulled free of the user.

Each exemplary embodiment illustrated in FIGS. 22*a*-22*c* preferably operates as a push connection. The tubing pieces can have male and female ends in which a selected feature provides the desired degree of engagement. As shown in FIG. 22*a*, the male end 1228 of tube 1226 can have a tapered shape, with a diameter and surface characteristics to serve as an in-line, sealable, press-fit with the female end 1234 of tube 1240. In FIG. 22*b*, the male end 1230 can include one or more projecting detents 1242 to provide a snap-fit with similar recessed detents provided in the female end 1236. In yet another exemplary embodiment, the male and female ends 1232 and 1238 can further include magnets 1244, arranged to provide a magnetic attraction between tubes (i.e., north/south magnetic arrangements). In yet other embodiments, one of the magnets can be replaced with a metal element (not shown) which results in a substantially similar attraction with the remaining magnet.

In each embodiment, the coupling and/or connecting engagement between tubes allows for easy disconnect and/or safety breakaway in the event of an accidental snag of the tubing. Further, any one of the exemplary embodiments can be further configured to provide an audible indication of disconnections, such as a "pop" sound or other alert.

Although FIGS. 22a-22c show coupling and/or connecting engagements between tubes 1226 and 1240, in yet other embodiments of the present invention, the features can be used for connections between tube and set, tube and reservoir, and tube and pump.

Figure 23A:
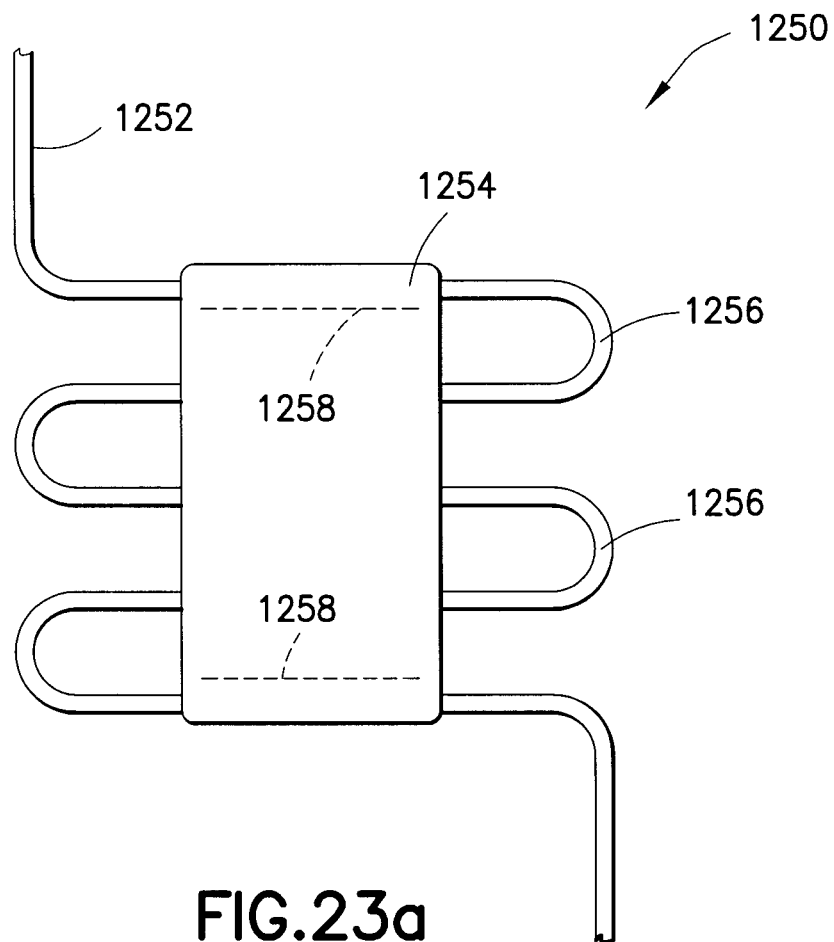
FIGS. 23a-23b are perspective views of an exemplary elastic accordion, tubing management element in accordance with an exemplary embodiment of the present invention.
Figure 23B:
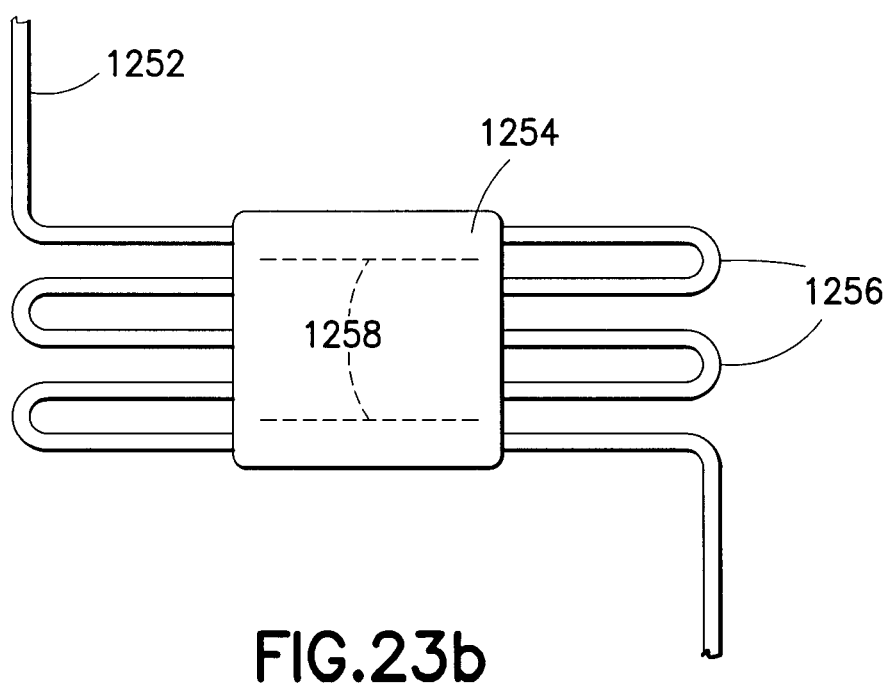

Still further, one or more of the exemplary embodiments of the present invention described herein can be further provided with other additional features or elements to manage the tubing of the device in some manner as desired by a user. As shown by way of example, a tube management element 1250 is shown in FIGS. 23a-23b. As shown in FIGS. 23a-23b, an elastic accordion element 1254 is provided to manage a length of tubing 1252 as desired by the user. The length of the tubing 1252 can be controlled by a back-and-forth looped portion 1256 of the tubing 1252, wrapped in the elastic binding 1254, as shown. The elastic binding 1254 can be provided with one or more stitched or otherwise created seams 1258, to hold and/or direct an entering and exiting segment of tubing to maintain proper operation of the elastic binding during operation. This elastic array of tubing can be expanded and contracted as necessary to allow for the ideal management of the tubing.

Figure 24A:
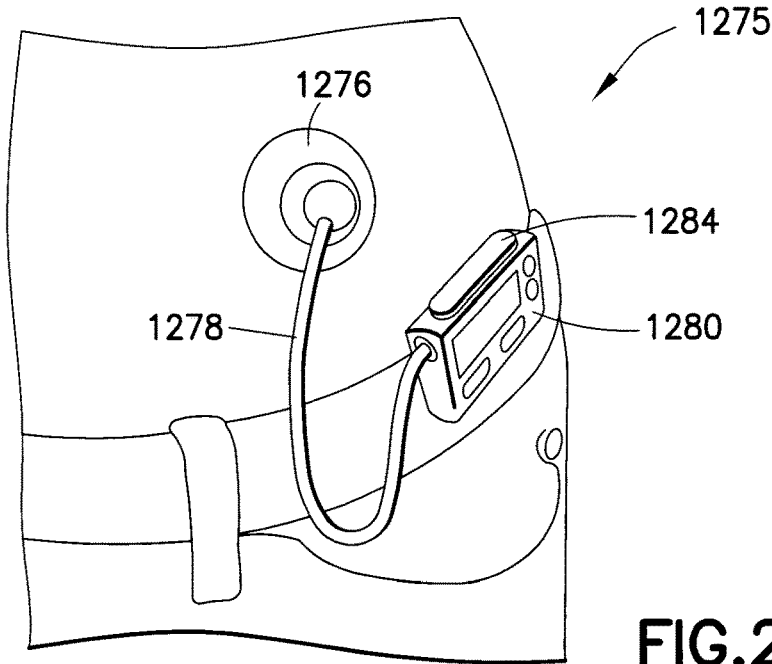
FIGS. 24a-24c are perspective views of an exemplary short tube, tubing management element in accordance with an exemplary embodiment of the present invention.
Figure 24B:
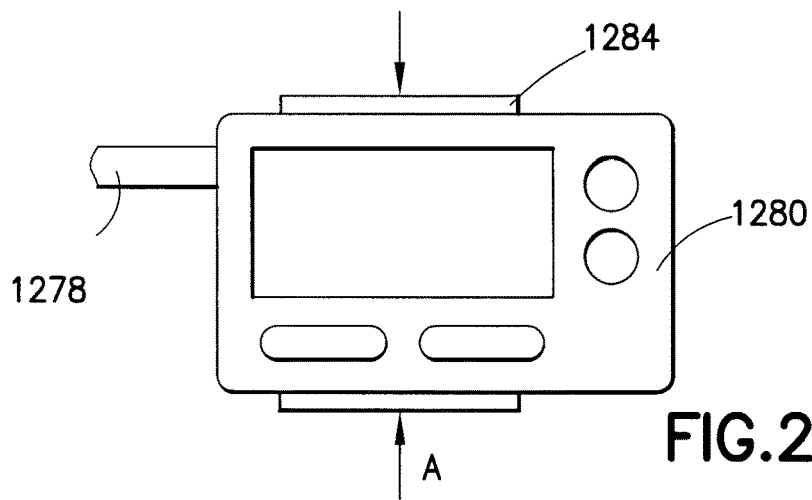
Figure 24C:
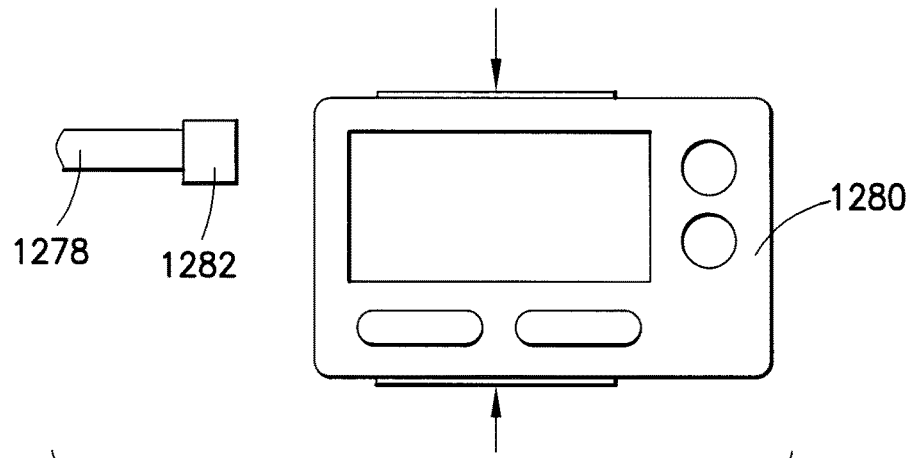

Still further, one or more of the exemplary embodiments of the present invention described herein can be further provided with additional features or elements to minimize the tubing of the device in some manner as desired by a user. Great lengths of tubing can often result in a number of undesirable problems. Accordingly, where it is possible to do so, an exemplary embodiment of the present invention provides a system 1275 which can be safely implemented using a short tube 1278 as shown in FIGS. 24a-24c.

The short tube 1278 provided between the set 1276 and the pump 1280 can be minimal in length, including no slack that may pose a danger of tangling or fouling. The short tube 1278 can also be short enough to allow for disconnection at the pump 1280, such as through any of the disconnecting means described above, leaving the short length of tubing still attached to the site. In an exemplary embodiment of the present invention, the short tube 1278 can be between 2 and 12 inches in length, and preferably between 3 and 9 inches in length and more preferably between 4 and 6 inches in length. The connection 1282 can be a quick-disconnect type, and can be configured to be released by pressing one or more buttons 1284 of the pump 1280 as indicated by the arrows A.

Figure 25A:
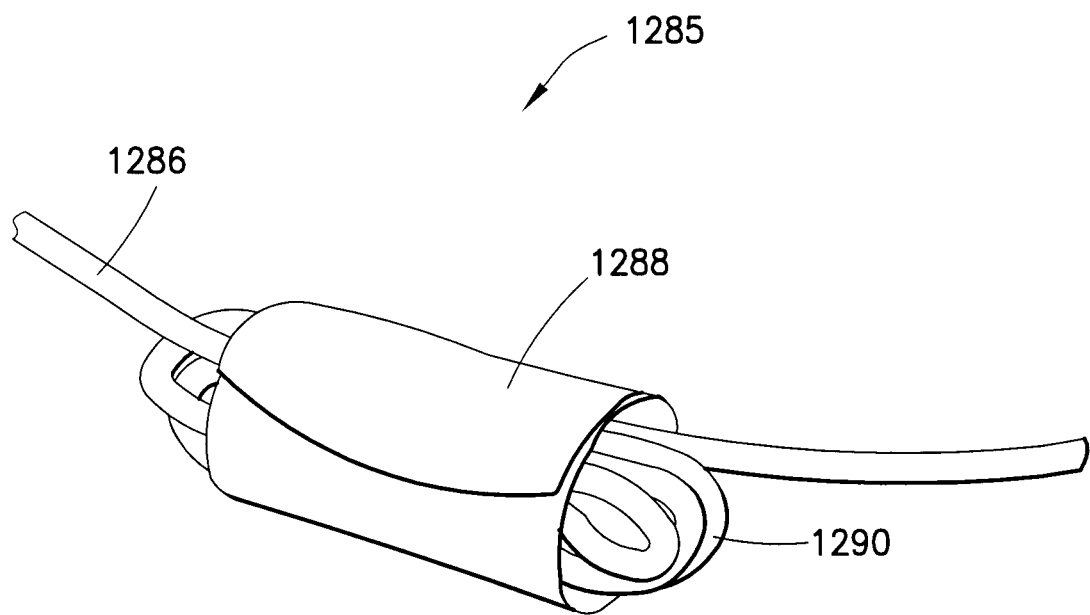
FIGS. 25a-25b are perspective views of exemplary pouch-type, tubing management elements in accordance with an exemplary embodiment of the present invention.
Figure 25B:
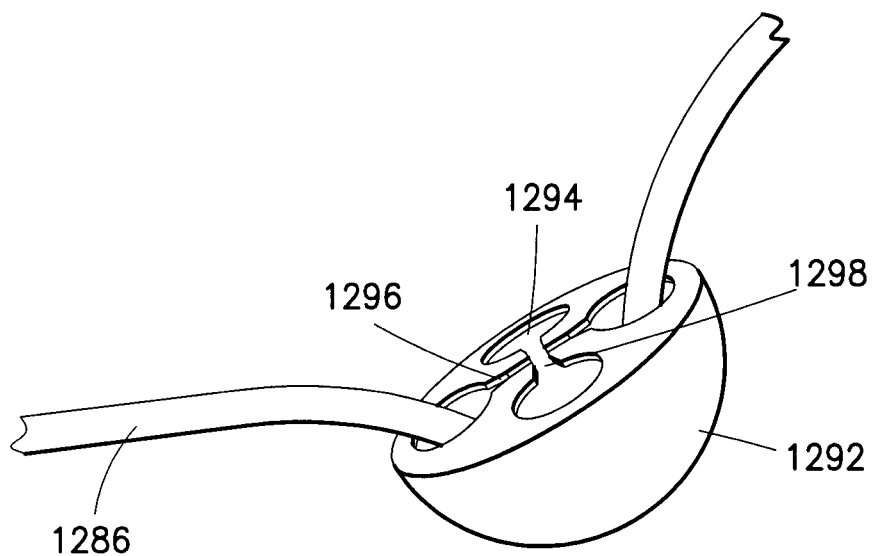

Still further, one or more of the exemplary embodiments of the present invention described herein can be further provided with additional features or elements 1285 to secure, contain, and/or conceal the tubing of the device in some manner as desired by a user. As shown by way of example, a tube containment pouch 1288 is shown in FIG. 25a. The kit can include the pouch 1288 that permits excess tubing 1290 to be bundled up and stowed in such a way as to allow only the required length 1286 to be freed for use. The pouch 1288 can be constructed in a manner substantially similar to that of fabric bag and having a Velcro enclosure, but is not limited thereto. For example, another exemplary embodiment is shown in FIG. 25b in which a flexible part 1292 can be provided that permits the tubing 1286 to be easily inserted and stored out of the way. The flexible part 1292 can be constructed of any suitable material, such as rubber, and can be provided with a number of slotted openings 1294 and 1296, with varying slot 1298 dimensions to facilitate both tubing sizes, and ease of tubing insertion, as desired by the user. The part 1292 can be provided as a half-sphere to maximize both tube containment spacing while maintaining a manageable shape configuration. The pouch 1288 or containment part 1292 can be discarded with the tube.

Figure 26A:
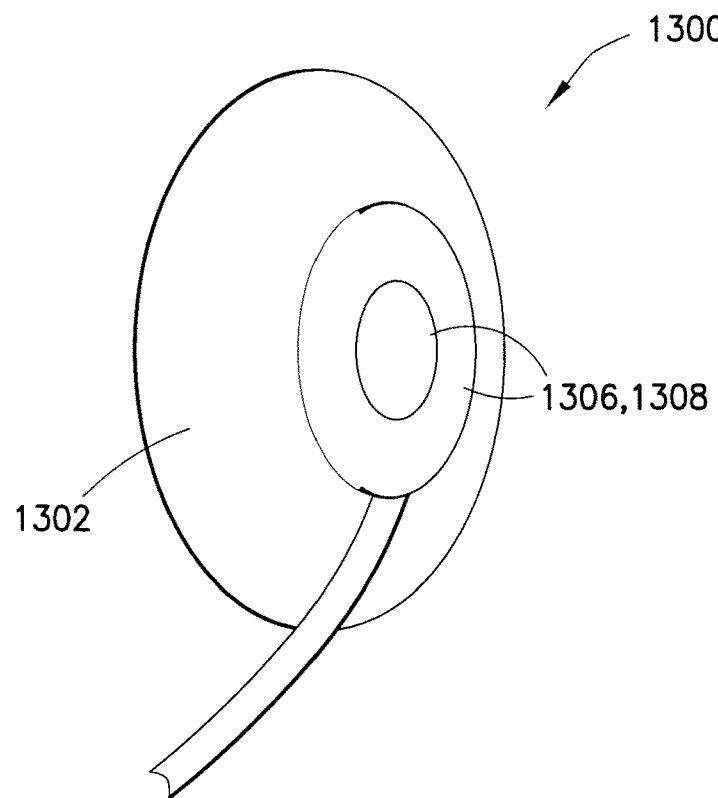
FIGS. 26a-26c are perspective views of exemplary decorative, functional covering elements in accordance with an exemplary embodiment of the present invention.
Figure 26C:
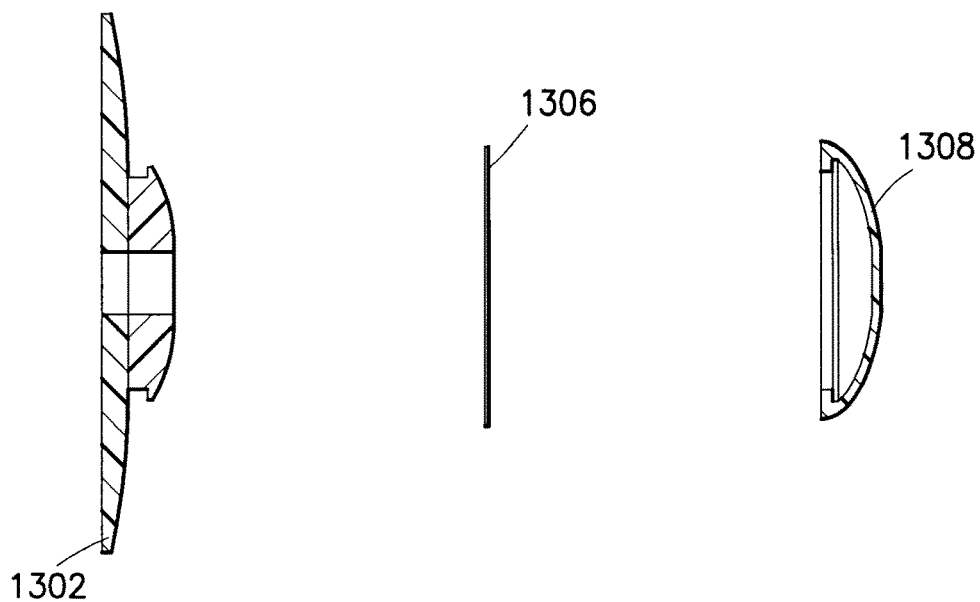
Figure 26B:
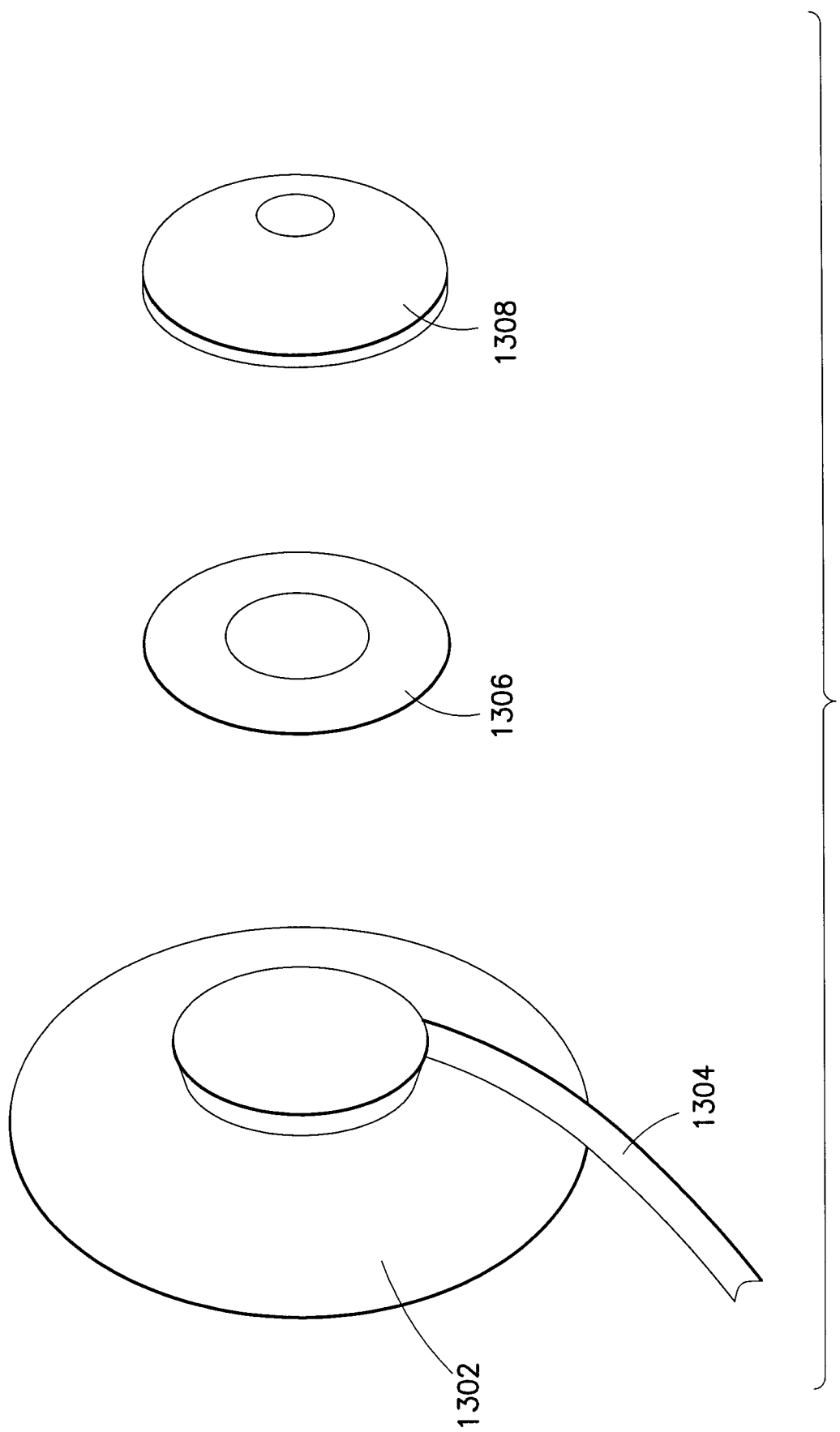

One or more of the exemplary embodiments of the present invention described herein can be further provided with additional features or elements to conceal, decorate, or alter the appearance of the device in some manner as desired by a user. As shown by way of example, an assembled device 1300 of FIG. 26a illustrates a number of such additional features or elements to conceal, decorate, or alter the appearance of the device. In the exemplary embodiment shown, the additional elements are not provided to conceal the device but rather, decorate or alter the appearance in a desired manner. Specifically, instead of providing means to conceal the set 1302 and tube 1304, the inserted set is decorated or ornamented with customizable additional parts 1306 and 1308. For example, as shown in the exploded view of FIGS. 26b and 26c, the set can be provided with an image element 1306 that can be secured to the set 1302 either with a snap fit or other friction-type, adhesive-type, or other attachment, or can be trapped against the set 1302 by a cover piece 1308. In such a manner, the set 1302 can be personalized with the image element 1306 trapped, protected, and/or further customized by the clear, snap-on cover piece 1308.

Figure 27A:
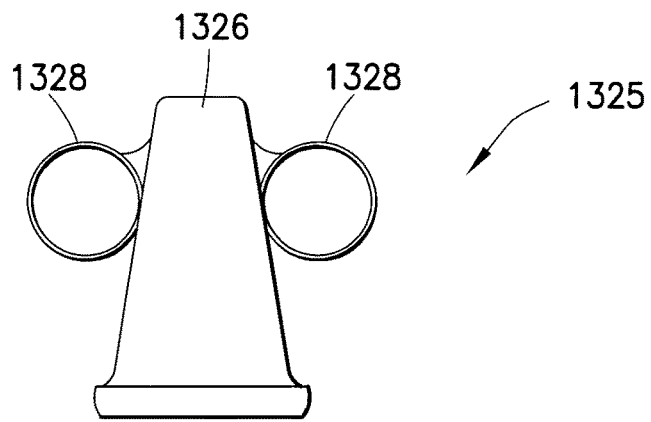
FIGS. 27a-27b are perspective views of an exemplary two-finger, placement element in accordance with an exemplary embodiment of the present invention.
Figure 27B:
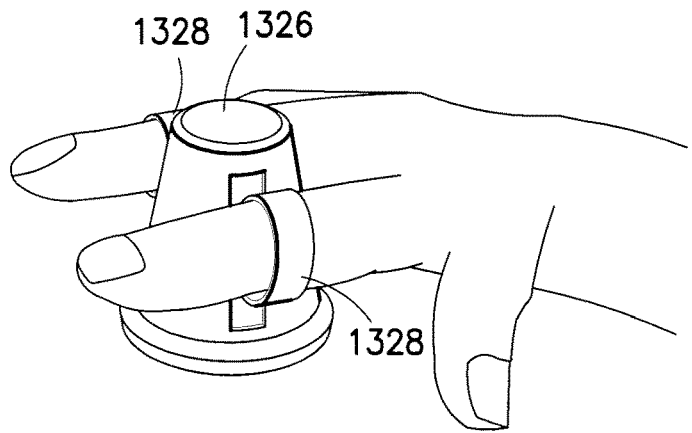

One or more of the exemplary embodiments of the present invention described herein can be further provided with additional features or elements to simplify gripping and user positioning of the inserter. Such an exemplary feature is shown in element 1325 of FIGS. 27a-27b. In the exemplary embodiment shown in FIGS. 27a-27b, an inserter 1326 can be provided with one or more finger loops for use in the placement of the device. In the embodiment shown, the finger loops 1328 allow for two-finger placement as illustrated in FIG. 27b. The set can be placed using such an insertion device 1326 with the two finger loops 1328 as shown, which enhance stability and precision of set placement. Although two completely encircled finger loops are shown, embodiments of the present invention are not limited thereto. In yet other embodiments of the present invention, a combination of complete and partial loops (i.e., spurs) can be used.

Figure 28:
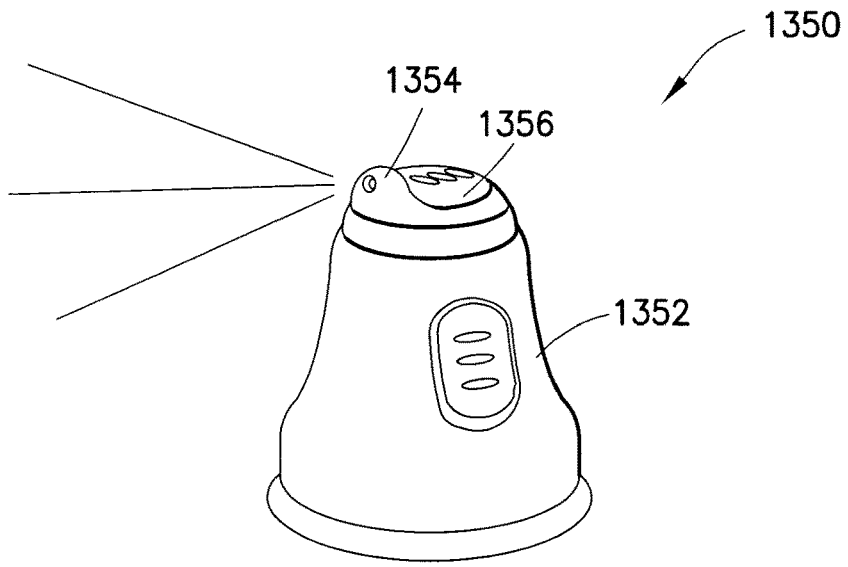
FIG. 28 is a perspective view of an exemplary insertion tool-mounted spray, site preparation element in accordance with an exemplary embodiment of the present invention.

One or more of the exemplary embodiments of the present invention described herein can be further provided with additional features or elements for the use of site preparation. Such an exemplary feature is shown in element 1350 of FIG. 28. In the exemplary embodiment shown in FIG. 28, an inserter 1352, such as those described above, can be provided with a spray mechanism 1354 at an upper most point of the inserter which contains a small amount of site preparation contents. The spray mechanism can be provided with a finger actuator 1356 that can be used by a user to spray the contents upon a site for site preparation. The contents can comprise, but are not limited to, anesthetic, disinfectant, or a combination of both, and can be applied by spraying from a small reservoir (not shown) and outlet incorporated into the insertion device.

Figure 29A:
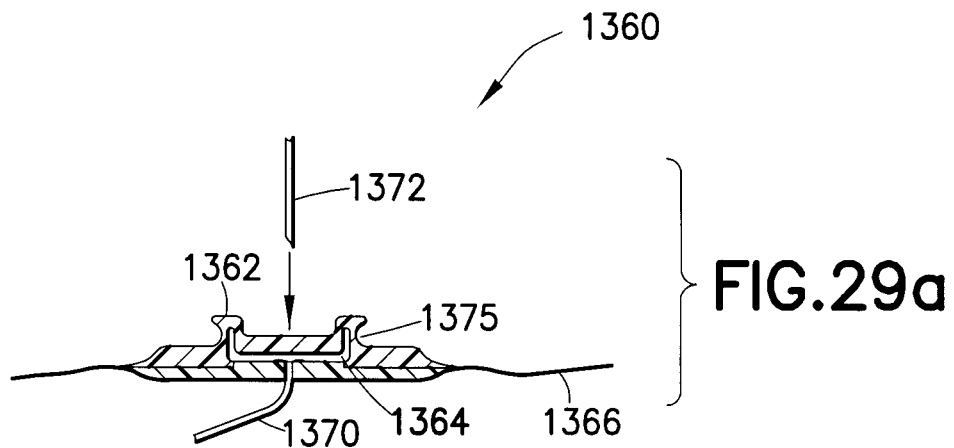
FIG. 29a-29c are views of an exemplary hub including an annular fluid reservoir and/or fluid path for use with one or more exemplary embodiments of the present invention.
Figure 29B:
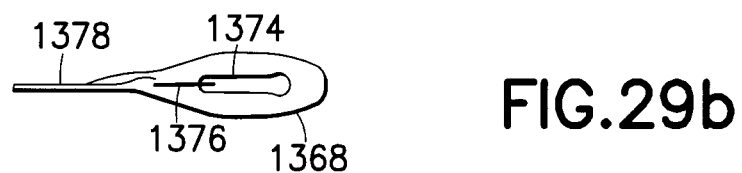
Figure 29C:
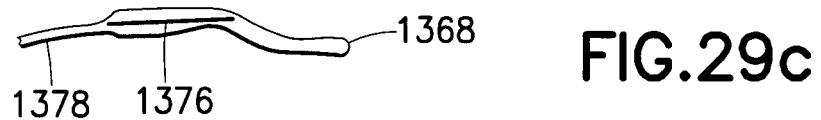

One or more of the exemplary embodiments of the present invention described herein can be further provided with additional features or elements for the provision and use of an advanced design infusion set. Such an exemplary advanced design infusion set is shown comprising, in part, elements 1360 of FIGS. 29a-29c. FIG. 29a is a cross-sectional view of the hub 1362 of the infusion set, in which the hub 1362 provides an annular fluid reservoir and/or fluid path 1364 which can significantly minimize the penetration distance of the tubeset connector into the hub while maintaining a sufficiently large tubeset connector geometry.

The infusion set, as with others described herein, can be provided for the continuous subcutaneous infusion of insulin or other medications. The infusion set comprises the hub 1362, which is affixed to a skin surface 1366 of a body with adhesive as described above, and further comprises a tubeset 1368 which creates and maintains a fluid path from an infusion pump and/or reservoir (not shown) and the hub 1362. The exemplary hub 1362 illustrated in FIG. 29*a* comprises a polyurethane catheter 1370 extending from the hub 1362 through the skin surface 1366 and into the subcutaneous tissue. The hub can be constructed of materials having a viscoelastic property, and which are flexible, such as thermoplastic elastomer (TPE), thermoplastic urethane (TPU), silicone, or similar materials. As with many of the exemplary embodiments of the present invention described herein, the hub 1362 is configured to have a low profile to minimize interference, such as catching on clothing or fixed objects such as doorframes or cabinets. The hub 1362 can be further configured as described herein to have one or more clear or transparent features to enable site visualization and inspection.

The central portion of the hub 1362 can comprise the annular space 1364 in fluid communication with the catheter 1370 lumen. The annular space 1364 can be configured in any number of ways to minimize deadspace within the hub 1362, yet allow insertion needle penetration and subsequent closure of the penetration site, and provide tubeset needle penetration from any number of rotational positions of the tubeset as described in greater detail below. An advantage of providing such a hub 1362 with an annular interior is the ability to minimize the penetration distance of the tubeset connector into the hub while maintaining a sufficiently large tubeset connector geometry. Yet another advantage is the ability to minimize the volume of insulin or other medication left in the hub fluid cavity.

In an exemplary embodiment of the present invention, the annular space 1364 comprises a shallow or narrow central portion such that an upper surface, to be penetrated by the insertion needle 1372, is close to the catheter 1370 lumen. A peripheral area of the annular space 1364 is provided with a wider space extending along the inner wall of the hub 1362. In doing so, the engagement with the tubeset connector is simplified, and further allows tubeset engagement at any rotational position.

The hub 1362 can be inserted through the skin surface 1366 and into the subcutaneous tissue via the insertion needle 1372 that extends through the top surface of the hub 1362, through the annular space 1364 and through the catheter 1370 lumen. After insertion into the skin, the insertion needle 1372 (and needle hub) can be withdrawn and the resulting hole in the hub top surface can be configured to self-seal due to the elastomeric qualities of the hub materials after setting. That is, the annular fluid space 1364 can reseal any insertion openings generated by the insertion needle 1372, and allow penetration by a tubeset connector needle as described in greater detail below.

The exemplary tubeset connector 1368 also comprises, at least in part, the same or similar construction materials. The tubeset connector 1368 can be constructed of a viscoelastic material and utilizes the material characteristics to create and maintain a connection with the hub 1362. The tubeset connector 1368 comprises an elasticized ring 1374 with an inner diameter, shape and profile that matches a central, recessed or grooved portion 1375 of the hub 1362, and a tube 1378. As shown in FIG. 29*a*, the central portion 1375 of the hub 1362 can comprise a groove or contour for guiding, receiving and securing the elasticized ring 1374. To do so, the elasticized ring 1374 can be gently expanded by the user and placed into the central portion 1375 such that when released, the elasticized ring 1374 relaxes into a size and shape that secures the tubeset 1368 with the hub 1362.

At one location of the elasticized ring 1374 inner surface, the tubeset needle or spike 1376 is provided and protrudes radially inward. Accordingly, when the elasticized ring 1374 is placed onto the hub 1362 as described above, the tubeset needle 1376 punctures the wall of the central portion 1375 of the hub 1362 and thereby creates a fluid path from the tubeset 1368 to the annular cavity 1364 of the hub 1362. The elastomeric qualities of the hub materials allow the needle punctures to self seal upon needle removal. In doing so, the tubeset 1368, using the elasticized ring 1374 connector, can be affixed to the hub 1362 in any rotational alignment position. Further, the elasticity of the materials allows the elasticized ring 1374 to be removed from one position and repositioned elsewhere as desired, and each unused insertion site is sealed.

Figure 30:
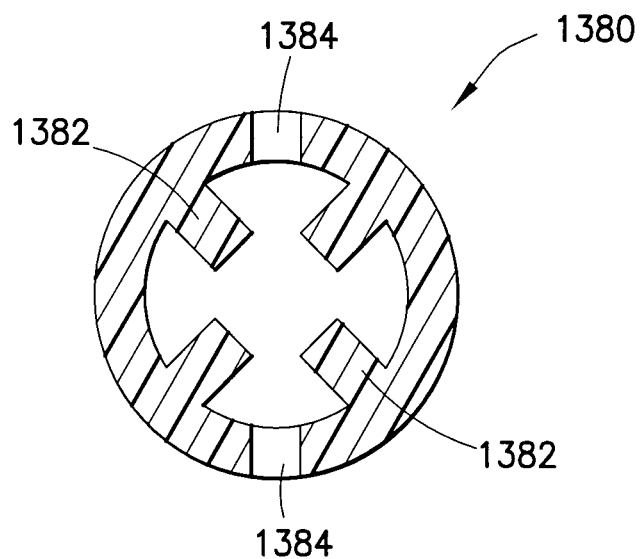
FIG. 30 is a cross-sectional view of a catheter including one or more cross-drilled holes and a splined lumen in accordance with an exemplary embodiment of the present invention.

One or more of the exemplary embodiments of the present invention described herein can be further provided with additional features or elements for the provision and use of an advanced design catheter. Such an exemplary advanced design catheter is shown in element 1380 of FIG. 30. FIG. 30 is a cross-sectional view of a catheter including one or more cross-drilled holes and a splined lumen in accordance with an exemplary embodiment of the present invention. In the exemplary embodiment shown, the catheter 1380 can be constructed of a body temperature softening polyurethane or similar material, such as a proprietary Vialon material, and include one or more features including a splined lumen and holes or openings along a body length, including cross-drilled holes. For example, the catheter can comprise a splined lumen 1382 to prevent kinking, and flow occlusion in the event of a kinked catheter or otherwise. The splines 1382 can be provided as members raised from the inner wall of the catheter 1380 and/or provided as members depressed into the inner wall of the catheter 1380, to be uniformly spaced and to extend along the axis of the catheter. For example, the splines can comprise a linear axis to run parallel to the axis of the catheter and/or can comprise a helical axis, either right-handed or left-handed, to form a helix curve about the axis of the catheter. Although four equally-spaced splines 1382 are shown in FIG. 30, embodiments of the present invention are not limited thereto.

Additionally, the catheter 1380 can comprise on or more holes or openings, such as the cross-drilled holes 1384 shown in FIG. 30. As shown, the holes can be aligned as resulting from drilling, punching or otherwise molding through holes at points along the body of the catheter. Any number of openings or holes can be provided, either uniformly over the body of the catheter or in arrangements of varying concentrations, and can comprise openings of approximately ¼ of the inner diameter of the catheter, but each are not limited thereto. The holes can be provided to facilitate infusion of the contents, such as insulin or other medication, in the subcutaneous tissue adjacent to the catheter in addition to, or instead of, the tissue at the catheter tip.

To this point, a number advanced, improved, and novel new components, elements and packaging of current and future insulin infusion sets, have been described. Accordingly, a number of advantages and improvements over existing systems and methods include the feature of providing the set and some or all of its peripherals in one package. Many of the proposed insertion devices both insert and retract the needle and then cover it for safe disposal. The described fluid connections from the pump to the site require no moving parts and allow for easy disconnection. Other features allow the user to inspect the insertion area for irritation after insertion via a magnifying window in the site, and tube management is obtained by using a tube reel or other embodiment that allows the user to manage excessive tube length conveniently and adjust length as needed. The described insulin reservoir and tube are pre-filled and do not require priming by the user, and the concealment and decorative patches allow the user to cover and protect the site either inconspicuously or with distinction. The described site targeting ring allows the user to more accurately locate the site prior to insertion, and the disposable wipes and sprays combine disinfectant and anesthetic application steps into one step.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

The invention claimed is:

1. An infusion set, comprising:
   a set, comprising a skin contacting surface and a catheter extending from the set;
   a flexible ring having an integral fluid path therethrough, wherein the flexible ring is configured to expand to a first diameter to allow placement over the set, and contract to a second diameter to securely circumscribe an outer diameter of the set;
   a tubing length secured to the flexible ring; and
   a fitting or spike disposed at an end of the tubing length and extending into the flexible ring, the fitting or spike configured to sealably mate with an opening of the set to permit communication of a medicament therebetween.

2. The infusion set of claim 1, wherein the set comprises a hub constructed of a viscoelastic material, wherein the fitting comprises a cannula configured to sealably pierce the hub.

3. The infusion set of claim 2, wherein the viscoelastic material comprises at least one of a thermoplastic elastomer (TPE), thermoplastic urethane (TPU), or silicone.

4. The infusion set of claim 1, further comprising at least one tubing connection, the at least one tubing connection comprising at least one of a tapered tubing end, a tubing end having one or more detents, and a magnetically attractable tubing end.

5. The infusion set of claim 4, wherein the at least one tubing connection is configured to generate an audible indication when disconnected.

6. The infusion set of claim 1, further comprising a medicament supply, the medicament supply comprising at least one medicament container, a tubing segment and a tubing connection connectable to a pump that is connectable to an opposing end of the tubing length, wherein the medicament container is configured to indicate a content quantity therein.

7. The infusion set of claim 1, wherein the catheter comprises a splined lumen, wherein the splined lumen comprises a helical axis.

8. The infusion set of claim 1, wherein the catheter comprises at least one hole or opening along a body length thereof.

9. The infusion set of claim 1, wherein the catheter is constructed of a body temperature softening polyurethane.

10. The infusion set of claim 1, wherein the set comprises at least one push button element, wherein operation of the at least one push button element is configured to release a tube connection from the set.

11. The infusion set of claim 1, wherein the catheter comprises a splined lumen, wherein the splined lumen comprises a linear axis.

12. The infusion set of claim 1, wherein the flexible ring is hollow.

* * * * *